United States Patent
Hino et al.

(10) Patent No.: US 8,048,825 B2
(45) Date of Patent: Nov. 1, 2011

(54) HALOALKYLSULFONANILIDE DERIVATIVES OR SALT THEREOF, HERBICIDE COMPRISING THE DERIVATIVES AS ACTIVE INGREDIENT, AND USE OF THE HERBICIDE

(75) Inventors: Tomokazu Hino, Kawachinagano (JP); Yasuko Yamada, Kawachinagano (JP); Toshihiko Shigenari, Kawachinagano (JP); Koki Mametsuka, Kawachinagano (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 242 days.

(21) Appl. No.: 12/312,469

(22) PCT Filed: Nov. 16, 2007

(86) PCT No.: PCT/JP2007/072256
§ 371 (c)(1),
(2), (4) Date: May 12, 2009

(87) PCT Pub. No.: WO2008/059948
PCT Pub. Date: May 22, 2008

(65) Prior Publication Data
US 2010/0016164 A1    Jan. 21, 2010

(30) Foreign Application Priority Data
Nov. 17, 2006 (JP) .................. 2006-312140

(51) Int. Cl.
| *C07D 265/08* | (2006.01) |
| *C07D 265/10* | (2006.01) |
| *C07D 267/06* | (2006.01) |
| *A01N 47/04* | (2006.01) |
| *A01N 33/18* | (2006.01) |
| *A01N 43/72* | (2006.01) |
| *A01N 43/86* | (2006.01) |

(52) U.S. Cl. ........... 504/218; 504/223; 540/488; 544/97
(58) Field of Classification Search .................. 504/218, 504/223; 544/97; 540/488
See application file for complete search history.

(56) References Cited

FOREIGN PATENT DOCUMENTS
| JP | 2000-247814 | 9/2000 |
| JP | 2003-055346 | 2/2003 |
| JP | 2005-314407 | 11/2005 |
| WO | WO 2004/011429 | 2/2004 |
| WO | WO 2006/090792 | 8/2006 |

*Primary Examiner* — Bruck Kifle
(74) *Attorney, Agent, or Firm* — Paul E. White, Jr.; Manelli Selter PLLC

(57) ABSTRACT

A haloalkylsulfonanilide derivative represented by general formula (I) or a salt thereof wherein $R^1$ represents a halo($C_1$-$C_8$)alkyl group, $R^2$, $R^3$, $R^4$, $R^5$, $R^6$, $R^7$, $R^8$, $R^9$ and $R^{10}$ represent hydrogen atoms, etc., n represents 1 or 2, A represents an oxygen atom, W represents an oxygen atom, X represents a halogen atom and m represents an integer of 0 to 4, are compounds useful as herbicides having both of remarkable herbicidal effect and characteristics such as excellent crop-weed selectivity. General formula (I):

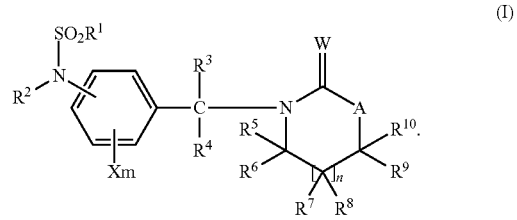

5 Claims, No Drawings

HALOALKYLSULFONANILIDE DERIVATIVES OR SALT THEREOF, HERBICIDE COMPRISING THE DERIVATIVES AS ACTIVE INGREDIENT, AND USE OF THE HERBICIDE

This application is the national phase of international application PCT/JP2007/072256 filed 16 Nov. 2007 which designated the U.S.

TECHNICAL FIELD

The present invention relates to a novel haloalkylsulfonanilide derivative or a salt thereof, a herbicide comprising the same as an active ingredient and a method of using the same.

BACKGROUND ART

It has been conventionally known that a compound having a skeleton in which a haloalkylsulfonanilide derivative and a heterocycle are linked via a spacer such as an alkylene group on a nitrogen atom in the heterocycle is useful as a herbicide (For example, refer to JP-A-2004-107322 or JP-A-2006-265240). However, haloalkylsulfonanilide derivatives linked to a 6- to 7-membered ring, which is the present invention, and the herbicidal activity thereof have not been known.

DISCLOSURE OF THE INVENTION

As mentioned above, it is known that a certain haloalkylsulfonanilide derivative is useful as a herbicide but characteristics such as herbicidal effect, wide applicability for a number of weed species including hard-to-control weeds, residual effect, excellent crop-weed selectivity are not sufficient, and the creation of a herbicide composition having more excellent characteristics has been demanded. Therefore, an object of the present invention is to provide a compound which is useful as a herbicide having both of a remarkable herbicidal effect and characteristics such as excellent crop-weed selectivity.

The present inventors have conducted extensive studies on the synthesis of a derivative having a sulfonanilide structure and the bioactivity thereof in order to develop a novel herbicide and consequently have found that novel haloalkylsulfonanilide derivatives represented by general formula (I) of the present invention are useful as herbicides having all of a remarkable herbicidal effect, wide applicability for a number of weed species including hard-to-control weeds, residual effect and excellent crop-weed selectivity and that they are particularly useful as rice herbicides, and thus complete the present invention.

That is, the present invention relates to a haloalkylsulfonanilide derivative represented by general formula (I)

[Formula 1]

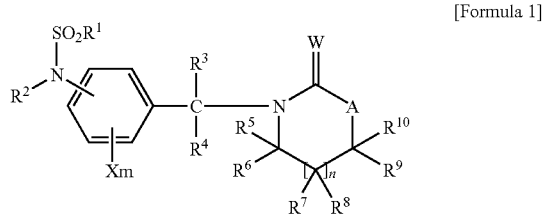

wherein $R^1$ represents a halo($C_1$-$C_8$)alkyl group; $R^2$ represents a hydrogen atom; a ($C_1$-$C_6$)alkoxycarbonyl($C_1$-$C_6$) alkyl group; a ($C_1$-$C_{18}$)alkylcarbonyl group; a halo($C_1$-$C_6$) alkylcarbonyl group; a phenylcarbonyl group; a substituted phenylcarbonyl group having 1 to 5 substituents, which may be the same or different, selected from Y as defined below; a ($C_1$-$C_{18}$)alkoxycarbonyl group; a ($C_2$-$C_{18}$)alkenyloxycarbonyl group; a ($C_2$-$C_{18}$)alkynyloxycarbonyl group; a halo($C_1$-$C_6$)alkoxycarbonyl group; a ($C_1$-$C_6$)alkoxy($C_1$-$C_6$)alkoxycarbonyl group; a ($C_1$-$C_6$)alkylthio($C_1$-$C_6$)alkoxycarbonyl group; a ($C_1$-$C_6$)alkylsulfinyl($C_1$-$C_6$)alkoxycarbonyl group; a ($C_1$-$C_6$)alkylsulfonyl($C_1$-$C_6$)alkoxycarbonyl group; a phenoxycarbonyl group; a substituted phenoxycarbonyl group having 1 to 5 substituents, which may be the same or different, selected from Y as defined below; a phenoxy($C_1$-$C_6$)alkylcarbonyl group; a substituted phenoxy($C_1$-$C_6$)alkylcarbonyl group having 1 to 5 substituents, which may be the same or different, selected from Y as defined below; a benzyloxycarbonyl group; a substituted benzyloxycarbonyl group having 1 to 5 substituents, which may be the same or different, selected from Y as defined below; a ($C_1$-$C_6$)alkylthiocarbonyl group; ($C_1$-$C_6$)alkylsulfonyl group; a halo($C_1$-$C_6$)alkylsulfonyl group; a phenylsulfonyl group; a substituted phenylsulfonyl group having 1 to 5 substituents, which may be the same or different, selected from Y as defined below; a ($C_1$-$C_6$)alkyl group; a ($C_2$-$C_6$)alkenyl group; a ($C_2$-$C_6$)alkynyl group; a phenyl($C_1$-$C_6$)alkyl group; a substituted phenyl($C_1$-$C_6$)alkyl group having 1 to 5 substituents on the ring, which may be the same or different, selected from Y as defined below; a phenylcarbonyl($C_1$-$C_6$)alkyl group; a substituted phenylcarbonyl($C_1$-$C_6$)alkyl group having 1 to 5 substituents on the ring, which may be the same or different, selected from Y as defined below; a ($C_1$-$C_8$)alkoxy($C_1$-$C_6$)alkyl group; a ($C_1$-$C_6$)alkoxy($C_1$-$C_6$)alkoxy($C_1$-$C_6$)alkyl group; a tri($C_1$-$C_6$) alkylsilyl($C_1$-$C_6$)alkoxy($C_1$-$C_6$)alkyl group which may be the same or different; a phenyl($C_1$-$C_6$)alkoxy($C_1$-$C_6$)alkyl group; a substituted phenyl($C_1$-$C_6$)alkoxy($C_1$-$C_6$)alkyl group having 1 to 5 substituents on the ring, which may be the same or different, selected from Y as defined below; a ($C_1$-$C_6$) alkylcarbonyloxy($C_1$-$C_6$)alky group; a phenylcarbonyloxy ($C_1$-$C_6$)alkyl group; a substituted phenylcarbonyloxy($C_1$-$C_6$) alkyl group on the ring, which may be the same or different, selected from Y as defined below; a phenylcarbonyloxy($C_1$-$C_6$)alkoxy($C_1$-$C_6$)alkyl group; a substituted phenylcarbonyloxy($C_1$-$C_6$)alkoxy($C_1$-$C_6$)alkyl group having 1 to 5 substituents on the ring selected from Y as defined below; a ($C_1$-$C_6$) alkoxycarbonyloxy($C_1$-$C_6$)alkyl group; a mono($C_1$-$C_6$) alkylaminocarbonyloxy($C_1$-$C_6$)alkyl group; a di($C_1$-$C_6$) alkylaminocarbonyloxy($C_1$-$C_6$)alkyl group which may be the same or different and may be linked to each other to form a 5- to 8-membered ring; a phenylaminocarbonyloxy($C_1$-$C_6$) alkyl group; a substituted phenylaminocarbonyloxy($C_1$-$C_6$) alkyl group having 1 to 5 substituents on the ring, which may be the same or different, selected from Y as defined below; an N-($C_1$-$C_6$)alkyl-N-phenylaminocarbonyloxy($C_1$-$C_6$)alkyl group; a substituted N-($C_1$-$C_6$) alkyl-N-phenylaminocarbonyloxy($C_1$-$C_6$)alkyl group having 1 to 5 substituents on the ring, which may be the same or different, selected from Y as defined below; a phenylthio($C_1$-$C_6$)alkyl group; a substituted phenylthio($C_1$-$C_6$)alkyl group having 1 to 5 substituents on the ring, which may be the same or different, selected from Y as defined below; a phenylsulfonyl($C_1$-$C_6$)alkyl group; a substituted phenylsulfonyl($C_1$-$C_6$)alkyl group having 1 to 5 substituents on the ring, which may be the same or different, selected from Y as defined below; a phenyl ($C_1$-$C_6$)alkylthio ($C_1$-$C_6$)alkyl group; a substituted phenyl($C_1$-$C_6$)alkylthio ($C_1$-$C_6$)alkyl group having 1 to 5 substituents on the ring, which may be the same or different, selected from Y as defined below; a phenyl($C_1$-$C_6$)alkylsulfonyl($C_1$-$C_6$)alkyl group; a substituted phenyl($C_1$-$C_6$)alkylsulfonyl($C_1$-$C_6$)alkyl group having 1 to 5 substituents on the ring, which may be the same or different, selected from Y as defined below; a ($C_1$-$C_6$)alkylthio($C_1$-$C_6$)alkyl group; a halo($C_1$-$C_6$)alkylthio($C_1$-$C_6$)alkyl group; a thiocyanato($C_1$-$C_6$)alkyl group; a heterocyclic($C_1$-$C_6$)alkyl group, wherein the heterocycle represents pyridine, pyridine-N-oxide, pyrimidine, pyrazine, triazine, furan, tetrahydrofuran, thiophene, tetrahydrothiophene, tetrahydropyran, tetrahydrothiopyran, oxazole, isoxazole, oxadiazole, thiazole, isothiazole, thiadiazole, imidazole, triazole, pyrazole, pyrrol, pyrrolidine, phthalimide or 2,3-dihydro-1,2-benzothiazol-3-one 1,1-dioxide; or a substituted heterocyclic($C_1$-$C_6$)alkyl group having 1 to 4 substituents on the ring, which may be the same or different, selected from Y as defined below, wherein the heterocycle is the same as above, $R^3$ and $R^4$, which may be the same or different, each represents a hydrogen atom; a ($C_1$-$C_6$)alkyl group; a ($C_3$-$C_6$)cycloalkyl group; a ($C_1$-$C_6$)alkoxy group; a halogen atom or a cyano group, and $R^3$ and $R^4$ may be linked to each other to form a 3- to 7-membered ring;

$R^5$ and $R^6$, which may be the same or different, each represents a hydrogen atom; a ($C_1$-$C_6$)alkyl group; a ($C_3$-$C_6$) cycloalkyl group; a ($C_1$-$C_6$)alkoxy group; a halogen atom; or a cyano group;

$R^7$, $R^8$, $R^9$ and $R^{10}$, which may be the same or different, each represents a hydrogen atom; a halogen atom; a ($C_1$-$C_6$) alkyl group; a ($C_3$-$C_6$)cycloalkyl group; a ($C_1$-$C_6$)alkoxy group; a halo($C_1$-$C_6$)alkyl group; a ($C_1$-$C_6$)alkoxy($C_1$-$C_6$) alkyl group; a ($C_1$-$C_6$)alkylcarbonyloxy($C_1$-$C_6$)alkyl group; a mono($C_1$-$C_6$)alkylamino ($C_1$-$C_6$)alkyl group; a di($C_1$-$C_6$) alkylamino ($C_1$-$C_6$)alkyl group which may be the same or different; a mono($C_1$-$C_6$)alkylaminocarbonyl($C_1$-$C_6$)alkyl group; a di($C_1$-$C_6$)alkylaminocarbonyl($C_1$-$C_6$)alkyl group which may be the same or different; a phenyl($C_1$-$C_6$)alkyl group; a substituted phenyl($C_1$-$C_6$)alkyl group having 1 to 5 substituents on the ring, which may be the same or different, selected from Y as defined below; a phenoxy($C_1$-$C_6$)alkyl group; a substituted phenoxy($C_1$-$C_6$)alkyl group having 1 to 5 substituents on the ring, which may be the same or different, selected from Y as defined below; a phenyl group; a substituted phenyl group having 1 to 5 substituents on the ring, which may be the same or different, selected from Y as defined below; a ($C_1$-$C_6$)alkoxycarbonyl group; a mono($C_1$-$C_6$)alkylaminocarbonyl group; a di($C_1$-$C_6$)alkylaminocarbonyl group which may be the same or different; a hydroxyl group; or a cyano group, and $R^5$, $R^6$, $R^7$, $R^8$, $R^9$ and $R^{10}$ may be respectively linked to an adjacent substituent to form a 3- to 7-membered ring through a ($C_1$-$C_4$)alkylene group which may be the same or different and may be interrupted with one or two hetero atoms selected from an oxygen atom, a sulfur atom, or a nitrogen atom; wherein the nitrogen atom may be substituted with a hydrogen atom; a ($C_1$-$C_6$)alkyl group, a ($C_2$-$C_6$)alkenyl group, a ($C_2$-$C_6$)alkynyl group or a cyclo ($C_3$-$C_6$)alkyl group;

n represents 1 or 2;

A represents an oxygen atom or a sulfur atom;

W represents an oxygen atom or a sulfur atom;

X may be the same or different and represents a halogen atom; a ($C_1$-$C_6$)alkyl group; a ($C_2$-$C_6$)alkenyl group; a ($C_2$-$C_6$)alkynyl group; a cyclo($C_3$-$C_6$)alkyl group; a halo($C_1$-$C_6$) alkyl group; a cyclohalo($C_3$-$C_6$)alkyl group; a ($C_1$-$C_6$)alkoxy group; a halo($C_1$-$C_6$)alkoxy group; a ($C_1$-$C_6$)alkoxy($C_1$-$C_6$) alkyl group; a halo($C_1$-$C_6$)alkoxy($C_1$-$C_6$)alkyl group; a ($C_1$-$C_6$)alkylthio group; a halo($C_1$-$C_6$)alkylthio group; a ($C_1$-$C_6$) alkylthio($C_1$-$C_6$)alkyl group; a halo($C_1$-$C_6$)alkylthio($C_1$-$C_6$) alkyl group; a ($C_1$-$C_6$)alkylsulfinyl group; a halo($C_1$-$C_6$) alkylsulfinyl group; a ($C_1$-$C_6$)alkylsulfonyl group; a halo($C_1$-$C_6$)alkylsulfonyl group; a phenyl group; a substituted phenyl group having 1 to 5 substituents, which may be the same or different, selected from Y as defined below; a phenoxy group; a substituted phenoxy group having 1 to 5 substituents, which may be the same or different, selected from Y as defined below; a phenylthio group; a substituted phenylthio group having 1 to 5 substituents, which may be the same or different, selected from Y as defined below; a phenylsulfinyl group; a substituted phenylsulfinyl group having 1 to 5 substituents, which may be the same or different, selected from Y as defined below; a phenylsulfonyl group; a substituted phenylsulfonyl group having 1 to 5 substituents, which may be the same or different, selected from Y as defined below; a ($C_1$-$C_6$)alkylcarbonyl group, a halo($C_1$-$C_6$)alkylcarbonyl group, a phenylcarbonyl group; a substituted phenylcarbonyl group having 1 to 5 substituents, which may be the same or different, selected from Y as defined below; a ($C_1$-$C_6$)alkoxycarbonyl group; a carboxyl group; a mono($C_1$-$C_6$)alkylaminocarbonyl group; di($C_1$-$C_6$)alkylaminocarbonyl group which may be the same or different; a phenylaminocarbonyl group; a substituted phenylaminocarbonyl group having 1 to 5 substituents on the ring, which may be the same or different, selected from Y as defined below; a phenyl($C_1$-$C_6$)alkylaminocarbonyl group; a substituted phenyl($C_1$-$C_6$)alkylaminocarbonyl group having 1 to 5 substituents on the ring, which may be the same or different, selected from Y as defined below; a hydroxyl group or a cyano group; and m represents an integer of 0 to 4, and X may be taken together with an adjacent carbon atom on the benzene ring to form a 5- or 6-membered ring through a ($C_1$-$C_4$)alkylene group which may be the same or different and may be interrupted with one or two hetero atoms selected from an oxygen atom, a sulfur atom, or a nitrogen atom which may be substituted with a hydrogen atom, a ($C_1$-$C_6$)alkyl group, a ($C_2$-$C_6$)alkenyl group, a ($C_2$-$C_6$)alkynyl group or a cyclo ($C_3$-$C_6$)alkyl group;

Y, which may be the same or different, represents 1 to 5 substituents selected from a halogen atom; a nitro group; a ($C_1$-$C_6$)alkyl group; a ($C_2$-$C_6$)alkenyl group; a ($C_2$-$C_6$)alkynyl group; a cyclo($C_3$-$C_6$)alkyl group; a halo($C_1$-$C_6$)alkyl group; a cyclohalo($C_3$-$C_6$)alkyl group; a ($C_1$-$C_6$)alkoxy group; a halo($C_1$-$C_6$)alkoxy group; a cyano ($C_1$-$C_6$)alkoxy group; a ($C_1$-$C_6$)alkoxy($C_1$-$C_6$)alkoxy group; a ($C_1$-$C_6$)alkylthio group; a halo($C_1$-$C_6$)alkylthio group; a ($C_1$-$C_6$)alkylsulfinyl group; a halo($C_1$-$C_6$)alkylsulfinyl group; a ($C_1$-$C_6$) alkylsulfonyl group; a halo($C_1$-$C_6$)alkylsulfonyl group; a phenyl group; a substituted phenyl group having 1 to 5 substituents, which may be the same or different, selected from a halogen atom, a ($C_1$-$C_6$)alkyl group, a ($C_2$-$C_6$)alkenyl group, a ($C_2$-$C_6$)alkynyl group, a cyclo($C_3$-$C_6$)alkyl group, a halo ($C_1$-$C_6$)alkyl group, a cyclohalo($C_3$-$C_6$)alkyl group, a ($C_1$-$C_6$)alkoxy group, a halo($C_1$-$C_6$)alkoxy group, a ($C_1$-$C_6$)alkylthio group, a halo($C_1$-$C_6$)alkylthio group, a ($C_1$-$C_6$) alkylsulfinyl group, a halo($C_1$-$C_6$)alkylsulfinyl group, a ($C_1$-$C_6$)alkylsulfonyl group, a halo($C_1$-$C_6$)alkylsulfonyl group, a ($C_1$-$C_6$)alkylcarbonyl group, a halo($C_1$-$C_6$)alkylcarbonyl group, a ($C_1$-$C_6$)alkoxycarbonyl group, a carboxyl group, a mono($C_1$-$C_6$)alkylaminocarbonyl group, a di($C_1$-$C_6$)alkylaminocarbonyl group which may be the same or different, a hydroxyl group or a cyano group; a heterocyclic group which represents a pyridyl group, a pyridine-N-oxide group, a pyrimidinyl group, a pyrazinyl group, a triazinyl group, a furyl group, a tetrahydrofuryl group, a thienyl group, a tetrahydrothienyl group, a tetrahydropyranyl group, a tetrahydrothiopyranyl group, an oxazolyl group, an isooxazolyl group, an oxadiazolyl group, a thiazolyl group, an isothiazolyl group, an thiadiazolyl group, an imidazolyl group, a triazolyl group, a pyrazolyl group, a pyrrolyl group or a pyrrolidinyl group; a substituted heterocyclic group as defined above, having one or more substituents on the ring, which may be the same or different, selected from a halogen atom, a $(C_1-C_6)$alkyl group, a $(C_2-C_6)$alkenyl group, a $(C_2-C_6)$alkynyl group, a cyclo$(C_3-C_6)$alkyl group, a halo$(C_1-C_6)$alkyl group, a cyclohalo$(C_3-C_6)$alkyl group, a $(C_1-C_6)$alkoxy group, a halo$(C_1-C_6)$alkoxy group, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group, a halo$(C_1-C_6)$alkylsulfonyl group, a $(C_1-C_6)$alkylcarbonyl group, a halo$(C_1-C_6)$alkylcarbonyl group, a $(C_1-C_6)$alkoxycarbonyl group, a carboxyl group, a mono$(C_1-C_6)$alkylaminocarbonyl group, di$(C_1-C_6)$alkylaminocarbonyl group which may be the same or different, a hydroxyl group or a cyano group; a phenoxy group; a substituted phenoxy group having 1 to 5 substituents, which may be the same or different, selected from a halogen atom, a $(C_1-C_6)$alkyl group, a $(C_2-C_6)$alkenyl group, a $(C_2-C_6)$alkynyl group, a cyclo$(C_3-C_6)$alkyl group, a halo$(C_1-C_6)$alkyl group, a cyclohalo$(C_3-C_6)$alkyl group, a $(C_1-C_6)$alkoxy group, a halo$(C_1-C_6)$alkoxy group, a $(C_3-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group, a halo$(C_1-C_6)$alkylsulfonyl group, a $(C_1-C_6)$alkylcarbonyl group, a halo$(C_1-C_6)$alkylcarbonyl group, an alkoxycarbonyl group, a carboxyl group, a mono$(C_1-C_6)$alkylaminocarbonyl group, a di$(C_1-C_6)$alkylaminocarbonyl group which may be the same or different, a hydroxyl group or a cyano group; a phenylthio group; a substituted phenylthio group having 1 to 5 substituents, which may be the same or different, selected from a halogen atom, a $(C_1-C_6)$alkyl group, a $(C_2-C_6)$alkenyl group, a $(C_2-C_6)$alkynyl group, a cyclo$(C_3-C_6)$alkyl group, a halo$(C_1-C_6)$alkyl group, a cyclohalo a $(C_3-C_6)$alkyl group, a $(C_3-C_6)$alkoxy group, a halo$(C_1-C_6)$alkoxy group, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group, a halo$(C_1-C_6)$alkylsulfonyl group, a $(C_1-C_6)$alkylcarbonyl group, a halo$(C_1-C_6)$alkylcarbonyl group, a $(C_1-C_6)$alkoxycarbonyl group, a carboxyl group, a mono$(C_1-C_6)$alkylaminocarbonyl group, a di$(C_1-C_6)$alkylaminocarbonyl group which may be the same or different, a hydroxyl group or a cyano group $(C_1-C_6)$; a phenylsulfinyl group; a substituted phenylsulfinyl group having 1 to 5 substituents, which may be the same or different, selected from a halogen atom, a $(C_1-C_6)$alkyl group, a $(C_2-C_6)$alkenyl group, a $(C_2-C_6)$alkynyl group, a cyclo$(C_3-C_6)$alkyl group, a halo$(C_1-C_6)$alkyl group, a cyclohalo$(C_3-C_6)$alkyl group, a $(C_1-C_6)$alkoxy group, a halo$(C_1-C_6)$alkoxy group, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group, a halo$(C_1-C_6)$alkylsulfonyl group, a $(C_1-C_6)$alkylcarbonyl group, a halo$(C_1-C_6)$alkylcarbonyl group, a $(C_1-C_6)$alkoxycarbonyl group, a carboxyl group, a mono$(C_1-C_6)$alkylaminocarbonyl group, a di$(C_1-C_6)$alkylaminocarbonyl group which may be the same or different, a hydroxyl group or a cyano group; a phenylsulfonyl group; substituted phenylsulfonyl having 1 to 5 substituents, which may be the same or different, selected from a halogen atom, a $(C_1-C_6)$alkyl group, a $(C_2-C_6)$alkenyl group, a $(C_2-C_6)$alkynyl group, a cyclo$(C_1-C_6)$alkyl group, a halo$(C_1-C_6)$alkyl group, a cyclohalo$(C_3-C_6)$alkyl group, a $(C_1-C_6)$alkoxy group, a halo$(C_1-C_6)$alkoxy group, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group, a halo$(C_1-C_6)$alkylsulfonyl group, a $(C_1-C_6)$alkylcarbonyl group, a halo$(C_1-C_6)$alkylcarbonyl group, a $(C_1-C_6)$alkoxycarbonyl group, a carboxyl group, a mono$(C_1-C_6)$alkylaminocarbonyl group, a di$(C_1-C_6)$alkylaminocarbonyl group which may be the same or different, a hydroxyl group or a cyano group; a $(C_1-C_6)$alkylcarbonyl group; a halo$(C_1-C_6)$alkylcarbonyl group; a phenylcarbonyl group; a substituted phenylcarbonyl group having 1 to 5 substituents, which may be the same or different, selected from a halogen atom, a $(C_1-C_6)$alkyl group, a $(C_2-C_6)$alkenyl group, a $(C_2-C_6)$alkynyl group, a cyclo$(C_3-C_6)$alkyl group, a halo$(C_1-C_6)$alkyl group, a cyclohalo$(C_3-C_6)$alkyl group, a $(C_1-C_6)$alkoxy group, a halo$(C_1-C_6)$alkoxy group, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group, a halo$(C_1-C_6)$alkylsulfonyl group, a $(C_1-C_6)$alkylcarbonyl group, a halo$(C_1-C_6)$alkylcarbonyl group, a $(C_1-C_6)$alkoxycarbonyl group, a carboxyl group, a mono$(C_1-C_6)$alkylaminocarbonyl group, a di$(C_1-C_6)$alkylaminocarbonyl group which may be the same or different, a hydroxyl group or a cyano group; a $(C_1-C_6)$alkoxycarbonyl group; a carboxyl group; a mono$(C_1-C_6)$alkylaminocarbonyl group; a di$(C_1-C_6)$alkylaminocarbonyl group which may be the same or different; a phenylaminocarbonyl group; a substituted phenylaminocarbonyl group having 1 to 5 substituents on the ring, which may be the same or different, selected from a halogen atom, a $(C_1-C_6)$alkyl group, a $(C_2-C_6)$alkenyl group, a $(C_2-C_6)$alkynyl group, a cyclo$(C_3-C_6)$alkyl group, a halo$(C_1-C_6)$alkyl group, a cyclohalo$(C_3-C_6)$alkyl group, a $(C_1-C_6)$alkoxy group, a halo$(C_1-C_6)$alkoxy group, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group, a halo$(C_1-C_6)$alkylsulfonyl group, a $(C_1-C_6)$alkylcarbonyl group, a halo$(C_1-C_6)$alkylcarbonyl group, a $(C_1-C_6)$alkoxycarbonyl group, a carboxyl group, a mono$(C_1-C_6)$alkylaminocarbonyl group, a di$(C_1-C_6)$alkylaminocarbonyl group which may be the same or different, a hydroxyl group or a cyano group; a phenyl$(C_1-C_6)$alkylaminocarbonyl group; a substituted phenyl$(C_1-C_6)$alkylaminocarbonyl group having 1 to 5 substituents on the ring, which may be the same or different, selected from a halogen atom, a $(C_1-C_6)$alkyl group, a $(C_2-C_6)$alkenyl group, a $(C_2-C_6)$alkynyl group, a cyclo$(C_3-C_6)$alkyl group, a halo$(C_1-C_6)$alkyl group, a cyclohalo$(C_3-C_6)$alkyl group, a $(C_1-C_6)$alkoxy group, a halo$(C_1-C_6)$alkoxy group, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group, a halo$(C_1-C_6)$alkylsulfonyl group, a $(C_1-C_6)$ alkylcarbonyl group, a halo$(C_1-C_6)$ alkylcarbonyl group, a $(C_1-C_6)$alkoxycarbonyl group, a carboxyl group, a mono$(C_1-C_6)$alkylaminocarbonyl group, a di$(C_1-C_6)$alkylaminocarbonyl group which may be the same or different, a hydroxyl group or a cyano group; a hydroxyl group or a cyano group, and Y may be taken together with an adjacent carbon atom on the benzene ring to form a 5- or 6-membered ring through a $(C_1-C_4)$alkylene group which may be the same or different and may be interrupted with one or two hetero atoms selected from an oxygen atom, a sulfur atom, or a nitrogen atom which may be substituted with a hydrogen atom, a $(C_1-C_6)$alkyl group, a $(C_2-C_6)$alkenyl group, a $(C_2-C_6)$alkynyl group or a cyclo $(C_3-C_6)$alkyl group, or a salt thereof, herbicides comprising the same as an active ingredient and methods of using the same.

The present invention provides a haloalkylsulfonanilide derivative which is useful as a herbicide excellent in the characteristics such as wide applicability for a number of weed species including hard-to-control weeds, durability of the effect and excellent crop-weed selectivity, particularly useful as a rice herbicide.

BEST MODE FOR CARRYING OUT THE INVENTION

In the definition of general formula (I) of the haloalkylsulfonanilide derivatives of the present invention, examples of "halogen atom" include a chlorine atom, a bromine atom, an iodine atom or a fluorine atom. Examples of "$(C_1-C_4)$alkylene group" include linear or branched alkylene groups having 1 to 6 carbon atoms such as a methylene group, an ethylene group, a propylene group, a dimethylmethylene group, a tetramethylene group, an isobutylene group, a dimethylethylene group and a hexamethylene group, and examples of "$(C_1-C_6)$alkyl group" include linear or branched alkyl groups having 1 to 6 carbon atoms such as a methyl group, an ethyl group, a normal propyl group, an isopropyl group, a normal butyl group, an isobutyl group, a secondary butyl group, a t-butyl group, a normal pentyl group, a neopentyl group, a normal hexyl group. Examples of "halo$(C_1-C_6)$alkyl group" include linear or branched alkyl groups having 1 to 6 carbon atoms substituted with one or more halogen atoms which may be the same or different, and for example include a trifluoromethyl group, a difluoromethyl group, a perfluoroethyl group, a perfluoroisopropyl group, a chloromethyl group, a bromomethyl group, a 1-bromoethyl group and a 2,3-dibromopropyl group. Examples of "$(C_3-C_6)$cycloalkyl group" include alicyclic alkyl groups or alicyclic alkyl groups substituted with alkyl groups having 3 to 6 carbon atoms such as a cyclopropyl group, a cyclobutyl group, a cyclopentyl group, a cyclohexyl group, a 2-methylcyclopropyl group and a 2-methylcyclopentyl group.

Examples of "$(C_1-C_6)$alkoxy group" include linear or branched alkoxy groups having 1 to 6 carbon atoms such as a methoxy group, an ethoxy group, a normal propoxy group, an isopropoxy group, a normal butoxy group, a secondary butoxy group, a tertiary butoxy group, a normal pentyloxy group, an isopentyloxy group, a neopentyloxy group, a normal hexyloxy group. Examples of "halo$(C_1-C_6)$alkoxy group" include linear or branched alkoxy groups having 1 to 6 carbon atoms substituted with one or more halogen atoms which may be the same or different, and for example include a difluoromethoxy group, a trifluoromethoxy group or a 2,2,2-trifluoroethoxy group. Examples of "$(C_1-C_6)$alkoxycarbonyl group" include linear or branched alkoxycarbonyl groups having 1 to 6 carbon atoms such as a methoxycarbonyl group, an ethoxycarbonyl group, a normal propoxycarbonyl group, an isopropoxycarbonyl group, a normal butoxycarbonyl group and a tertiary butoxycarbonyl group. Examples of "$(C_1-C_6)$alkylthio group" include linear or branched alkylthio groups having 1 to 6 carbon atoms such as a methylthio group, an ethylthio group, a normal propylthio group, an isopropylthio group, a normal butylthio group, a secondary butylthio group, a tertiary butylthio group, a normal pentylthio group, an isopentylthio group and a normal hexylthio group. Examples of "$(C_1-C_6)$alkylsulfinyl group" include linear or branched alkylsulfinyl groups having 1 to 6 carbon atoms such as a methylsulfinyl group, an ethylsulfinyl group, a normal propylsulfinyl group, an isopropylsulfinyl group, a normal butylsulfinyl group, a secondary butylsulfinyl group, a tertiary butylsulfinyl group, a normal pentylsulfinyl group, an isopentylsulfinyl group and a normal hexylsulfinyl group. Examples of "$(C_1-C_6)$alkylsulfonyl group" include linear or branched alkylsulfonyl groups having 1 to 6 carbon atoms such as a methylsulfonyl group, an ethylsulfonyl group, a normal propylsulfonyl group, an isopropylsulfonyl group, a normal butylsulfonyl group, a secondary butylsulfonyl group, a tertiary butylsulfonyl, a normal pentylsulfonyl, isopentylsulfonyl and a normal hexylsulfonyl group. Examples of "heterocyclic$(C_1-C_6)$alkyl group" include groups in which a linear or branched alkyl group having 1 to 6 carbon atoms is linked to a heterocycle.

Examples of "heterocycle group" include pyridine, pyridine-N-oxide, pyrimidine, pyrazine, triazine, furan, tetrahydrofuran, thiophene, tetrahydrothiophene, tetrahydropyran, tetrahydrothiopyran, oxazole, isoxazole, oxadiazole, thiazole, isothiazole, thiadiazole, imidazole, triazole, pyrazole, pyrrol, pyrrolidine, phthalimide or 2,3-dihydro-1,2-benzothiazol-3-one 1,1-dioxide. Examples of "heterocyclic group" include a pyridyl group, a pyridine-N-oxide group, a pyrimidinyl group, a pyrazinyl group, a triazinyl group, a furyl group, a tetrahydrofuryl group, a thienyl group, a tetrahydrothienyl group, a tetrahydropyranyl group, a tetrahydrothiopyranyl group, an oxazolyl group, an isooxazolyl group, an oxadiazolyl group, a thiazolyl group, an isothiazolyl group, an thiadiazolyl group, an imidazolyl group, a triazolyl group, a pyrazolyl group, a pyrrolyl group or a pyrrolidinyl group.

Examples of "$(C_2-C_6)$alkenyl group" include linear or branched alkenyl groups having 1 to 6 carbon atoms such as a vinyl group, a 1-propenyl group, a 2-propenyl group, an isopropenyl group, a 2-methyl-1-propenyl group, a 3-methyl-1-propenyl groups, a 2-methyl-2-propenyl group, a 3-methyl-2-propenyl groups, a 1-butenyl group, a 2-butenyl group, a 3-butenyl groups, a 1-pentenyl group, a 2-pentenyl group, a 2-methyl-2-butenyl group, a 1-hexenyl group and a 2,3-dimethyl-2-butenyl group. Examples of "$(C_2-C_{18})$alkenyl group" include a 1-heptenyl group, a 1-octenyl group, a 1-nonenyl group, a 1-decenyl group and a heptadecenyl group or an octadecenyl group in addition to the above $(C_2-C_6)$alkenyl groups.

Examples of "$(C_2-C_6)$alkynyl group" include linear or branched alkenyl groups having 1 to 6 carbon atoms such as an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a 1-hexynyl group, a 2-hexynyl group, a 3-hexynyl group, a 4-hexynyl group and a 5-hexynyl group. Examples of "$(C_2-C_{18})$alkynyl group" include a 1-heptynyl group, a 1-octynyl group, a 1-nonynyl group, a 1-decynyl group and a heptadecynyl group or an octadecynyl group in addition to the above $(C_2-C_6)$alkynyl groups.

The expression such as "$(C_1-C_6)$", "$(C_3-C_6)$" and "$(C_1-C_{18})$" represents a range of the number of carbon atom in various substituents. Furthermore, the above definition can be shown for groups in which the above substituents are linked, and for example, in the case of "$(C_1-C_6)$alkoxy$(C_1-C_6)$alkyl group", represented is a linear or branched alkoxy group having 1 to 6 carbon atoms linked to a linear or branched alkyl group having 1 to 6 carbon atoms.

Examples of salts of haloalkylsulfonanilide derivatives represented by general formula (I) of the present invention include salts with alkaline metals such as sodium ion and potassium ion and salts with alkaline earth metals such as calcium ion. The salts may be also hydrated.

There are cases that a haloalkylsulfonanilide derivative represented by general formula (I) of the present invention has one or more asymmetric centers in the structural formula thereof, and thus there may be two or more kinds of optical isomers and diastereomers. The present invention encompasses each of the optical isomers and all the mixture in which they are contained at an arbitrary ratio.

Of the haloalkylsulfonanilide derivatives represented by general formula (I) of the present invention, preferred are those having a fluoro($C_1$-$C_6$)alkyl group, more preferably a trifluoromethyl group as $R^1$.

Preferably $R^2$ is a hydrogen atom; a ($C_1$-$C_6$)alkyl group; a ($C_1$-$C_6$)alkoxycarbonyl($C_1$-$C_6$)alkyl group; a ($C_1$-$C_{18}$)alkylcarbonyl group; a halo($C_1$-$C_6$)alkylcarbonyl group; a ($C_1$-$C_{18}$)alkoxycarbonyl group; a halo($C_1$-$C_6$)alkoxycarbonyl group; a ($C_1$-$C_8$)alkoxy($C_1$-$C_6$)alkyl group; a ($C_1$-$C_6$)alkoxy($C_1$-$C_6$)alkoxy($C_1$-$C_6$)alkyl group; a ($C_1$-$C_6$)alkylcarbonyloxy($C_1$-$C_6$)alkyl group; or a ($C_1$-$C_6$)alkoxycarbonyloxy($C_1$-$C_6$)alkyl group; more preferably a hydrogen atom; a ($C_1$-$C_6$)alkyl group; a ($C_1$-$C_{18}$)alkoxycarbonyl group; a halo($C_1$-$C_6$)alkoxycarbonyl group; a ($C_1$-$C_8$)alkoxy($C_1$-$C_6$)alkyl group or a ($C_1$-$C_6$)alkylcarbonyloxy($C_1$-$C_6$)alkyl group.

As $R^3$, $R^4$, $R^5$ and $R^6$, particularly preferred is a hydrogen atom.

Preferably, $R^7$ and $R^8$, which may be the same or different, each represents a hydrogen atom; a halogen atom; a ($C_1$-$C_6$) alkyl group; a ($C_3$-$C_6$)cycloalkyl group; a ($C_1$-$C_6$)alkoxy group; a halo($C_1$-$C_6$)alkyl group; or a ($C_1$-$C_6$)alkoxy($C_1$-$C_6$) alkyl group; and more preferably a hydrogen atom; or a ($C_1$-$C_6$)alkyl group.

Preferably, $R^9$ and $R^{10}$, which may be the same or different, each represents a hydrogen atom; a halogen atom; a ($C_1$-$C_6$) alkyl group; a ($C_3$-$C_6$)cycloalkyl group; a ($C_1$-$C_6$)alkoxy group; a halo($C_1$-$C_6$)alkyl group; a ($C_1$-$C_6$)alkoxy($C_1$-$C_6$) alkyl group; a phenyl($C_1$-$C_6$)alkyl group; a substituted phenyl ($C_1$-$C_6$)alkyl group having 1 to 5 substituents, which may be the same or different, selected from a halogen atom, a ($C_1$-$C_6$)alkyl group, a halo($C_1$-$C_6$)alkyl group, a ($C_1$-$C_6$)alkoxy group or a halo($C_1$-$C_6$)alkoxy group on the ring; a phenyl group; a substituted phenyl group having 1 to 5 substituents, which may be the same or different, selected from a halogen atom, a ($C_1$-$C_6$)alkyl group, a halo($C_1$-$C_6$)alkyl group, a ($C_1$-$C_6$)alkoxy group or a halo($C_1$-$C_6$)alkoxy group on the ring, and particularly preferably a hydrogen atom, a ($C_1$-$C_6$)alkyl group, a ($C_3$-$C_6$)cycloalkyl group, a halo($C_1$-$C_6$)alkyl group, a phenyl group, or a substituted phenyl group having 1 to 5 substituents, which may be the same or different, selected from a halogen atom, a ($C_1$-$C_6$)alkyl group or a ($C_1$-$C_6$) alkoxy group. The case that $R^7$, $R^8$, $R^9$ and $R^{10}$ respectively link to an adjacent substituent to form a 3- to 7-membered ring through a ($C_1$-$C_4$)alkylene group which may be the same or different and may be interrupted with one or two hetero atoms selected from an oxygen atom, a sulfur atom, or a nitrogen atom which may be substituted with a hydrogen atom, a ($C_1$-$C_6$)alkyl group, a ($C_2$-$C_6$)alkenyl group, a ($C_1$-$C_6$)alkynyl group or a cyclo ($C_3$-$C_6$)alkyl group) is also a preferable embodiment and more preferable is the case that $R^7$, $R^8$, $R^9$ and $R^{10}$ respectively link to an adjacent substituent to form a 3- to 7-membered ring through a ($C_3$-$C_4$)alkylene group.

It is particularly preferable that m is 0 (X is not substituted.) It is particularly preferable that n is 1. A and W are particularly preferably oxygen atoms.

Typical production methods of the haloalkylsulfonanilide derivatives of the present invention are schematically shown below but the present invention is not limited to these.

Production Method 1

The haloalkylsulfonanilide derivatives represented by general formula (I) of the present invention can be produced by the following production method,

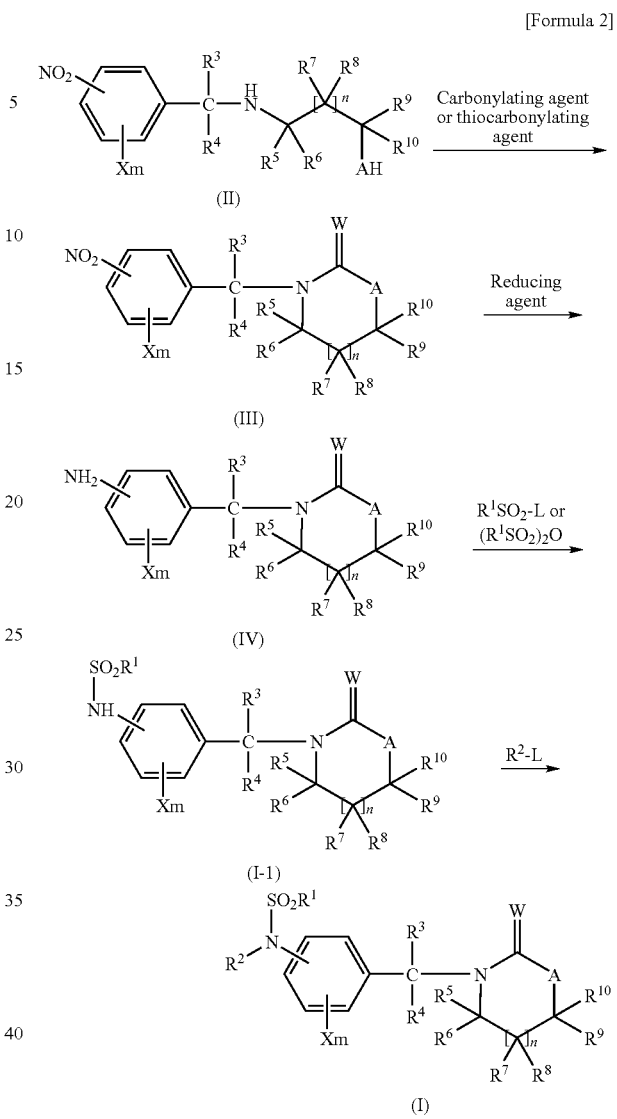

[Formula 2]

wherein $R^1$, $R^2$, $R^3$, $R^4$, $R^5$, $R^6$, $R^7$, $R^8$, $R^9$, $R^{10}$, A, X, W, m and n are the same as above, and L represents a leaving group such as a halogen atom.

The nitro compound represented by general formula (II) can be converted to a cyclic nitro compound represented by general formula (III) by a reaction with a carbonylating agent such as phosgene or a thiocarbonylating agent such as thiophosgene in the presence of or in the absence of an inert solvent. The compound, after isolated or not isolated, can be converted to an aniline derivative represented by general formula (IV) by reducing the nitro group, and haloalkylsulfonanilide derivatives represented by general formula (I-1) (the case that $R^2$ is a hydrogen atom in general formula (I)) which are some kinds of the present invention compounds can be produced by a reaction with a haloalkylsulfonyl derivative represented by $R^1SO_2$-L or ($R^1SO_2$)$_2$O after isolating or not isolating the aniline derivative. Furthermore, haloalkylsulfonanilide derivatives represented by general formula (I) of the present invention can be produced by a reaction with a compound represented by general formula $R^2$-L after isolating or not isolating the haloalkylsulfonanilide derivative represented by general formula (I-1).

1-1) General Formula (II)→General Formula (III)

The inert solvents usable in this reaction are any solvents which do not significantly inhibit the progress of this reaction and examples thereof include inert solvents such as linear or cyclic ethers such as diethyl ether, tetrahydrofuran and dioxane, aromatic hydrocarbons such as benzene, toluene and xylene, halogenated hydrocarbons such as methylene chloride, chloroform and carbon tetrachloride, halogenated aromatic hydrocarbons such as chlorobenzene and dichlorobenzene, and these inert solvents can be used singly or as a mixture of two or more kinds. Examples of usable carbonylating agents usable in this reaction include phosgene, diphosgene, triphosgene, diethyl carbonate and 1,1'-carbonyldiimidazole. Examples of usable thiocarbonylating agents usable in this reaction include thiophosgene and 1,1'-thiocarbonyldiimidazole. The carbonylating agent or thiocarbonylating agent can be used in an amount appropriately selected from the range of about 0.3 to 10 times mol for the nitro compound represented by general formula (II). The bases usable in this reaction can be exemplified by, for example, nitrogen-containing organic bases such as triethylamine, diisopropylethylamine, 1,8-diazabicyclo[5.4.0]-7-undecene and pyridine, inorganic bases such as sodium carbonate, potassium carbonate, sodium hydrogen carbonate, sodium hydroxide, potassium hydroxide, sodium hydride and metallic sodium, organic bases such as potassium acetate and sodium acetate, alcoholates such as sodium ethoxide and potassium t-butoxide. The base can be used in an amount appropriately selected from the range of about 0.5 to 5 times mol for the nitro compound represented by general formula (II). The reaction temperature can be selected from the range of about 0 to 150° C., and the reaction time may vary depending on the reaction scale, reaction temperature, etc. but can be appropriately selected from the range of several minutes to about 48 hours. After the reaction is completed, the target compound is isolated from the reaction mixture containing the target compound by an ordinary method and the target compound can be produced by purifying the compound by recrystallization method, distillation method, column chromatography, etc. as required. The target compound can be also used in the next reaction without isolating the compound after the completion of this reaction.

1-2) General Formula (III)→General Formula (IV)

The inert solvents usable in this reaction can be exemplified by, for example, alcohols such as methanol and ethanol, esters such as tetrahydrofuran and dioxane and water and these inert solvents can be used singly or as a mixture of two or more kinds. The aqueous solution of the acid to be used as a reducing agent shown below can be also used as inert solvent. Reducing agents usable in this reaction can be exemplified by, for example, metal-acid, metal-salt, etc. and examples of metal include iron, tin and zinc, examples of acid include mineral acid such as hydrochloric acid and sulfuric acid, organic acids such as acetic acid, and examples of salt include tin chloride and ammonium chloride. These can be also used in combination. The reducing agent can be used for the metal in an amount appropriately selected from the range of about 1 to 10 times mol and for the acid and salt from the range of about 0.05 to 10 times mol for the cyclic nitro compound represented by general formula (III). The reaction temperature can be selected from the range of about 0 to 150° C., and the reaction time may vary depending on the reaction scale, reaction temperature, etc. but can be appropriately selected from the range of several minutes to about 48 hours. The reducing reaction can be also performed in the presence of a catalyst by catalytic hydrogenation and examples of the catalyst include palladium carbon. After the reaction is completed, the target compound is isolated from the reaction mixture containing the target compound by an ordinary method and the target compound can be produced by purifying the compound by recrystallization method, distillation method, column chromatography, etc. as required. The target compound can be also used in the next reaction without isolating the compound after the completion of this reaction.

1-3) General Formula (IV)→General Formula) (I-1)

The inert solvents usable in this reaction are any solvents which do not significantly inhibit this reaction and examples thereof include inert solvents such as linear or cyclic ethers such as diethyl ether, tetrahydrofuran and dioxane, aromatic hydrocarbons such as benzene, toluene and xylene, halogenated hydrocarbons such as methylene chloride, chloroform and carbon tetrachloride, halogenated aromatic hydrocarbons such as chlorobenzene and dichlorobenzene, nitrites such as acetonitrile, esters such as ethyl acetate, amides such as N,N-dimethylformamide, N,N-dimethylacetamide, dimethylsulfoxide, 1,3-dimethyl-2-imidazolidinone and water, and these inert solvents can be used singly or as a mixture of two or more kinds. The bases usable in this reaction can be exemplified by, for example, nitrogen-containing organic bases such as triethylamine, diisopropylethylamine, 1,8-diazabicyclo [5.4.0]-7-undecene and pyridine, inorganic bases such as sodium carbonate, potassium carbonate, sodium hydrogen carbonate, sodium hydroxide, potassium hydroxide, sodium hydride and metallic sodium, organic bases such as sodium acetate and potassium acetate, alcoholates such as sodium ethoxide and potassium t-butoxide. The base can be used in an amount appropriately selected from the range of about 0.5 to 5 times mol for the aniline derivative represented by general formula (IV). Phase transfer catalysts can be also used for the purpose of accelerating the reaction in this reaction. Phase transfer catalysts usable in this reaction can be exemplified by, for example, quaternary ammonium salts such as tetra-n-buthylammonium bromide, benzyltriethylammonium bromide, and crown ethers such as 18-crown-6. Because this reaction is an equimolar reaction, each reactant can be used in the same mole but some of the reactants can be used excessively. The reaction temperature can be performed in the range of about −20° C. to the reflux temperature of the inert solvent used, and the reaction time may vary depending on the reaction scale, reaction temperature, etc. but can be appropriately selected from the range of several minutes to about 48 hours. After the reaction is completed, the target compound is isolated from the reaction mixture containing the target compound by an ordinary method and the target compound can be produced by purifying the compound by recrystallization method, distillation method, column chromatography, etc. as required. The target compound can be also used in the next reaction without isolating the compound after the completion of this reaction.

1-4) General Formula (I-1)→General Formula (I)

This reaction can be performed following 1-3).

After the reaction is completed, the target compound is isolated from the reaction mixture containing the target compound by an ordinary method and the target compound can be produced by purifying the compound by re-crystallization method, distillation method, column chromatography, etc. as required.

The starting material represented by general formula (II) can be produced following methods described in published documents (for example, Tetrahedron Lett. 31, 4661 (1990), Synth. Commun., 24 (10), 1415 (1994), Bull. Soc. Chim. Fr., 10,347 (1943)) and the methods are described below as methods for producing intermediates.

Method 1 for Producing Intermediates

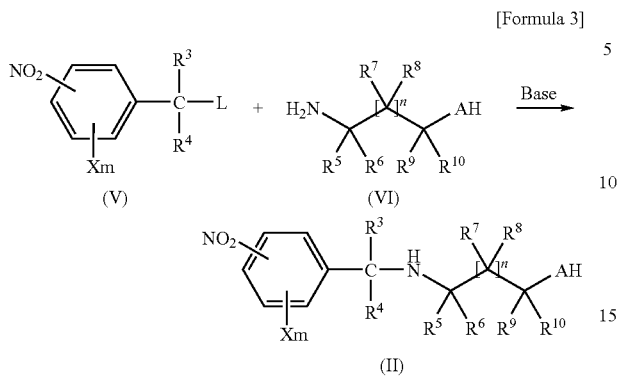

[Formula 3]

(In the formula $R^3$, $R^4$, $R^5$, $R^6$, $R^7$, $R^8$, $R^9$, $R^{10}$, L, A, X, W, m and n are the same as above.

The nitro compound represented by general formula (II) can be produced by reacting a nitrobenzene represented by general formula (V) and an amine represented by general formula (VI) in the presence of or in the absence of a base and an inert solvent.

The inert solvents usable in this reaction are any solvents which do not significantly inhibit the progress of this reaction and examples thereof include inert solvents such as linear or cyclic ethers such as diethyl ether, tetrahydrofuran and dioxane, aromatic hydrocarbons such as benzene, toluene and xylene, amides such as dimethylformamide, N-methylacetamide, N-methylpyrrolidon and hexamethylphosphoroamide, halogenated hydrocarbons such as methylene chloride, chloroform and carbon tetrachloride, halogenated aromatic hydrocarbons such as chlorobenzene and dichlorobenzene, and these inert solvents can be used singly or as a mixture of two or more kinds.

The bases usable in this reaction can be exemplified by, for example, nitrogen-containing organic bases such as triethylamine, diisopropylethylamine, 1,8-diazabicyclo[5.4.0]-7-undecene and pyridine, inorganic bases such as sodium carbonate, potassium carbonate, sodium hydrogen carbonate, sodium hydroxide, potassium hydroxide, sodium hydride and metallic sodium, organic bases such as sodium acetate and potassium acetate, alcoholates such as sodium ethoxide and potassium t-butoxide. The base can be used in an amount appropriately selected from the range of about 0.5 to 5 times mol for the nitrobenzene represented by general formula (V). Because this reaction is an equimolar reaction, each reactant can be used in the same mole but some of the reactants can be used excessively.

The reaction temperature can be selected from the range of about 0 to 150° C., and the reaction time may vary depending on the reaction scale, reaction temperature, etc. but can be appropriately selected from the range of several minutes to about 48 hours. After the reaction is completed, the target compound is isolated from the reaction mixture containing the target compound by an ordinary method and the target compound can be produced by purifying the compound by recrystallization method, distillation method, column chromatography, etc. as required. The target compound can be also used in the next reaction without isolating the compound after the completion of this reaction.

Method 2 for Producing Intermediates

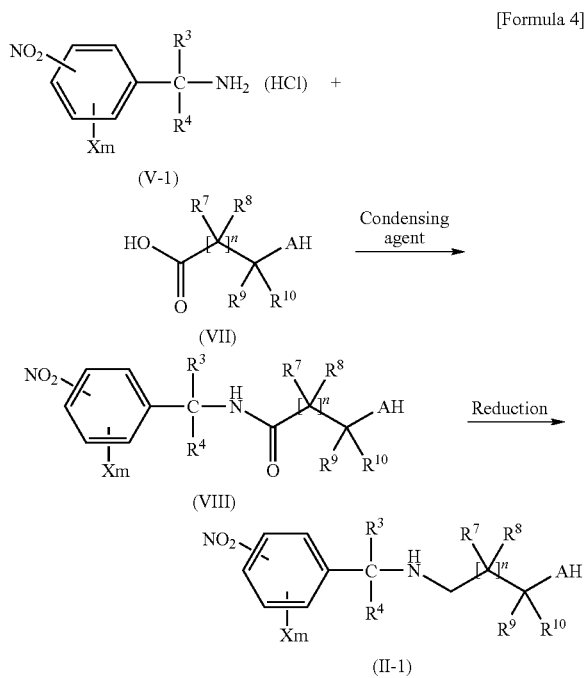

[Formula 4]

wherein $R^3$, $R^4$, $R^7$, $R^8$, $R^9$, $R^{10}$, A, X, W, m and n are the same as above.

The nitro compound represented by general formula (II-1) can be produced by reacting a nitrobenzene represented by general formula (V-1) and a carboxylic acid represented by general formula (VII) in the presence of a condensing agent and in the presence of or in the absence of a base and an inert solvent to form an amide derivative represented by general formula (VIII), and reducing the amide derivative after isolating or not isolating the amide derivative.

2-1) General Formula (V-1) or General Formula (VII)→General Formula (VIII)

The condensing agent to use in this reaction can be exemplified by, for example, diethyl phosphorocyanidate (DEPC), carbonyldiimidazole (CDI), 1,3-dicyclohexylcarbodiimide (DCC), chlorocarbonic ester, 2-chloro-1-methylpyridinium iodide and can be used in an amount appropriately selected from the range of equimolar to excess amount for the nitrobenzene or carboxylic acid represented by general formula (V-1) or general formula (VII).

The bases useful in this reaction include inorganic bases or organic bases and inorganic bases can be exemplified by, for example, hydroxides of alkali metal atoms such as sodium hydroxide and potassium hydroxide, hydrides of alkali metal such as sodium hydride and potassium hydride, alkali metal salts of alcohols such as sodium ethoxide and potassium t-butoxide, carbonates such as sodium carbonate, potassium carbonate and sodium hydrogen carbonate, organic bases can be exemplified by, for example, triethylamine, pyridine and DBU, can be used in an amount appropriately selected from the range of equimolar to excess amount for the nitrobenzene or carboxylic acid represented by general formula (V-1) or general formula (VII).

The inert solvents useful in this reaction are any solvents which do not inhibit the progress of this reaction and, for example, can be exemplified by inert solvents such as aromatic hydrocarbons such as benzene, toluene and xylene, halogenated hydrocarbons such as methylene chloride, chloroform and carbon tetrachloride, halogenated aromatic hydrocarbons such as chlorobenzene and dichlorobenzene, linear or cyclic ethers such as diethyl ether, dioxane and tetrahydrofuran, esters such as ethyl acetate, amides such as dimethylformamide and dimethylacetamide, dimethylsulfoxide, 1,3-dimethyl-2-imidazolidinone, acetone and methyl ethyl ketone and these inert solvents can be used singly or as a mixture of two or more kinds.

Because this reaction is an equimolar reaction, each reactant can be used in the same mole but some of the reactants can be used excessively. The reaction temperature can be performed from room temperature to the boiling temperature range of the inert solvent to use, and the reaction time may vary depending on the reaction scale and reaction temperature but can be performed in the range of several minutes to about 48 hours.

After the reaction is completed, the target compound is isolated from the reaction mixture containing the target compound by an ordinary method and the target compound can be produced by purifying the compound by recrystallization method, distillation method, column chromatography, etc. as required. The target compound can be also used in the next reaction without isolating the compound after the completion of this reaction.

2-2) General Formula (VIII)→General-Formula (II-1)

Examples of the reducing agent usable in this reaction include metal hydride complex compounds such as sodium boron hydride, lithium boron hydride, zinc boron hydride, lithium aluminium hydride, diisobutylaluminum hydride. The reducing agent can be used in an amount appropriately selected from the range of about 0.25 to 10 times mol for the amide derivative represented by general formula (VIII).

The inert solvents usable in this reaction are any solvents which do not significantly inhibit the progress of this reaction and examples thereof include alcohols such as methanol and ethanol, ethers such as tetrahydrofuran and dioxane, halogenated hydrocarbons such as ethylene chloride, chloroform and carbon tetrachloride and water, and these inert solvents can be used singly or as a mixture of two or more kinds. The reaction temperature can be selected from the range of about 0 to 150° C., and the reaction time may vary depending on the reaction scale, reaction temperature, etc. but can be appropriately selected from the range of several minutes to about 48 hours. After the reaction is completed, the target compound is isolated from the reaction mixture containing the target compound by an ordinary method and the target compound can be produced by purifying the compound by recrystallization method, distillation method, column chromatography, etc. as required. The target compound can be also used in the next reaction without isolating the compound after the completion of this reaction.

Method 3 for Producing Intermediates

[Formula 5]

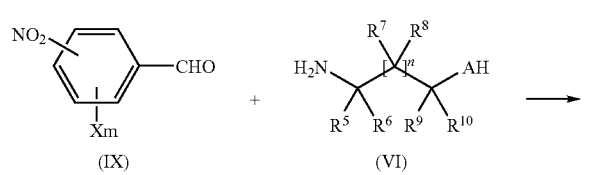

(IX)      (VI)

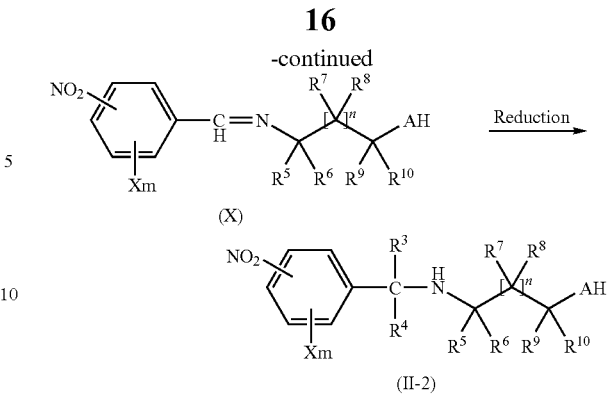

wherein $R^5, R^6, R^7, R^8, R^9, R^{10}, A, X, W, m$ and $n$ are the same as above.

The nitro compound represented by general formula (II-2) can be produced by reacting a benzaldehyde represented by general formula (IX) and an amine represented by general formula (VI) in the presence of an acid catalyst and in the presence of or in the absence of an inert solvent to form an imine derivative represented by general formula (X), and reducing the imine derivative after isolating or not isolating the imine derivative.

3-1) General Formula (IX)→General Formula) (X)

Examples of the acid catalyst usable in this reaction include mineral acids such as hydrochloric acid and sulfuric acid, organic acids such as formic acid, acetic acid and trifluoroacetic acid, and sulfonic acids such as methanesulfonic acid, trifluoromethanesulfonic acid and p-toluenesulfonic acid. The acid catalyst can be used in an amount appropriately selected from the range of about 0.001 to 0.5 time mol for the benzaldehyde represented by general formula (IX).

The inert solvents usable in this reaction are any solvents which do not significantly inhibit the progress of this reaction and examples thereof include inert solvents such as linear or cyclic ethers such as diethyl ether, tetrahydrofuran and dioxane, aromatic hydrocarbons such as benzene, toluene and xylene, halogenated hydrocarbons such as methylene chloride, chloroform and carbon tetrachloride, halogenated aromatic hydrocarbons such as chlorobenzene and dichlorobenzene, and these inert solvents can be used singly or as a mixture of two or more kinds.

The reaction temperature can be selected from the range of about 0 to 150° C., and the reaction time may vary depending on the reaction scale, reaction temperature, etc. but can be appropriately selected from the range of several minutes to about 48 hours. After the reaction is completed, the target compound is isolated from the reaction mixture containing the target compound by an ordinary method and the target compound can be produced by purifying the compound by recrystallization method, distillation method, column chromatography, etc. as required. The target compound can be also used in the next reaction without isolating the compound after the completion of this reaction.

3-2) General Formula (X)→General Formula (II-2)

This reaction can be performed following general reduction methods of imine derivatives (for example, refer to Chemical Society of Japan, "Shin Jikken Kagaku Kouza" ("New Experimental Chemistry Series"), Vol. 15, P. 198 to 199, 1977, Maruzen Co., Ltd.).

Hereinbelow, representative examples of haloalkylsulfonanilide derivatives represented by general formula (I) of the present invention are exemplified in Table 1 and Table 2, and the intermediates thereof are exemplified in Table 3 to Table 6, but the present invention is not limited to these. Also, the $^1$H-NMR data of the compounds having "NMR" in the column of physical property in Table 5 are shown in Table 7. In the Tables, "Me" represents a methyl group, "Et" represents an ethyl group, "Pr" represents a propyl group, "Bu" represents a butyl group, "Pen" represents a pentyl group, "Ph" represents a phenyl group, "n-" represents a normal, "i-" represents an iso, "s-" represents a secondary, "t-" represents a tertiary, "neo-" represents a neo and "c-" represents an alicyclic hydrocarbon group.

The "substituted site" represents a site substituted with a haloalkylsulfonylamino group on the benzene ring in each structural formula and physical properties represents a melting point (° C.) or refractive index $n_D$ (measured at temperature ° C.).

TABLE 1

General Formula (I)

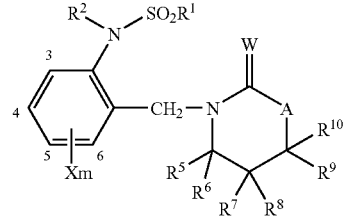

(I-2)

(m = 0, A = O, R$^1$ = CF$_3$, R$^5$ = R$^6$ = H)

| Compound No. | R$^2$ | R$^7$ | R$^8$ | R$^9$ | R$^{10}$ | W | Physical properties |
|---|---|---|---|---|---|---|---|
| 1-1 | H | H | H | H | H | O | 1.4952 (22) |
| 1-2 | CO$_2$Me | H | H | H | H | O | |
| 1-3 | CO$_2$Et | H | H | H | H | O | |
| 1-4 | CO$_2$n-Pr | H | H | H | H | O | 1.4977 (24) |
| 1-5 | CO$_2$n-Bu | H | H | H | H | O | 1.4888 (24) |
| 1-6 | CO$_2$i-Bu | H | H | H | H | O | 1.4875 (22) |
| 1-7 | CO$_2$CH$_2$t-Bu | H | H | H | H | O | |
| 1-8 | Me | H | H | H | H | O | |
| 1-9 | CH$_2$OMe | H | H | H | H | O | |
| 1-10 | CH$_2$OEt | H | H | H | H | O | |
| 1-11 | CH$_2$Oi-Pr | H | H | H | H | O | |
| 1-12 | H | H | H | H | H | S | 113.3-117.2 |
| 1-13 | CO$_2$Me | H | H | H | H | S | 113.3-119.0 |
| 1-14 | CO$_2$Et | H | H | H | H | S | 142.8-144.1 |
| 1-15 | CO$_2$n-Pr | H | H | H | H | S | 74.9-77.4 |
| 1-16 | CO$_2$n-Bu | H | H | H | H | S | 1.5311 (23) |
| 1-17 | CO$_2$i-Bu | H | H | H | H | S | 1.5223 (23) |
| 1-18 | CO$_2$CH$_2$t-Bu | H | H | H | H | S | |
| 1-19 | Me | H | H | H | H | S | |
| 1-20 | CH$_2$OMe | H | H | H | H | S | |
| 1-21 | CH$_2$OEt | H | H | H | H | S | |
| 1-22 | CH$_2$Oi-Pr | H | H | H | H | S | |
| 1-23 | H | Me | Me | H | H | O | 126.5-128.3 |
| 1-24 | CO$_2$Me | Me | Me | H | H | O | |
| 1-25 | CO$_2$Et | Me | Me | H | H | O | 1.4882 (22) |
| 1-26 | CO$_2$n-Pr | Me | Me | H | H | O | 1.4835 (21) |
| 1-27 | CO$_2$n-Bu | Me | Me | H | H | O | 1.4873 (21) |
| 1-28 | CO$_2$i-Bu | Me | Me | H | H | O | 1.4792 (23) |
| 1-29 | CO$_2$CH$_2$t-Bu | Me | Me | H | H | O | |
| 1-30 | Me | Me | Me | H | H | O | |
| 1-31 | CH$_2$OMe | Me | Me | H | H | O | |
| 1-32 | CH$_2$OEt | Me | Me | H | H | O | |
| 1-33 | CH$_2$Oi-Pr | Me | Me | H | H | O | |
| 1-34 | H | Me | Me | H | H | S | 129.9 |
| 1-35 | CO$_2$Me | Me | Me | H | H | S | 1.5295 (26) |
| 1-36 | CO$_2$Et | Me | Me | H | H | S | 1.5223 (26) |
| 1-37 | CO$_2$n-Pr | Me | Me | H | H | S | |
| 1-38 | CO$_2$n-Bu | Me | Me | H | H | S | |
| 1-39 | CO$_2$i-Bu | Me | Me | H | H | S | 1.5159 (26) |
| 1-40 | CO$_2$CH$_2$t-Bu | Me | Me | H | H | S | |
| 1-41 | Me | Me | Me | H | H | S | |
| 1-42 | CH$_2$OMe | Me | Me | H | H | S | |
| 1-43 | CH$_2$OEt | Me | Me | H | H | S | |
| 1-44 | CH$_2$Oi-Pr | Me | Me | H | H | S | |
| 1-45 | H | H | H | Me | Me | O | 1.4985(25) |
| 1-46 | CO$_2$Me | H | H | Me | Me | O | |
| 1-47 | CO$_2$Et | H | H | Me | Me | O | 1.4856 (28) |
| 1-48 | CO$_2$n-Pr | H | H | Me | Me | O | |

TABLE 1-continued

General Formula (I)

(I-2)

$(m = 0, A = O, R^1 = CF_3, R^5 = R^6 = H)$

| Compound No. | $R^2$ | $R^7$ | $R^8$ | $R^9$ | $R^{10}$ | W | Physical properties |
|---|---|---|---|---|---|---|---|
| 1-49 | $CO_2$n-Bu | H | H | Me | Me | O | |
| 1-50 | $CO_2$i-Bu | H | H | Me | Me | O | 1.4860 (28) |
| 1-51 | $CO_2CH_2$t-Bu | H | H | Me | Me | O | 138.4 |
| 1-52 | $CO_2(CH_2)_4$Me | H | H | Me | Me | O | 1.4879(22) |
| 1-53 | $CO_2CH_2$Et(n-Bu) | H | H | Me | Me | O | 96.1-99.5 |
| 1-54 | Me | H | H | Me | Me | O | 1.4949 (26) |
| 1-55 | $CH_2$OMe | H | H | Me | Me | O | 1.4921 (27) |
| 1-56 | $CH_2$OEt | H | H | Me | Me | O | |
| 1-57 | $CH_2$Oi-Pr | H | H | Me | Me | O | |
| 1-58 | H | H | H | Me | Me | S | 136.5-137.1 |
| 1-59 | $CO_2$Me | H | H | Me | Me | S | |
| 1-60 | $CO_2$Et | H | H | Me | Me | S | |
| 1-61 | $CO_2$n-Pr | H | H | Me | Me | S | |
| 1-62 | $CO_2$n-Bu | H | H | Me | Me | S | |
| 1-63 | $CO_2$i-Bu | H | H | Me | Me | S | 1.5130 (26) |
| 1-64 | $CO_2CH_2$t-Bu | H | H | Me | Me | S | 1.5151 (22) |
| 1-65 | Me | H | H | Me | Me | S | |
| 1-66 | $CH_2$OMe | H | H | Me | Me | S | |
| 1-67 | $CH_2$OEt | H | H | Me | Me | S | |
| 1-68 | $CH_2$Oi-Pr | H | H | Me | Me | S | |
| 1-69 | H | H | H | Me | Et | O | 102.9-106.8 |
| 1-70 | $CO_2$Me | H | H | Me | Et | O | |
| 1-71 | $CO_2$Et | H | H | Me | Et | O | 1.4906 (20) |
| 1-72 | $CO_2$n-Pr | H | H | Me | Et | O | |
| 1-73 | $CO_2$n-Bu | H | H | Me | Et | O | |
| 1-74 | $CO_2$i-Bu | H | H | Me | Et | O | 72.0-75.7 |
| 1-75 | $CO_2CH_2$t-Bu | H | H | Me | Et | O | 1.4880 (21) |
| 1-76 | Me | H | H | Me | Et | O | |
| 1-77 | $CH_2$OMe | H | H | Me | Et | O | |
| 1-78 | $CH_2$OEt | H | H | Me | Et | O | |
| 1-79 | $CH_2$Oi-Pr | H | H | Me | Et | O | |
| 1-80 | H | H | H | Me | $CF_3$ | O | 1.4751 (22) |
| 1-81 | $CO_2$Me | H | H | Me | $CF_3$ | O | 103.8-105.1 |
| 1-82 | $CO_2$Et | H | H | Me | $CF_3$ | O | 131.1 |
| 1-83 | $CO_2$n-Pr | H | H | Me | $CF_3$ | O | |
| 1-84 | $CO_2$n-Bu | H | H | Me | $CF_3$ | O | |
| 1-85 | $CO_2$i-Bu | H | H | Me | $CF_3$ | O | 105.5 |
| 1-86 | $CO_2CH_2$t-Bu | H | H | Me | $CF_3$ | O | 39.5 |
| 1-87 | Me | H | H | Me | $CF_3$ | O | |
| 1-88 | $CH_2$OMe | H | H | Me | $CF_3$ | O | |
| 1-89 | $CH_2$OEt | H | H | Me | $CF_3$ | O | |
| 1-90 | $CH_2$Oi-Pr | H | H | Me | $CF_3$ | O | |
| 1-91 | H | H | H | Et | $CF_3$ | O | 106.7 |
| 1-92 | $CO_2$Me | H | H | Et | $CF_3$ | O | 1.4540 (20) |
| 1-93 | $CO_2$Et | H | H | Et | $CF_3$ | O | 75.6-76.2 |
| 1-94 | $CO_2$n-Pr | H | H | Et | $CF_3$ | O | 59.9-60.4 |
| 1-95 | $CO_2$n-Bu | H | H | Et | $CF_3$ | O | 1.4723 (22) |
| 1-96 | $CO_2$i-Bu | H | H | Et | $CF_3$ | O | 1.4700 (24) |
| 1-97 | $CO_2CH_2$t-Bu | H | H | Et | $CF_3$ | O | |
| 1-98 | Me | H | H | Et | $CF_3$ | O | |
| 1-99 | $CH_2$OMe | H | H | Et | $CF_3$ | O | |
| 1-100 | $CH_2$OEt | H | H | Et | $CF_3$ | O | 95.3 |
| 1-101 | $CH_2$Oi-Pr | H | H | Et | $CF_3$ | O | |
| 1-102 | H | H | H | Et | Et | O | 121.9 |
| 1-103 | $CO_2$Me | H | H | Et | Et | O | |
| 1-104 | $CO_2$Et | H | H | Et | Et | O | 1.4892 (22) |
| 1-105 | $CO_2$n-Pr | H | H | Et | Et | O | |
| 1-106 | $CO_2$n-Bu | H | H | Et | Et | O | |
| 1-107 | $CO_2$i-Bu | H | H | Et | Et | O | 1.4871 (22) |
| 1-108 | $CO_2CH_2$t-Bu | H | H | Et | Et | O | 1.4813 (22) |

TABLE 1-continued

General Formula (I)

(I-2)

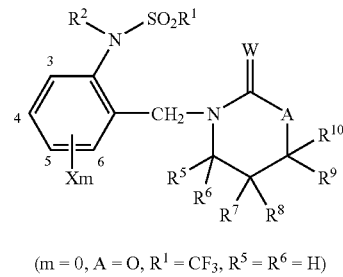

(m = 0, A = O, $R^1$ = $CF_3$, $R^5$ = $R^6$ = H)

| Compound No. | $R^2$ | $R^7$ | $R^8$ | $R^9$ | $R^{10}$ | W | Physical properties |
|---|---|---|---|---|---|---|---|
| 1-109 | $CO_2CH_2Et(n-Bu)$ | H | H | Et | Et | O | 78 |
| 1-110 | Me | H | H | Et | Et | O | |
| 1-111 | $CH_2OMe$ | H | H | Et | Et | O | |
| 1-112 | $CH_2OEt$ | H | H | Et | Et | O | |
| 1-113 | $CH_2Oi-Pr$ | H | H | Et | Et | O | |
| 1-114 | H | H | H | Et | Et | S | 131.8-133.2 |
| 1-115 | $CO_2Me$ | H | H | Et | Et | S | |
| 1-116 | $CO_2Et$ | H | H | Et | Et | S | |
| 1-117 | $CO_2n-Pr$ | H | H | Et | Et | S | |
| 1-118 | $CO_2n-Bu$ | H | H | Et | Et | S | |
| 1-119 | $CO_2i-Bu$ | H | H | Et | Et | S | 1.5081 (22) |
| 1-120 | $CO_2CH_2t-Bu$ | H | H | Et | Et | S | 1.5098 (22) |
| 1-121 | Me | H | H | Et | Et | S | |
| 1-122 | $CH_2OMe$ | H | H | Et | Et | S | |
| 1-123 | $CH_2OEt$ | H | H | Et | Et | S | |
| 1-124 | $CH_2Oi-Pr$ | H | H | Et | Et | S | |
| 1-125 | H | H | H | Me | c-Pr | O | 1.5080 (19) |
| 1-126 | $CO_2Me$ | H | H | Me | c-Pr | O | |
| 1-127 | $CO_2Et$ | H | H | Me | c-Pr | O | |
| 1-128 | $CO_2n-Pr$ | H | H | Me | c-Pr | O | |
| 1-129 | $CO_2n-Bu$ | H | H | Me | c-Pr | O | |
| 1-130 | $CO_2i-Bu$ | H | H | Me | c-Pr | O | 68.5-70.4 |
| 1-131 | $CO_2CH_2t-Bu$ | H | H | Me | c-Pr | O | 1.4939 (24) |
| 1-132 | Me | H | H | Me | c-Pr | O | |
| 1-133 | $CH_2OMe$ | H | H | Me | c-Pr | O | |
| 1-134 | $CH_2OEt$ | H | H | Me | c-Pr | O | |
| 1-135 | $CH_2Oi-Pr$ | H | H | Me | c-Pr | O | |
| 1-136 | $CH_2OC(=O)t-Bu$ | H | H | Me | c-Pr | O | 1.4931 (24) |
| 1-137 | H | H | H | | $(CH_2)_4$ | O | 111.9-113.2 |
| 1-138 | $CO_2Me$ | H | H | | $(CH_2)_4$ | O | |
| 1-139 | $CO_2Et$ | H | H | | $(CH_2)_4$ | O | |
| 1-140 | $CO_2n-Pr$ | H | H | | $(CH_2)_4$ | O | |
| 1-141 | $CO_2n-Bu$ | H | H | | $(CH_2)_4$ | O | |
| 1-142 | $CO_2i-Bu$ | H | H | | $(CH_2)_4$ | O | 83.1 |
| 1-143 | $CO_2CH_2L-Bu$ | H | H | | $(CH_2)_4$ | O | 123.8 |
| 1-144 | $CO_2CH_2Et(n-Bu)$ | H | H | | $(CH_2)_4$ | O | 90.7-92.7 |
| 1-145 | Me | H | H | | $(CH_2)_4$ | O | 141.9 |
| 1-146 | $CH_2OMe$ | H | H | | $(CH_2)_4$ | O | |
| 1-147 | $CH_2OEt$ | H | H | | $(CH_2)_4$ | O | |
| 1-148 | $CH_2Oi-Pr$ | H | H | | $(CH_2)_4$ | O | |
| 1-149 | H | H | H | c-Pr | c-Pr | O | 1.5123 (26) |
| 1-150 | $CO_2Me$ | H | H | c-Pr | c-Pr | O | |
| 1-151 | $CO_2Et$ | H | H | c-Pr | c-Pr | O | |
| 1-152 | $CO_2n-Pr$ | H | H | c-Pr | c-Pr | O | |
| 1-153 | $CO_2n-Bu$ | H | H | c-Pr | c-Pr | O | |
| 1-154 | $CO_2i-Bu$ | H | H | c-Pr | c-Pr | O | 1.4972 (25) |
| 1-155 | $CO_2CH_2t-Bu$ | H | H | c-Pr | c-Pr | O | 1.4970 (25) |
| 1-156 | Me | H | H | c-Pr | c-Pr | O | |
| 1-157 | $CH_2OMe$ | H | H | c-Pr | c-Pr | O | |
| 1-158 | $CH_2OEt$ | H | H | c-Pr | c-Pr | O | |
| 1-159 | $CH_2Oi-Pr$ | H | H | c-Pr | c-Pr | O | |
| 1-160 | H | H | H | Me | Ph | O | 119.1-121.8 |
| 1-161 | $CO_2Me$ | H | H | Me | Ph | O | |
| 1-162 | $CO_2Et$ | H | H | Me | Ph | O | 1.5220 (21) |
| 1-163 | $CO_2n-Pr$ | H | H | Me | Ph | O | |
| 1-164 | $CO_2n-Bu$ | H | H | Me | Ph | O | |
| 1-165 | $CO_2i-Bu$ | H | H | Me | Ph | O | 1.5121 (21) |
| 1-166 | $CO_2CH_2t-Bu$ | H | H | Me | Ph | O | |
| 1-167 | Me | H | H | Me | Ph | O | 41.9-42.1 |
| 1-168 | $CH_2OMe$ | H | H | Me | Ph | O | |

TABLE 1-continued

General Formula (I)

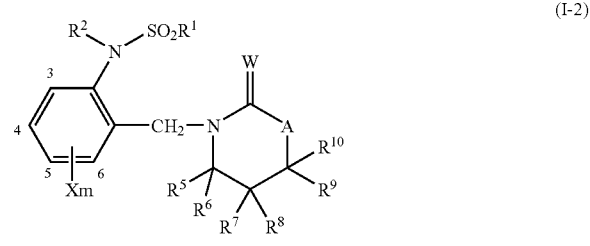

(I-2)

(m = 0, A = O, $R^1$ = $CF_3$, $R^5$ = $R^6$ = H)

| Compound No. | $R^2$ | $R^7$ | $R^8$ | $R^9$ | $R^{10}$ | W | Physical properties |
|---|---|---|---|---|---|---|---|
| 1-169 | $CH_2OEt$ | H | H | Me | Ph | O | |
| 1-170 | $CH_2Oi$-Pr | H | H | Me | Ph | O | |
| 1-171 | $CH_2O(CH_2)_2OMe$ | H | H | Me | Ph | O | 1.5169 (22) |
| 1-172 | H | H | H | Me | 2-Cl-Ph | O | 1.5381 (25) |
| 1-173 | $CO_2Me$ | H | H | Me | 2-Cl-Ph | O | |
| 1-174 | $CO_2Et$ | H | H | Me | 2-Cl-Ph | O | 1.5220 (26) |
| 1-175 | $CO_2n$-Pr | H | H | Me | 2-Cl-Ph | O | |
| 1-176 | $CO_2n$-Bu | H | H | Me | 2-Cl-Ph | O | |
| 1-177 | $CO_2i$-Bu | H | H | Me | 2-Cl-Ph | O | 1.5180 (26) |
| 1-178 | $CO_2CH_2t$-Bu | H | H | Me | 2-Cl-Ph | O | |
| 1-179 | Me | H | H | Me | 2-Cl-Ph | O | |
| 1-180 | $CH_2OMe$ | H | H | Me | 2-Cl-Ph | O | |
| 1-181 | $CH_2OEt$ | H | H | Me | 2-Cl-Ph | O | |
| 1-182 | $CH_2Oi$-Pr | H | H | Me | 2-Cl-Ph | O | |
| 1-183 | H | H | H | c-Pr | Ph | O | 127.5 |
| 1-184 | $CO_2Me$ | H | H | c-Pr | Ph | O | |
| 1-185 | $CO_2Et$ | H | H | c-Pr | Ph | O | 1.5190 (26) |
| 1-186 | $CO_2n$-Pr | H | H | c-Pr | Ph | O | |
| 1-187 | $CO_2n$-Bu | H | H | c-Pr | Ph | O | |
| 1-188 | $CO_2i$-Bu | H | H | c-Pr | Ph | O | 1.5198 (25) |
| 1-189 | $CO_2CH_2t$-Bu | H H | c-Pr | Ph | | O | |
| 1-190 | Me | H | H | c-Pr | Ph | O | |
| 1-191 | $CH_2OMe$ | H | H | c-Pr | Ph | O | 1.5112 (25) |
| 1-192 | $CH_2OEt$ | H | H | c-Pr | Ph | O | |
| 1-193 | $CH_2Oi$-Pr | H | H | c-Pr | Ph | O | |
| 1-194 | $CH_2OCH_2Ph$ | H | H | c-Pr | Ph | O | 1.5389 (24) |
| 1-195 | H | H | H | c-Pr | 4-Cl-Ph | O | 57.6-62.5 |
| 1-196 | $CO_2Me$ | H | H | c-Pr | 4-Cl-Ph | O | |
| 1-197 | $CO_2Et$ | H | H | c-Pr | 4-Cl-Ph | O | 1.5281 (26) |
| 1-198 | $CO_2n$-Pr | H | H | c-Pr | 4-Cl-Ph | O | |
| 1-199 | $CO_2n$-Bu | H | H | c-Pr | 4-Cl-Ph | O | |
| 1-200 | $CO_2i$-Bu | H | H | c-Pr | 4-Cl-Ph | O | |
| 1-201 | $CO_2CH_2t$-Bu | H | H | c-Pr | 4-Cl-Ph | O | |
| 1-202 | Me | H | H | c-Pr | 4-Cl-Ph | O | |
| 1-203 | $CH_2OMe$ | H | H | c-Pr | 4-Cl-Ph | O | |
| 1-204 | $CH_2OEt$ | H | H | c-Pr | 4-cl-Ph | O | |
| 1-205 | $CH_2Oi$-Pr | H | H | c-Pr | 4-Cl-Ph | O | |
| 1-206 | H | H | H | c-Bu | Ph | O | 60.4-64.5 |
| 1-207 | $CO_2Me$ | H | H | c-Bu | Ph | O | |
| 1-208 | $CO_2Et$ | H | H | c-Bu | Ph | O | 1.5193 (25) |
| 1-209 | $CO_2n$-Pr | H | H | c-Bu | Ph | O | |
| 1-210 | $CO_2n$-Bu | H | H | c-Bu | Ph | O | |
| 1-211 | $CO_2i$-Bu | H | H | c-Bu | Ph | O | 44.3-47.8 |
| 1-212 | $CO_2CH_2t$-Bu | H | H | c-Bu | Ph | O | |
| 1-213 | Me | H | H | c-Bu | Ph | O | |
| 1-214 | $CH_2OMe$ | H | H | c-Bu | Ph | O | |
| 1-215 | $CH_2OEt$ | H | H | c-Bu | Ph | O | |
| 1-216 | $CH_2Oi$-Pr | H | H | c-Bu | Ph | O | |
| 1-217 | H | H | H | Ph | Ph | O | 170.5 |
| 1-218 | $CO_2Me$ | H | H | Ph | Ph | O | |
| 1-219 | $CO_2Et$ | H | H | Ph | Ph | O | 1.5415 (27) |
| 1-220 | $CO_2n$-Pr | H | H | Ph | Ph | O | |
| 1-221 | $CO_2n$-Bu | H | H | Ph | Ph | O | |
| 1-222 | $CO_2i$-Bu | H | H | Ph | Ph | O | |
| 1-223 | $CO_2CH_2t$-Bu | H | H | Ph | Ph | O | |
| 1-224 | Me | H | H | Ph | Ph | O | 158.9 |
| 1-225 | $CH_2OMe$ | H | H | Ph | Ph | O | |
| 1-226 | $CH_2OEt$ | H | H | Ph | Ph | O | |
| 1-227 | $CH_2Oi$-Pr | H | H | Ph | Ph | O | |
| 1-228 | H | H | H | $CF_3$ | Ph | O | 185.4 |

TABLE 1-continued

General Formula (I)

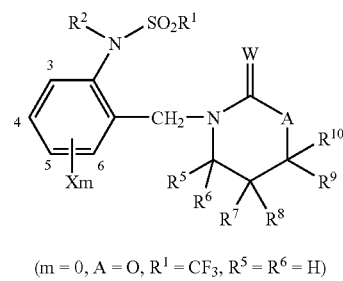

(I-2)

(m = 0, A = O, $R^1$ = $CF_3$, $R^5$ = $R^6$ = H)

| Compound No. | $R^2$ | $R^7$ | $R^8$ | $R^9$ | $R^{10}$ | W | Physical properties |
|---|---|---|---|---|---|---|---|
| 1-229 | $CO_2Me$ | H | H | $CF_3$ | Ph | O | |
| 1-230 | $CO_2Et$ | H | H | $CF_3$ | Ph | O | 1.4909 (26) |
| 1-231 | $CO_2$n-Pr | H | H | $CF_3$ | Ph | O | |
| 1-232 | $CO_2$n-Bu | H | H | $CF_3$ | Ph | O | |
| 1-233 | $CO_2$i-Bu | H | H | $CF_3$ | Ph | O | |
| 1-234 | $CO_2CH_2$t-Bu | H | H | $CF_3$ | Ph | O | |
| 1-235 | Me | H | H | $CF_3$ | Ph | O | |
| 1-236 | $CH_2OMe$ | H | H | $CF_3$ | Ph | O | |
| 1-237 | $CH_2OEt$ | H | H | $CF_3$ | Ph | O | |
| 1-238 | $CH_2O$i-Pr | H | H | $CF_3$ | Ph | O | |
| 1-239 | H | H | H | H | Ph | O | 152 |
| 1-240 | $CO_2Me$ | H | H | H | Ph | O | |
| 1-241 | $CO_2Et$ | H | H | H | Ph | O | 143.9 |
| 1-242 | $CO_2$n-Pr | H | H | H | Ph | O | |
| 1-243 | $CO_2$n-Bu | H | H | H | Ph | O | |
| 1-244 | $CO_2$i-Bu | H | H | H | Ph | O | 163.7 |
| 1-245 | $CO_2CH_2$t-Bu | H | H | H | Ph | O | |
| 1-246 | Me | H | H | H | Ph | O | 153.2 |
| 1-247 | $CH_2OMe$ | H | H | H | Ph | O | |
| 1-248 | $CH_2OEt$ | H | H | H | Ph | O | 115.6 |
| 1-249 | $CH_2O$i-Pr | H | H | H | Ph | O | |
| 1-250 | H | H | H | H | 2-F-Ph | O | 1.5349 (26) |
| 1-251 | $CO_2Me$ | H | H | H | 2-F-Ph | O | |
| 1-252 | $CO_2Et$ | H | H | H | 2-F-Ph | O | 145.5 |
| 1-253 | $CO_2$n-Pr | H | H | H | 2-F-Ph | O | |
| 1-254 | $CO_2$n-Bu | H | H | H | 2-F-Ph | O | |
| 1-255 | $CO_2$i-Bu | H | H | H | 2-F-Ph | O | 169.7 |
| 1-256 | $CO_2CH_2$t-Bu | H | H | H | 2-F-Ph | O | |
| 1-257 | Me | H | H | H | 2-F-Ph | O | 1.5765 (26) |
| 1-258 | $CH_2OMe$ | H | H | H | 2-F-Ph | O | |
| 1-259 | $CH_2OEt$ | H | H | H | 2-F-Ph | O | |
| 1-260 | $CH_2O$i-Pr | H | H | H | 2-F-Ph | O | |
| 1-261 | H | Me | Me | H | Ph | O | 132.9 |
| 1-262 | $CO_2Me$ | Me | Me | H | Ph | O | |
| 1-263 | $CO_2Et$ | Me | Me | H | Ph | O | 1.5119 (23) |
| 1-264 | $CO_2$n-Pr | Me | Me | H | Ph | O | |
| 1-265 | $CO_2$n-Bu | Me | Me | H | Ph | O | |
| 1-266 | $CO_2$i-Bu | Me | Me | H | Ph | O | |
| 1-267 | $CO_2CH_2$t-Bu | Me | Me | H | Ph | O | |
| 1-268 | Me | Me | Me | H | Ph | O | 1.5240(23) |
| 1-269 | $CH_2OMe$ | Me | Me | H | Ph | O | |
| 1-270 | $CH_2OEt$ | Me | Me | H | Ph | O | 1.5092 (23) |
| 1-271 | $CH_2O$i-Pr | Me | Me | H | Ph | O | |
| 1-272 | H | H | H | H | 2,6-$Cl_2$-Ph | O | 1.5386 (20) |
| 1-273 | $CO_2Me$ | H | H | H | 2,6-$Cl_2$-Ph | O | |
| 1-274 | $CO_2Et$ | H | H | H | 2,6-$Cl_2$-Ph | O | 1.5181 (20) |
| 1-275 | $CO_2$n-Pr | H | H | H | 2,6-$Cl_2$-Ph | O | |
| 1-276 | $CO_2$n-Bu | H | H | H | 2,6-$Cl_2$-Ph | O | |
| 1-277 | $CO_2$i-Bu | H | H | H | 2,6-$Cl_2$-Ph | O | |
| 1-278 | $CO_2CH_2$t-Bu | H | H | H | 2,6-$Cl_2$-Ph | O | |
| 1-279 | Me | H | H | H | 2,6-$Cl_2$-Ph | O | 1.5155 (21) |
| 1-280 | $CH_2OMe$ | H | H | H | 2,6-$Cl_2$-Ph | O | |
| 1-281 | $CH_2OEt$ | H | H | H | 2,6-$Cl_2$-Ph | O | 1.5292 (20) |
| 1-282 | $CH_2O$i-Pr | H | H | H | 2,6-$Cl_2$-Ph | O | |
| 1-283 | H | H | H | H | 2-Me-Ph | O | 1.5407 (22) |
| 1-284 | $CO_2Me$ | H | H | H | 2-Me-Ph | O | |
| 1-285 | $CO_2Et$ | H | H | H | 2-Me-Ph | O | 1.5160 (21) |
| 1-286 | $CO_2$n-Pr | H | H | H | 2-Me-Ph | O | |
| 1-287 | $CO_2$n-Bu | H | H | H | 2-Me-Ph | O | |
| 1-288 | $CO_2$i-Bu | H | H | H | 2-Me-Ph | O | |

TABLE 1-continued

General Formula (I)

(I-2)

($m = 0$, $A = O$, $R^1 = CF_3$, $R^5 = R^6 = H$)

| Compound No. | $R^2$ | $R^7$ | $R^8$ | $R^9$ | $R^{10}$ | W | Physical properties |
|---|---|---|---|---|---|---|---|
| 1-289 | $CO_2CH_2$t-Bu | H | H | H | 2-Me-Ph | O | |
| 1-290 | Me | H | H | H | 2-Me-Ph | O | 1.5179 (21) |
| 1-291 | $CH_2OMe$ | H | H | H | 2-Me-Ph | O | |
| 1-292 | $CH_2OEt$ | H | H | H | 2-Me-Ph | O | 1.5235 (21) |
| 1-293 | $CH_2Oi$-Pr | H | H | H | 2-Me-Ph | O | |
| 1-294 | H | H | H | H | 2-$CF_3$-Ph | O | 181.2 |
| 1-295 | $CO_2Me$ | H | H | H | 2-$CF_3$-Ph | O | |
| 1-296 | $CO_2Et$ | H | H | H | 2-$CF_3$-Ph | O | 1.4997 (18) |
| 1-297 | $CO_2$n-Pr | H | H | H | 2-$CF_3$-Ph | O | |
| 1-298 | $CO_2$n-Bu | H | H | H | 2-$CF_3$-Ph | O | |
| 1-299 | $CO_2$i-Bu | H | H | H | 2-$CF_3$-Ph | O | |
| 1-300 | $CO_2CH_2$t-Bu | H | H | H | 2-$CF_3$-Ph | O | |
| 1-301 | Me | H | H | H | 2-$CF_3$-Ph | O | 1.5017 (18) |
| 1-302 | $CH_2OMe$ | H | H | H | 2-$CF_3$-Ph | O | |
| 1-303 | $CH_2OEt$ | H | H | H | 2-$CF_3$-Ph | O | 1.5029 (18) |
| 1-304 | $CH_2Oi$-Pr | H | H | H | 2-$CF_3$-Ph | O | |
| 1-305 | H | H | H | H | 2-Cl-Ph | O | 1.5351 (23) |
| 1-306 | $CO_2Me$ | H | H | H | 2-Cl-Ph | O | |
| 1-307 | $CO_2Et$ | H | H | H | 2-Cl-Ph | O | 133.0-135.5 |
| 1-308 | $CO_2$n-Pr | H | H | H | 2-Cl-Ph | O | |
| 1-309 | $CO_2$n-Bu | H | H | H | 2-Cl-Ph | O | |
| 1-310 | $CO_2$i-Bu | H | H | H | 2-Cl-Ph | O | |
| 1-311 | $CO_2CH_2$t-Bu | H | H | H | 2-Cl-Ph | O | |
| 1-312 | Me | H | H | H | 2-Cl-Ph | O | 1.5256 (22) |
| 1-313 | $CH_2OMe$ | H | H | H | 2-Cl-Ph | O | |
| 1-314 | $CH_2OEt$ | H | H | H | 2-Cl-Ph | O | 1.5263 (22) |
| 1-315 | $CH_2Oi$-Pr | H | H | H | 2-Cl-Ph | O | |
| 1-316 | H | H | H | Et | Ph | O | 120.8-122.4 |
| 1-317 | $CO_2Me$ | H | H | Et | Ph | O | 1.5229 (21) |
| 1-318 | $CO_2Et$ | H | H | Et | Ph | O | 1.5249 (22) |
| 1-319 | $CO_2$n-Pr | H | H | Et | Ph | O | |
| 1-320 | $CO_2$n-Bu | H | H | Et | Ph | O | |
| 1-321 | $CO_2$i-Bu | H | H | Et | Ph | O | 1.5192 (22) |
| 1-322 | $CO_2CH_2$t-Bu | H | H | Et | Ph | O | |
| 1-323 | Me | H | H | Et | Ph | O | 51.0-52.0 |
| 1-324 | $CH_2OMe$ | H | H | Et | Ph | O | |
| 1-325 | $CH_2OEt$ | H | H | Et | Ph | O | |
| 1-326 | $CH_2Oi$-Pr | H | H | Et | Ph | O | |
| 1-327 | H | H | H | Me | t-Bu | O | 156.4 |
| 1-328 | $CO_2Me$ | H | H | Me | t-Bu | O | |
| 1-329 | $CO_2Et$ | H | H | Me | t-Bu | O | 102.2-104.0 |
| 1-330 | $CO_2$n-Pr | H | H | Me | t-Bu | O | |
| 1-331 | $CO_2$n-Bu | H | H | Me | t-Bu | O | |
| 1-332 | $CO_2$i-Bu | H | H | Me | t-Bu | O | 104.2 |
| 1-333 | $CO_2CH_2$t-Bu | H | H | Me | t-Bu | O | |
| 1-334 | Me | H | H | Me | t-Bu | O | |
| 1-335 | $CH_2OMe$ | H | H | Me | t-Bu | O | |
| 1-336 | $CH_2OEt$ | H | H | Me | t-Bu | O | |
| 1-337 | $CH_2Oi$-Pr | H | H | Me | t-Bu | O | |
| 1-338 | H | H | H | $CF_3$ | $CF_3$ | O | 113.7 |
| 1-339 | $CO_2Me$ | H | H | $CF_3$ | $CF_3$ | O | 103.8-105.1 |
| 1-340 | $CO_2Et$ | H | H | $CF_3$ | $CF_3$ | O | 102.4 |
| 1-341 | $CO_2$n-Pr | H | H | $CF_3$ | $CF_3$ | O | |
| 1-342 | $CO_2$n-Bu | H | H | $CF_3$ | $CF_3$ | O | |
| 1-343 | $CO_2$i-Bu | H | H | $CF_3$ | $CF_3$ | O | 1.4542 (22) |
| 1-344 | $CO_2CH_2$t-Bu | H | H | $CF_3$ | $CF_3$ | O | |
| 1-345 | Me | H | H | $CF_3$ | $CF_3$ | O | |
| 1-346 | $CH_2OMe$ | H | H | $CF_3$ | $CF_3$ | O | |
| 1-347 | $CH_2OEt$ | H | H | $CF_3$ | $CF_3$ | O | |
| 1-348 | $CH_2Oi$-Pr | H | H | $CF_3$ | $CF_3$ | O | |

TABLE 1-continued

General Formula (I)

(I-2)

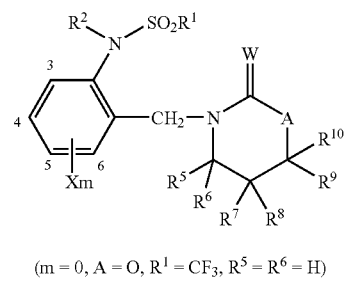

(m = 0, A = O, $R^1$ = $CF_3$, $R^5$ = $R^6$ = H)

| Compound No. | $R^2$ | $R^7$ | $R^8$ | $R^9$ | $R^{10}$ | W | Physical properties |
|---|---|---|---|---|---|---|---|
| 1-349 | H | H | H | H | 2,6-$F_2$-Ph | O | 48.0 |
| 1-350 | $CO_2Me$ | H | H | H | 2,6-$F_2$-Ph | O | 1.4992 (21) |
| 1-351 | $CO_2Et$ | H | H | H | 2,6-$F_2$-Ph | O | 154.0-156.0 |
| 1-352 | $CO_2$n-Pr | H | H | H | 2,6-$F_2$-Ph | O | |
| 1-353 | $CO_2$n-Bu | H | H | H | 2,6-$F_2$-Ph | O | |
| 1-354 | $CO_2$i-Bu | H | H | H | 2,6-$F_2$-Ph | O | |
| 1-355 | $CO_2CH_2$t-Bu | H | H | H | 2,6-$F_2$-Ph | O | |
| 1-356 | Me | H | H | H | 2,6-$F_2$-Ph | O | |
| 1-357 | $CH_2OMe$ | H | H | H | 2,6-$F_2$-Ph | O | |
| 1-358 | $CH_2OEt$ | H | H | H | 2,6-$F_2$-Ph | O | |
| 1-359 | $CH_2Oi$-Pr | H | H | H | 2,6-$F_2$-Ph | O | |
| 1-360 | H | H | H | H | 2,6-$Me_2$-Ph | O | 187.4 |
| 1-361 | $CO_2Me$ | H | H | H | 2,6-$Me_2$-Ph | O | 68.6-72.5 |
| 1-362 | $CO_2Et$ | H | H | H | 2,6-$Me_2$-Ph | O | 1.5252 (22) |
| 1-363 | $CO_2$n-Pr | H | H | H | 2,6-$Me_2$-Ph | O | |
| 1-364 | $CO_2$n-Bu | H | H | H | 2,6-$Me_2$-Ph | O | |
| 1-365 | $CO_2$i-Bu | H | H | H | 2,6-$Me_2$-Ph | O | |
| 1-366 | $CO_2CH_2$t-Bu | H | H | H | 2,6-$Me_2$-Ph | O | |
| 1-367 | Me | H | H | H | 2,6-$Me_2$-Ph | O | |
| 1-368 | $CH_2OMe$ | H | H | H | 2,6-$Me_2$-Ph | O | |
| 1-369 | $CH_2OEt$ | H | H | H | 2,6-$Me_2$-Ph | O | 1.5229 (22) |
| 1-370 | $CH_2Oi$-Pr | H | H | H | 2,6-$Me_2$-Ph | O | |
| 1-371 | H | H | H | Me | 1-Me-1-c-Pr | O | 84.0-86.3 |
| 1-372 | $CO_2Me$ | H | H | Me | 1-Me-1-c-Pr | O | |
| 1-373 | $CO_2Et$ | H | H | Me | 1-Me-1-c-Pr | O | 79.9-81.5 |
| 1-374 | $CO_2$n-Pr | H | H | Me | 1-Me-1-c-Pr | O | |
| 1-375 | $CO_2$n-Bu | H | H | Me | 1-Me-1-c-Pr | O | |
| 1-376 | $CO_2$i-Bu | H | H | Me | 1-Me-1-c-Pr | O | 1.4951 (23) |
| 1-377 | $CO_2CH_2$t-Bu | H | H | Me | 1-Me-1-c-Pr | O | 1.5010 (23) |
| 1-378 | Me | H | H | Me | 1-Me-1-c-Pr | O | |
| 1-379 | $CH_2OMe$ | H | H | Me | 1-Me-1-c-Pr | O | |
| 1-380 | $CH_2OEt$ | H | H | Me | 1-Me-1-c-Pr | O | |
| 1-381 | $CH_2Oi$-Pr | H | H | Me | 1-Me-1-c-Pr | O | |
| 1-382 | H | H | H | Me | c-Bu | O | 136.8-137.2 |
| 1-383 | $CO_2Me$ | H | H | Me | c-Bu | O | |
| 1-384 | $CO_2Et$ | H | H | Me | c-Bu | O | 1.5001 (21) |
| 1-385 | $CO_2$n-Pr | H | H | Me | c-Bu | O | |
| 1-386 | $CO_2$n-Bu | H | H | Me | c-Bu | O | |
| 1-387 | $CO_2$i-Bu | H | H | Me | c-Bu | O | 80.3-81.3 |
| 1-388 | $CO_2CH_2$t-Bu | H | H | Me | c-Bu | O | 94.6-95.8 |
| 1-389 | Me | H | H | Me | c-Bu | O | |
| 1-390 | $CH_2OMe$ | H | H | Me | c-Bu | O | |
| 1-391 | $CH_2OEt$ | H | H | Me | c-Bu | O | |
| 1-392 | $CH_2Oi$-Pr | H | H | Me | c-Bu | O | |
| 1-393 | H | H | H | Me | 2-$CF_3$-Ph | O | 1.4995 (25) |
| 1-394 | $CO_2Me$ | H | H | Me | 2-$CF_3$-Ph | O | 1.5005 (26) |
| 1-395 | $CO_2Et$ | H | H | Me | 2-$CF_3$-Ph | O | 1.4951 (26) |
| 1-396 | $CO_2$n-Pr | H | H | Me | 2-$CF_3$-Ph | O | |
| 1-397 | $CO_2$n-Bu | H | H | Me | 2-$CF_3$-Ph | O | |
| 1-398 | $CO_2$i-Bu | H | H | Me | 2-$CF_3$-Ph | O | |
| 1-399 | $CO_2CH_2$t-Bu | H | H | Me | 2-$CF_3$-Ph | O | |
| 1-400 | Me | H | H | Me | 2-$CF_3$-Ph | O | |
| 1-401 | $CH_2OMe$ | H | H | Me | 2-$CF_3$-Ph | O | |
| 1-402 | $CH_2OEt$ | H | H | Me | 2-$CF_3$-Ph | O | |
| 1-403 | $CH_2Oi$-Pr | H | H | Me | 2-$CF_3$-Ph | O | |
| 1-404 | H | H | H | Me | 2-Me-Ph | O | 1.5123 (24) |
| 1-405 | $CO_2Me$ | H | H | Me | 2-Me-Ph | O | |
| 1-406 | $CO_2Et$ | H | H | Me | 2-Me-Ph | O | 1.5250 (24) |
| 1-407 | $CO_2$n-Pr | H | H | Me | 2-Me-Ph | O | |
| 1-408 | $CO_2$n-Bu | H | H | Me | 2-Me-Ph | O | |

TABLE 1-continued

General Formula (I)

$$(\text{I-2})$$

(m = 0, A = O, $R^1$ = $CF_3$, $R^5$ = $R^6$ = H)

| Compound No. | $R^2$ | $R^7$ | $R^8$ | $R^9$ | $R^{10}$ | W | Physical properties |
|---|---|---|---|---|---|---|---|
| 1-409 | $CO_2$i-Bu | H | H | Me | 2-Me-Ph | O | |
| 1-410 | $CO_2CH_2$t-Bu | H | H | Me | 2-Me-Ph | O | |
| 1-411 | Me | H | H | Me | 2-Me-Ph | O | |
| 1-412 | $CH_2$OMe | H | H | Me | 2-Me-Ph | O | |
| 1-413 | $CH_2$OEt | H | H | Me | 2-Me-Ph | O | |
| 1-414 | $CH_2$Oi-Pr | H | H | Me | 2-Me-Ph | O | |
| 1-415 | $CO_2CH_2CH_2Cl$ | H | H | Et | $CF_3$ | O | 1.4799 (20) |
| 1-416 | $CO_2CH_2CCl_3$ | H | H | Et | $CF_3$ | O | 1.4845 (20) |
| 1-417 | H | H | H | Et | i-Bu | O | 123.8-124.7 |
| 1-418 | $CO_2$Me | H | H | Et | i-Bu | O | |
| 1-419 | $CO_2$Et | H | H | Et | i-Bu | O | 1.4916 (24) |
| 1-420 | $CO_2$n-Pr | H | H | Et | i-Bu | O | |
| 1-421 | $CO_2$n-Bu | H | H | Et | i-Bu | O | |
| 1-422 | $CO_2$i-Bu | H | H | Et | i-Bu | O | 1.4904 (24) |
| 1-423 | $CO_2CH_2$t-Bu | H | H | Et | i-Bu | O | 1.4829 (24) |
| 1-424 | Me | H | H | Et | i-Bu | O | |
| 1-425 | $CH_2$OMe | H | H | Et | i-Bu | O | |
| 1-426 | $CH_2$OEt | H | H | Et | i-Bu | O | |
| 1-427 | $CH_2$Oi-Pr | H | H | Et | i-Bu | O | |
| 1-428 | H | H | H | Me | 2-F-Ph | O | 1.5212 (27) |
| 1-429 | $CO_2$Me | H | H | Me | 2-F-Ph | O | 1.5051 (26) |
| 1-430 | $CO_2$Et | H | H | Me | 2-F-Ph | O | 1.4950 (26) |
| 1-431 | $CO_2$n-Pr | H | H | Me | 2-F-Ph | O | |
| 1-432 | $CO_2$n-Bu | H | H | Me | 2-F-Ph | O | |
| 1-433 | $CO_2$i-Bu | H | H | Me | 2-F-Ph | O | |
| 1-434 | $CO_2CH_2$t-Bu | H | H | Me | 2-F-Ph | O | |
| 1-435 | Me | H | H | Me | 2-F-Ph | O | |
| 1-436 | $CH_2$OMe | H | H | Me | 2-F-Ph | O | |
| 1-437 | $CH_2$OEt | H | H | Me | 2-F-Ph | O | |
| 1-438 | $CH_2$Oi-Pr | H | H | Me | 2-F-Ph | O | |
| 1-439 | H | H | H | Me | 2,6-$F_2$-Ph | O | 1.4982 (27) |
| 1-440 | $CO_2$Me | H | H | Me | 2,6-$F_2$-Ph | O | 1.5005 (25) |
| 1-441 | $CO_2$Et | H | H | Me | 2,6-$F_2$-Ph | O | 1.4871 (25) |
| 1-442 | $CO_2$n-Pr | H | H | Me | 2,6-$F_2$-Ph | O | |
| 1-443 | $CO_2$n-Bu | H | H | Me | 2,6-$F_2$-Ph | O | |
| 1-444 | $CO_2$i-Bu | H | H | Me | 2,6-$F_2$-Ph | O | |
| 1-445 | $CO_2CH_2$t-Bu | H | H | Me | 2,6-$F_2$-Ph | O | |
| 1-446 | Me | H | H | Me | 2,6-$F_2$-Ph | O | |
| 1-447 | $CH_2$OMe | H | H | Me | 2,6-$F_2$-Ph | O | |
| 1-448 | $CH_2$OEt | H | H | Me | 2,6-$F_2$-Ph | O | |
| 1-449 | $CH_2$Oi-Pr | H | H | Me | 2,6-$F_2$-Ph | O | |
| 1-450 | H | H | H | Et | i-Pr | O | 163.7-164.2 |
| 1-451 | $CO_2$Me | H | H | Et | i-Pr | O | |
| 1-452 | $CO_2$Et | H | H | Et | i-Pr | O | 1.4873 (24) |
| 1-453 | $CO_2$n-Pr | H | H | Et | i-Pr | O | |
| 1-454 | $CO_2$n-Bu | H | H | Et | i-Pr | O | |
| 1-455 | $CO_2$i-Bu | H | H | Et | i-Pr | O | 1.4842 (24) |
| 1-456 | $CO_2CH_2$t-Bu | H | H | Et | i-Pr | O | 1.4821 (24) |
| 1-457 | Me | H | H | Et | i-Pr | O | |
| 1-458 | $CH_2$OMe | H | H | Et | i-Pr | O | |
| 1-459 | $CH_2$OEt | H | H | Et | i-Pr | O | |
| 1-460 | $CH_2$Oi-Pr | H | H | Et | i-Pr | O | |
| 1-461 | H | H | H | Me | $CH_2$-2-F-Ph | O | 143.1 |
| 1-462 | $CO_2$Me | H | H | Me | $CH_2$-2-F-Ph | O | |
| 1-463 | $CO_2$Et | H | H | Me | $CH_2$-2-F-Ph | O | 1.4962 (23) |
| 1-464 | $CO_2$n-Pr | H | H | Me | $CH_2$-2-F-Ph | O | |
| 1-465 | $CO_2$n-Bu | H | H | Me | $CH_2$-2-F-Ph | O | |
| 1-466 | $CO_2$i-Bu | H | H | Me | $CH_2$-2-F-Ph | O | |
| 1-467 | $CO_2CH_2$t-Bu | H | H | Me | $CH_2$-2-F-Ph | O | |
| 1-468 | Me | H | H | Me | $CH_2$-2-F-Ph | O | |

TABLE 1-continued

General Formula (I)

(I-2)

(m = 0, A = O, $R^1$ = $CF_3$, $R^5$ = $R^6$ = H)

| Compound No. | $R^2$ | $R^7$ | $R^8$ | $R^9$ | $R^{10}$ | W | Physical properties |
|---|---|---|---|---|---|---|---|
| 1-469 | $CH_2OMe$ | H | H | Me | $CH_2$-2-F-Ph | O | |
| 1-470 | $CH_2OEt$ | H | H | Me | $CH_2$-2-F-Ph | O | |
| 1-471 | $CH_2Oi$-Pr | H | H | Me | $CH_2$-2-F-Ph | O | |
| 1-472 | H | H | H | Me | 4-Cl-Ph | O | 1.5348 (25) |
| 1-473 | $CO_2Me$ | H | H | Me | 4-Cl-Ph | O | 1.5275 (25) |
| 1-474 | $CO_2Et$ | H | H | Me | 4-Cl-Ph | O | 1.5330 (25) |
| 1-475 | $CO_2n$-Pr | H | H | Me | 4-Cl-Ph | O | |
| 1-476 | $CO_2n$-Bu | H | H | Me | 4-Cl-Ph | O | |
| 1-477 | $CO_2i$-Bu | H | H | Me | 4-Cl-Ph | O | |
| 1-478 | $CO_2CH_2t$-Bu | H | H | Me | 4-Cl-Ph | O | |
| 1-479 | Me | H | H | Me | 4-Cl-Ph | O | |
| 1-480 | $CH_2OMe$ | H | H | Me | 4-Cl-Ph | O | |
| 1-481 | $CH_2OEt$ | H | H | Me | 4-Cl-Ph | O | |
| 1-482 | $CH_2Oi$-Pr | H | H | Me | 4-Cl-Ph | O | |
| 1-483 | H | H | H | Me | $CH_2$-2,6-$Cl_2$-Ph | O | 183.6 |
| 1-484 | $CO_2Me$ | H | H | Me | $CH_2$-2,6-$Cl_2$-Ph | O | |
| 1-485 | $CO_2Et$ | H | H | Me | $CH_2$-2,6-$Cl_2$-Ph | O | 1.5270 (25) |
| 1-486 | $CO_2n$-Pr | H | H | Me | $CH_2$-2,6-$Cl_2$-Ph | O | |
| 1-487 | $CO_2n$-Bu | H | H | Me | $CH_2$-2,6-$Cl_2$-Ph | O | |
| 1-488 | $CO_2i$-Bu | H | H | Me | $CH_2$-2,6-$Cl_2$-Ph | O | |
| 1-489 | $CO_2CH_2t$-Bu | H | H | Me | $CH_2$-2,6-$Cl_2$-Ph | O | |
| 1-490 | Me | H | H | Me | $CH_2$-2,6-$Cl_2$-Ph | O | |
| 1-491 | $CH_2OMe$ | H | H | Me | $CH_2$-2,6-$Cl_2$-Ph | O | |
| 1-492 | $CH_2OEt$ | H | H | Me | $CH_2$-2,6-$Cl_2$-Ph | O | |
| 1-493 | $CH_2Oi$-Pr | H | H | Me | $CH_2$-2,6-$Cl_2$-Ph | O | |
| 1-494 | H | H | H | Et | n-Pr | O | 114.1-115.0 |
| 1-495 | $CO_2Me$ | H | H | Et | n-Pr | O | |
| 1-496 | $CO_2Et$ | H | H | Et | n-Pr | O | 1.4905 (25) |
| 1-497 | $CO_2n$-Pr | H | H | Et | n-Pr | O | |
| 1-498 | $CO_2n$-Bu | H | H | Et | n-Pr | O | |
| 1-499 | $CO_2i$-Bu | H | H | Et | n-Pr | O | 1.4840 (25) |
| 1-500 | $CO_2CH_2t$-Bu | H | H | Et | n-Pr | O | |
| 1-501 | $CO_2Ph$ | H | H | Et | n-Pr | O | 1.5069 (25) |
| 1-502 | Me | H | H | Et | n-Pr | O | |
| 1-503 | $CH_2OMe$ | H | H | Et | n-Pr | O | |
| 1-504 | $CH_2OEt$ | H | H | Et | n-Pr | O | |
| 1-505 | $CH_2Oi$-Pr | H | H | Et | n-Pr | O | |
| 1-506 | $CO_2Ph$ | H | H | Me | Me | O | 1.5187 (26) |
| 1-507 | H | H | H | Me | neo-Pen | O | 127.6-129.2 |
| 1-508 | $CO_2Me$ | H | H | Me | neo-Pen | O | |
| 1-509 | $CO_2Et$ | H | H | Me | neo-Pen | O | 1.4820 (25) |
| 1-510 | $CO_2n$-Pr | H | H | Me | neo-Pen | O | |
| 1-511 | $CO_2n$-Bu | H | H | Me | neo-Pen | O | |
| 1-512 | $CO_2i$-Bu | H | H | Me | neo-Pen | O | 90.9-92.6 |
| 1-513 | $CO_2CH_2t$-Bu | H | H | Me | neo-Pen | O | |
| 1-514 | $CO_2Ph$ | H | H | Me | neo-Pen | O | |
| 1-515 | Me | H | H | Me | neo-Pen | O | |
| 1-516 | $CH_2OMe$ | H | H | Me | neo-Pen | O | |
| 1-517 | $CH_2OEt$ | H | H | Me | neo-Pen | O | |
| 1-518 | $CH_2Oi$-Pr | H | H | Me | neo-Pen | O | |
| 1-519 | H | H | H | Me | 3-Cl-Ph | O | 1.5275 (24) |
| 1-520 | $CO_2Me$ | H | H | Me | 3-Cl-Ph | O | 52 |
| 1-521 | $CO_2Et$ | H | H | Me | 3-Cl-Ph | O | 1.5225 (25) |
| 1-522 | $CO_2n$-Pr | H | H | Me | 3-Cl-Ph | O | |
| 1-523 | $CO_2n$-Bu | H | H | Me | 3-Cl-Ph | O | |
| 1-524 | $CO_2i$-Bu | H | H | Me | 3-Cl-Ph | O | |
| 1-525 | $CO_2CH_2t$-Bu | H | H | Me | 3-Cl-Ph | O | |
| 1-526 | $CO_2Ph$ | H | H | Me | 3-Cl-Ph | O | |
| 1-527 | Me | H | H | Me | 3-Cl-Ph | O | |
| 1-528 | $CH_2OMe$ | H | H | Me | 3-Cl-Ph | O | |

TABLE 1-continued

General Formula (I)

(I-2)

$$\text{(m = 0, A = O, R}^1\text{ = CF}_3\text{, R}^5\text{ = R}^6\text{ = H)}$$

| Compound No. | $R^2$ | $R^7$ | $R^8$ | $R^9$ | $R^{10}$ | W | Physical properties |
|---|---|---|---|---|---|---|---|
| 1-529 | $CH_2OEt$ | H | H | Me | 3-Cl-Ph | O | |
| 1-530 | $CH_2Oi$-Pr | H | H | Me | 3-Cl-Ph | O | |
| 1-531 | H | H | H | Me | $CH_2$-2-Cl-Ph | O | 147.0-149.4 |
| 1-532 | $CO_2Me$ | H | H | Me | $CH_2$-2-Cl-Ph | O | |
| 1-533 | $CO_2Et$ | H | H | Me | $CH_2$-2-Cl-Ph | O | 1.5086 (26) |
| 1-534 | $CO_2n$-Pr | H | H | Me | $CH_2$-2-Cl-Ph | O | |
| 1-535 | $CO_2n$-Bu | H | H | Me | $CH_2$-2-Cl-Ph | O | |
| 1-536 | $CO_2i$-Bu | H | H | Me | $CH_2$-2-Cl-Ph | O | |
| 1-537 | $CO_2CH_2t$-Bu | H | H | Me | $CH_2$-2-Cl-Ph | O | |
| 1-538 | $CO_2Ph$ | H | H | Me | $CH_2$-2-Cl-Ph | O | |
| 1-539 | Me | H | H | Me | $CH_2$-2-Cl-Ph | O | |
| 1-540 | $CH_2OMe$ | H | H | Me | $CH_2$-2-Cl-Ph | O | |
| 1-541 | $CH_2OEt$ | H | H | Me | $CH_2$-2-Cl-Ph | O | |
| 1-542 | $CH_2Oi$-Pr | H | H | Me | $CH_2$-2-Cl-Ph | O | |
| 1-543 | H | H | H | Me | $CH_2$-3-Cl-Ph | O | 127.7-131.1 |
| 1-544 | $CO_2Me$ | H | H | Me | $CH_2$-3-Cl-Ph | O | |
| 1-545 | $CO_2Et$ | H | H | Me | $CH_2$-3-Cl-Ph | O | 1.5252 (24) |
| 1-546 | $CO_2n$-Pr | H | H | Me | $CH_2$-3-Cl-Ph | O | |
| 1-547 | $CO_2n$-Bu | H | H | Me | $CH_2$-3-Cl-Ph | O | |
| 1-548 | $CO_2i$-Bu | H | H | Me | $CH_2$-3-Cl-Ph | O | |
| 1-549 | $CO_2CH_2t$-Bu | H | H | Me | $CH_2$-3-Cl-Ph | O | |
| 1-550 | $CO_2Ph$ | H | H | Me | $CH_2$-3-Cl-Ph | O | |
| 1-551 | Me | H | H | Me | $CH_2$-3-Cl-Ph | O | |
| 1-552 | $CH_2OMe$ | H | H | Me | $CH_2$-3-Cl-Ph | O | |
| 1-553 | $CH_2OEt$ | H | H | Me | $CH_2$-3-Cl-Ph | O | |
| 1-554 | $CH_2Oi$-Pr | H | H | Me | $CH_2$-3-Cl-Ph | O | |
| 1-555 | H | H | H | Me | $CH_2$-4-Cl-Ph | O | 125.0-126.8 |
| 1-556 | $CO_2Me$ | H | H | Me | $CH_2$-4-Cl-Ph | O | |
| 1-557 | $CO_2Et$ | H | H | Me | $CH_2$-4-Cl-Ph | O | 1.5166 (24) |
| 1-558 | $CO_2n$-Pr | H | H | Me | $CH_2$-4-Cl-Ph | O | |
| 1-559 | $CO_2n$-Bu | H | H | Me | $CH_2$-4-Cl-Ph | O | |
| 1-560 | $CO_2i$-Bu | H | H | Me | $CH_2$-4-Cl-Ph | O | |
| 1-561 | $CO_2CH_2t$-Bu | H | H | Me | $CH_2$-4-Cl-Ph | O | |
| 1-562 | $CO_2Ph$ | H | H | Me | $CH_2$-4-Cl-Ph | O | |
| 1-563 | Me | H | H | Me | $CH_2$-4-Cl-Ph | O | |
| 1-564 | $CH_2OMe$ | H | H | Me | $CH_2$-4-Cl-Ph | O | |
| 1-565 | $CH_2OEt$ | H | H | Me | $CH_2$-4-Cl-Ph | O | |
| 1-566 | $CH_2Oi$-Pr | H | H | Me | $CH_2$-4-Cl-Ph | O | |
| 1-567 | H | H | H | Me | $CH_2$-3-$CF_3$-Ph | O | 1.5012 (26) |
| 1-568 | $CO_2Me$ | H | H | Me | $CH_2$-3-$CF_3$-Ph | O | |
| 1-569 | $CO_2Et$ | H | H | Me | $CH_2$-3-$CF_3$-Ph | O | 1.4994 (26) |
| 1-570 | $CO_2n$-Pr | H | H | Me | $CH_2$-3-$CF_3$-Ph | O | |
| 1-571 | $CO_2n$-Bu | H | H | Me | $CH_2$-3-$CF_3$-Ph | O | |
| 1-572 | $CO_2i$-Bu | H | H | Me | $CH_2$-3-$CF_3$-Ph | O | |
| 1-573 | $CO_2CH_2t$-Bu | H | H | Me | $CH_2$-3-$CF_3$-Ph | O | |
| 1-574 | $CO_2Ph$ | H | H | Me | $CH_2$-3-$CF_3$-Ph | O | |
| 1-575 | Me | H | H | Me | $CH_2$-3-$CF_3$-Ph | O | |
| 1-576 | $CH_2OMe$ | H | H | Me | $CH_2$-3-$CF_3$-Ph | O | |
| 1-577 | $CH_2OEt$ | H | H | Me | $CH_2$-3-$CF_3$-Ph | O | |
| 1-578 | $CH_2Oi$-Pr | H | H | Me | $CH_2$-3-$CF_3$-Ph | O | |
| 1-579 | H | H | H | Me | $C(CH_2CH_2)$-3-Cl-Ph | O | 190.2-193.0 |
| 1-580 | $CO_2Me$ | H | H | Me | $C(CH_2CH_2)$-3-Cl-Ph | O | |
| 1-581 | $CO_2Et$ | H | H | Me | $C(CH_2CH_2)$-3-Cl-Ph | O | 1.5266 (26) |
| 1-582 | $CO_2n$-Pr | H | H | Me | $C(CH_2CH_2)$-3-Cl-Ph | O | |
| 1-583 | $CO_2n$-Bu | H | H | Me | $C(CH_2CH_2)$-3-Cl-Ph | O | |
| 1-584 | $CO_2i$-Bu | H | H | Me | $C(CH_2CH_2)$-3-Cl-Ph | O | |
| 1-585 | $CO_2CH_2t$-Bu | H | H | Me | $C(CH_2CH_2)$-3-Cl-Ph | O | |
| 1-586 | $CO_2Ph$ | H | H | Me | $C(CH_2CH_2)$-3-Cl-Ph | O | |
| 1-587 | Me | H | H | Me | $C(CH_2CH_2)$-3-Cl-Ph | O | |
| 1-588 | $CH_2OMe$ | H | H | Me | $C(CH_2CH_2)$-3-Cl-Ph | O | |

TABLE 1-continued

General Formula (I)

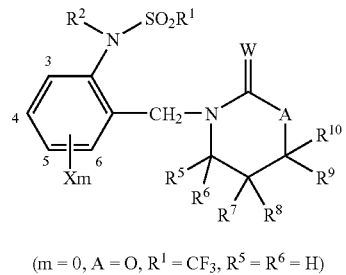

(I-2)

(m = 0, A = O, $R^1$ = $CF_3$, $R^5$ = $R^6$ = H)

| Compound No. | $R^2$ | $R^7$ | $R^8$ | $R^9$ | $R^{10}$ | W | Physical properties |
|---|---|---|---|---|---|---|---|
| 1-589 | $CH_2OEt$ | H | H | Me | $C(CH_2CH_2)$-3-Cl-Ph | O | |
| 1-590 | $CH_2Oi$-Pr | H | H | Me | $C(CH_2CH_2)$-3-Cl-Ph | O | |
| 1-591 | H | H | H | n-Pr | n-Pr | O | 88.1-90.5 |
| 1-592 | $CO_2Me$ | H | H | n-Pr | n-Pr | O | |
| 1-593 | $CO_2Et$ | H | H | n-Pr | n-Pr | O | 1.4778 (24) |
| 1-594 | $CO_2$n-Pr | H | H | n-Pr | n-Pr | O | |
| 1-595 | $CO_2$n-Bu | H | H | n-Pr | n-Pr | O | |
| 1-596 | $CO_2$i-Bu | H | H | n-Pr | n-Pr | O | 1.4804 (24) |
| 1-597 | $CO_2CH_2$t-Bu | H | H | n-Pr | n-Pr | O | |
| 1-598 | $CO_2Ph$ | H | H | n-Pr | n-Pr | O | |
| 1-599 | Me | H | H | n-Pr | n-Pr | O | |
| 1-600 | $CH_2OMe$ | H | H | n-Pr | n-Pr | O | |
| 1-601 | $CH_2OEt$ | H | H | n-Pr | n-Pr | O | |
| 1-602 | $CH_2Oi$-Pr | H | H | n-Pr | n-Pr | O | |
| 1-603 | H | H | H | i-Bu | i-Bu | O | 104.9 |
| 1-604 | $CO_2Me$ | H | H | i-Bu | i-Bu | O | |
| 1-605 | $CO_2Et$ | H | H | i-Bu | i-Bu | O | 1.4829 (24) |
| 1-606 | $CO_2$n-Pr | H | H | i-Bu | i-Bu | O | |
| 1-607 | $CO_2$n-Bu | H | H | i-Bu | i-Bu | O | |
| 1-608 | $CO_2$i-Bu | H | H | i-Bu | i-Bu | O | 1.4846 (24) |
| 1-609 | $CO_2CH_2$t-Bu | H | H | i-Bu | i-Bu | O | |
| 1-610 | $CO_2Ph$ | H | H | i-Bu | i-Bu | O | |
| 1-611 | Me | H | H | i-Bu | i-Bu | O | |
| 1-612 | $CH_2OMe$ | H | H | i-Bu | i-Bu | O | |
| 1-613 | $CH_2OEt$ | H | H | i-Bu | i-Bu | O | |
| 1-614 | $CH_2Oi$-Pr | H | H | i-Bu | i-Bu | O | |
| 1-615 | H | H | H | Me | n-Pr | O | 98.1-102.4 |
| 1-616 | $CO_2Me$ | H | H | Me | n-Pr | O | |
| 1-617 | $CO_2Et$ | H | H | Me | n-Pr | O | 1.4761 (24) |
| 1-618 | $CO_2$n-Pr | H | H | Me | n-Pr | O | |
| 1-619 | $CO_2$n-Bu | H | H | Me | n-Pr | O | |
| 1-620 | $CO_2$i-Bu | H | H | Me | n-Pr | O | 1.4738 (24) |
| 1-621 | $CO_2CH_2$t-Bu | H | H | Me | n-Pr | O | |
| 1-622 | $CO_2Ph$ | H | H | Me | n-Pr | O | |
| 1-623 | Me | H | H | Me | n-Pr | O | |
| 1-624 | $CH_2OMe$ | H | H | Me | n-Pr | O | |
| 1-625 | $CH_2OEt$ | H | H | Me | n-Pr | O | |
| 1-626 | $CH_2Oi$-Pr | H | H | Me | n-Pr | O | |
| 1-627 | H | H | H | Me | n-Bu | O | 105.9-108.2 |
| 1-628 | $CO_2Me$ | H | H | Me | n-Bu | O | |
| 1-629 | $CO_2Et$ | H | H | Me | n-Bu | O | 1.4839 (28) |
| 1-630 | $CO_2$n-Pr | H | H | Me | n-Bu | O | |
| 1-631 | $CO_2$n-Bu | H | H | Me | n-Bu | O | |
| 1-632 | $CO_2$i-Bu | H | H | Me | n-Bu | O | 1.4851 (28) |
| 1-633 | $CO_2CH_2$t-Bu | H | H | Me | n-Bu | O | |
| 1-634 | $CO_2Ph$ | H | H | Me | n-Bu | O | |
| 1-635 | Me | H | H | Me | n-Bu | O | |
| 1-636 | $CH_2OMe$ | H | H | Me | n-Bu | O | |
| 1-637 | $CH_2OEt$ | H | H | Me | n-Bu | O | |
| 1-638 | $CH_2Oi$-Pr | H | H | Me | n-Bu | O | |
| 1-639 | H | H | H | Et | n-Bu | O | 79.5-82.0 |
| 1-640 | $CO_2Me$ | H | H | Et | n-Bu | O | |
| 1-641 | $CO_2Et$ | H | H | Et | n-Bu | O | 1.4831 (26) |
| 1-642 | $CO_2$n-Pr | H | H | Et | n-Bu | O | |
| 1-643 | $CO_2$n-Bu | H | H | Et | n-Bu | O | |
| 1-644 | $CO_2$i-Bu | H | H | Et | n-Bu | O | 1.4746 (26) |
| 1-645 | $CO_2CH_2$t-Bu | H | H | Et | n-Bu | O | |
| 1-646 | $CO_2Ph$ | H | H | Et | n-Bu | O | |
| 1-647 | Me | H | H | Et | n-Bu | O | |
| 1-648 | $CH_2OMe$ | H | H | Et | n-Bu | O | |

TABLE 1-continued

General Formula (I)

(I-2)

(m = 0, A = O, $R^1$ = $CF_3$, $R^5$ = $R^6$ = H)

| Compound No. | $R^2$ | $R^7$ | $R^8$ | $R^9$ | $R^{10}$ | W | Physical properties |
|---|---|---|---|---|---|---|---|
| 1-649 | $CH_2OEt$ | H | H | Et | n-Bu | O | |
| 1-650 | $CH_2Oi$-Pr | H | H | Et | n-Bu | O | |
| 1-651 | H | H | H | n-Bu | n-Bu | O | 89.7-92.4 |
| 1-652 | $CO_2Me$ | H | H | n-Bu | n-Bu | O | |
| 1-653 | $CO_2Et$ | H | H | n-Bu | n-Bu | O | 1.4829 (26) |
| 1-654 | $CO_2$n-Pr | H | H | n-Bu | n-Bu | O | |
| 1-655 | $CO_2$n-Bu | H | H | n-Bu | n-Bu | O | |
| 1-656 | $CO_2$i-Bu | H | H | n-Bu | n-Bu | O | 1.4822 (26) |
| 1-657 | $CO_2CH_2$t-Bu | H | H | n-Bu | n-Bu | O | |
| 1-658 | $CO_2Ph$ | H | H | n-Bu | n-Bu | O | |
| 1-659 | Me | H | H | n-Bu | n-Bu | O | |
| 1-660 | $CH_2OMe$ | H | H | n-Bu | n-Bu | O | |
| 1-661 | $CH_2OEt$ | H | H | n-Bu | n-Bu | O | |
| 1-662 | $CH_2Oi$-Pr | H | H | n-Bu | n-Bu | O | |
| 1-663 | H | H | H | Me | $CH_2CF_3$ | O | 1.4752 (26) |
| 1-664 | $CO_2Me$ | H | H | Me | $CH_2CF_3$ | O | |
| 1-665 | $CO_2Et$ | H | H | Me | $CH_2CF_3$ | O | 1.4642 (26) |
| 1-666 | $CO_2$n-Pr | H | H | Me | $CH_2CF_3$ | O | |
| 1-667 | $CO_2$n-Bu | H | H | Me | $CH_2CF_3$ | O | |
| 1-668 | $CO_2$i-Bu | H | H | Me | $CH_2CF_3$ | O | 1.4669 (26) |
| 1-669 | $CO_2CH_2$t-Bu | H | H | Me | $CH_2CF_3$ | O | |
| 1-670 | $CO_2Ph$ | H | H | Me | $CH_2CF_3$ | O | |
| 1-671 | Me | H | H | Me | $CH_2CF_3$ | O | |
| 1-672 | $CH_2OMe$ | H | H | Me | $CH_2CF_3$ | O | |
| 1-673 | $CH_2OEt$ | H | H | Me | $CH_2CF_3$ | O | |
| 1-674 | $CH_2Oi$-Pr | H | H | Me | $CH_2CF_3$ | O | |
| 1-675 | H | H | H | $CF_3$ | n-Pr | O | |
| 1-676 | $CO_2Me$ | H | H | $CF_3$ | n-Pr | O | |
| 1-677 | $CO_2Et$ | H | H | $CF_3$ | n-Pr | O | |
| 1-678 | $CO_2$n-Pr | H | H | $CF_3$ | n-Pr | O | |
| 1-679 | $CO_2$n-Bu | H | H | $CF_3$ | n-Pr | O | |
| 1-680 | $CO_2$i-Bu | H | H | $CF_3$ | n-Pr | O | |
| 1-681 | $CO_2CH_2$t-Bu | H | H | $CF_3$ | n-Pr | O | |
| 1-682 | $CO_2Ph$ | H | H | $CF_3$ | n-Pr | O | |
| 1-683 | Me | H | H | $CF_3$ | n-Pr | O | |
| 1-684 | $CH_2OMe$ | H | H | $CF_3$ | n-Pr | O | |
| 1-685 | $CH_2OEt$ | H | H | $CF_3$ | n-Pr | O | |
| 1-686 | $CH_2Oi$-Pr | H | H | $CF_3$ | n-Pr | O | |
| 1-687 | H | H | H | $CF_3$ | n-Bu | O | |
| 1-688 | $CO_2Me$ | H | H | $CF_3$ | n-Bu | O | |
| 1-689 | $CO_2Et$ | H | H | $CF_3$ | n-Bu | O | |
| 1-690 | $CO_2$n-Pr | H | H | $CF_3$ | n-Bu | O | |
| 1-691 | $CO_2$n-Bu | H | H | $CF_3$ | n-Bu | O | |
| 1-692 | $CO_2$i-Bu | H | H | $CF_3$ | n-Bu | O | |
| 1-693 | $CO_2CH_2$t-Bu | H | H | $CF_3$ | n-Bu | O | |
| 1-694 | $CO_2Ph$ | H | H | $CF_3$ | n-Bu | O | |
| 1-695 | Me | H | H | $CF_3$ | n-Bu | O | |
| 1-696 | $CH_2OMe$ | H | H | $CF_3$ | n-Bu | O | |
| 1-697 | $CH_2OEt$ | H | H | $CF_3$ | n-Bu | O | |
| 1-698 | $CH_2Oi$-Pr | H | H | $CF_3$ | n-Bu | O | |
| 1-699 | H | H | H | Me | $CH_2$-4-F-Ph | O | 134.4-134.8 |
| 1-700 | $CO_2Me$ | H | H | Me | $CH_2$-4-F-Ph | O | |
| 1-701 | $CO_2Et$ | H | H | Me | $CH_2$-4-F-Ph | O | 1.5018 (27) |
| 1-702 | $CO_2$n-Pr | H | H | Me | $CH_2$-4-F-Ph | O | |
| 1-703 | $CO_2$n-Bu | H | H | Me | $CH_2$-4-F-Ph | O | |
| 1-704 | $CO_2$i-Bu | H | H | Me | $CH_2$-4-F-Ph | O | |
| 1-705 | $CO_2CH_2$t-Bu | H | H | Me | $CH_2$-4-F-Ph | O | |
| 1-706 | $CO_2Ph$ | H | H | Me | $CH_2$-4-F-Ph | O | |
| 1-707 | Me | H | H | Me | $CH_2$-4-F-Ph | O | |
| 1-708 | $CH_2OMe$ | H | H | Me | $CH_2$-4-F-Ph | O | |

TABLE 1-continued

General Formula (I)

(I-2)

(m = 0, A = O, $R^1$ = $CF_3$, $R^5$ = $R^6$ = H)

| Compound No. | $R^2$ | $R^7$ | $R^8$ | $R^9$ | $R^{10}$ | W | Physical properties |
|---|---|---|---|---|---|---|---|
| 1-709 | $CH_2OEt$ | H | H | Me | $CH_2$-4-F-Ph | O | |
| 1-710 | $CH_2Oi$-Pr | H | H | Me | $CH_2$-4-F-Ph | O | |
| 1-711 | H | H | H | Me | 3-F-Ph | O | 116.0-117.0 |
| 1-712 | $CO_2Me$ | H | H | Me | 3-F-Ph | O | 1.5023 (26) |
| 1-713 | $CO_2Et$ | H | H | Me | 3-F-Ph | O | 1.5109 (26) |
| 1-714 | $CO_2n$-Pr | H | H | Me | 3-F-Ph | O | |
| 1-715 | $CO_2n$-Bu | H | H | Me | 3-F-Ph | O | |
| 1-716 | $CO_2i$-Bu | H | H | Me | 3-F-Ph | O | |
| 1-717 | $CO_2CH_2t$-Bu | H | H | Me | 3-F-Ph | O | |
| 1-718 | $CO_2Ph$ | H | H | Me | 3-F-Ph | O | |
| 1-719 | Me | H | H | Me | 3-F-Ph | O | |
| 1-720 | $CH_2OMe$ | H | H | Me | 3-F-Ph | O | |
| 1-721 | $CH_2OEt$ | H | H | Me | 3-F-Ph | O | |
| 1-722 | $CH_2Oi$-Pr | H | H | Me | 3-F-Ph | O | |
| 1-723 | H | H | H | Me | 4-F-Ph | O | 118.5 |
| 1-724 | $CO_2Me$ | H | H | Me | 4-F-Ph | O | 1.5082 (22) |
| 1-725 | $CO_2Et$ | H | H | Me | 4-F-Ph | O | 1.5005 (22) |
| 1-726 | $CO_2n$-Pr | H | H | Me | 4-F-Ph | O | |
| 1-727 | $CO_2n$-Bu | H | H | Me | 4-F-Ph | O | |
| 1-728 | $CO_2i$-Bu | H | H | Me | 4-F-Ph | O | |
| 1-729 | $CO_2CH_2t$-Bu | H | H | Me | 4-F-Ph | O | |
| 1-730 | $CO_2Ph$ | H | H | Me | 4-F-Ph | O | |
| 1-731 | Me | H | H | Me | 4-F-Ph | O | |
| 1-732 | $CH_2OMe$ | H | H | Me | 4-F-Ph | O | |
| 1-733 | $CH_2OEt$ | H | H | Me | 4-F-Ph | O | |
| 1-734 | $CH_2Oi$-Pr | H | H | Me | 4-F-Ph | O | |
| 1-735 | H | H | H | Me | 3,4-$F_2$-Ph | O | 1.5165 (25) |
| 1-736 | $CO_2Me$ | H | H | Me | 3,4-$F_2$-Ph | O | 1.4939 (25) |
| 1-737 | $CO_2Et$ | H | H | Me | 3,4-$F_2$-Ph | O | 1.4950 (26) |
| 1-738 | $CO_2n$-Pr | H | H | Me | 3,4-$F_2$-Ph | O | |
| 1-739 | $CO_2n$-Bu | H | H | Me | 3,4-$F_2$-Ph | O | |
| 1-740 | $CO_2i$-Bu | H | H | Me | 3,4-$F_2$-Ph | O | |
| 1-741 | $CO_2CH_2t$-Bu | H | H | Me | 3,4-$F_2$-Ph | O | |
| 1-742 | $CO_2Ph$ | H | H | Me | 3,4-$F_2$-Ph | O | |
| 1-743 | Me | H | H | Me | 3,4-$F_2$-Ph | O | |
| 1-744 | $CH_2OMe$ | H | H | Me | 3,4-$F_2$-Ph | O | |
| 1-745 | $CH_2OEt$ | H | H | Me | 3,4-$F_2$-Ph | O | |
| 1-746 | $CH_2Oi$-Pr | H | H | Me | 3,4-$F_2$-Ph | O | |
| 1-747 | H | H | H | Me | 3,5-$F_2$-Ph | O | 136.2 |
| 1-748 | $CO_2Me$ | H | H | Me | 3,5-$F_2$-Ph | O | 1.4875 (24) |
| 1-749 | $CO_2Et$ | H | H | Me | 3,5-$F_2$-Ph | O | 1.4962 (24) |
| 1-750 | $CO_2n$-Pr | H | H | Me | 3,5-$F_2$-Ph | O | |
| 1-751 | $CO_2n$-Bu | H | H | Me | 3,5-$F_2$-Ph | O | |
| 1-752 | $CO_2i$-Bu | H | H | Me | 3,5-$F_2$-Ph | O | |
| 1-753 | $CO_2CH_2t$-Bu | H | H | Me | 3,5-$F_2$-Ph | O | |
| 1-754 | $CO_2Ph$ | H | H | Me | 3,5-$F_2$-Ph | O | |
| 1-755 | Me | H | H | Me | 3,5-$F_2$-Ph | O | |
| 1-756 | $CH_2OMe$ | H | H | Me | 3,5-$F_2$-Ph | O | |
| 1-757 | $CH_2OEt$ | H | H | Me | 3,5-$F_2$-Ph | O | |
| 1-758 | $CH_2Oi$-Pr | H | H | Me | 3,5-$F_2$-Ph | O | |
| 1-759 | H | H | H | Me | 3,4-$Cl_2$-Ph | O | |
| 1-760 | $CO_2Me$ | H | H | Me | 3,4-$Cl_2$-Ph | O | |
| 1-761 | $CO_2Et$ | H | H | Me | 3,4-$Cl_2$-Ph | O | |
| 1-762 | $CO_2n$-Pr | H | H | Me | 3,4-$Cl_2$-Ph | O | |
| 1-763 | $CO_2n$-Bu | H | H | Me | 3,4-$Cl_2$-Ph | O | |
| 1-764 | $CO_2i$-Bu | H | H | Me | 3,4-$Cl_2$-Ph | O | |
| 1-765 | $CO_2CH_2t$-Bu | H | H | Me | 3,4-$Cl_2$-Ph | O | |
| 1-766 | $CO_2Ph$ | H | H | Me | 3,4-$Cl_2$-Ph | O | |
| 1-767 | Me | H | H | Me | 3,4-$Cl_2$-Ph | O | |
| 1-768 | $CH_2OMe$ | H | H | Me | 3,4-$Cl_2$-Ph | O | |

TABLE 1-continued

General Formula (I)

(I-2)

(m = 0, A = O, R¹ = CF₃, R⁵ = R⁶ = H)

| Compound No. | R² | R⁷ | R⁸ | R⁹ | R¹⁰ | W | Physical properties |
|---|---|---|---|---|---|---|---|
| 1-769 | CH₂OEt | H | H | Me | 3,4-Cl₂-Ph | O | |
| 1-770 | CH₂Oi-Pr | H | H | Me | 3,4-Cl₂-Ph | O | |
| 1-771 | H | H | H | Me | 3,5-Cl₂-Ph | O | |
| 1-772 | CO₂Me | H | H | Me | 3,5-Cl₂-Ph | O | |
| 1-773 | CO₂Et | H | H | Me | 3,5-Cl₂-Ph | O | |
| 1-774 | CO₂n-Pr | H | H | Me | 3,5-Cl₂-Ph | O | |
| 1-775 | CO₂n-Bu | H | H | Me | 3,5-Cl₂-Ph | O | |
| 1-776 | CO₂i-Bu | H | H | Me | 3,5-Cl₂-Ph | O | |
| 1-777 | CO₂CH₂t-Bu | H | H | Me | 3,5-Cl₂-Ph | O | |
| 1-778 | CO₂Ph | H | H | Me | 3,5-Cl₂-Ph | O | |
| 1-779 | Me | H | H | Me | 3,5-Cl₂-Ph | O | |
| 1-780 | CH₂OMe | H | H | Me | 3,5-Cl₂-Ph | O | |
| 1-781 | CH₂OEt | H | H | Me | 3,5-Cl₂-Ph | O | |
| 1-782 | CH₂Oi-Pr | H | H | Me | 3,5-Cl₂-Ph | O | |
| 1-783 | H | H | H | Et | 3-Cl-Ph | O | |
| 1-784 | CO₂Me | H | H | Et | 3-Cl-Ph | O | |
| 1-785 | CO₂Et | H | H | Et | 3-Cl-Ph | O | |
| 1-786 | CO₂n-Pr | H | H | Et | 3-Cl-Ph | O | |
| 1-787 | CO₂n-Bu | H | H | Et | 3-Cl-Ph | O | |
| 1-788 | CO₂i-Bu | H | H | Et | 3-Cl-Ph | O | |
| 1-789 | CO₂CH₂t-Bu | H | H | Et | 3-Cl-Ph | O | |
| 1-790 | CO₂Ph | H | H | Et | 3-Cl-Ph | O | |
| 1-791 | Me | H | H | Et | 3-Cl-Ph | O | |
| 1-792 | CH₂OMe | H | H | Et | 3-Cl-Ph | O | |
| 1-793 | CH₂OEt | H | H | Et | 3-Cl-Ph | O | |
| 1-794 | CH₂Oi-Pr | H | H | Et | 3-Cl-Ph | O | |
| 1-795 | H | H | H | Et | 4-Cl-Ph | O | |
| 1-796 | CO₂Me | H | H | Et | 4-Cl-Ph | O | |
| 1-797 | CO₂Et | H | H | Et | 4-Cl-Ph | O | |
| 1-798 | CO₂n-Pr | H | H | Et | 4-Cl-Ph | O | |
| 1-799 | CO₂n-Bu | H | H | Et | 4-Cl-Ph | O | |
| 1-800 | CO₂i-Bu | H | H | Et | 4-Cl-Ph | O | |
| 1-801 | CO₂CH₂t-Bu | H | H | Et | 4-Cl-Ph | O | |
| 1-802 | CO₂Ph | H | H | Et | 4-Cl-Ph | O | |
| 1-803 | Me | H | H | Et | 4-Cl-Ph | O | |
| 1-804 | CH₂OMe | H | H | Et | 4-Cl-Ph | O | |
| 1-805 | CH₂OEt | H | H | Et | 4-Cl-Ph | O | |
| 1-806 | CH₂Oi-Pr | H | H | Et | 4-Cl-Ph | O | |
| 1-807 | H | H | H | Et | 3-F-Ph | O | 1.5172 (21) |
| 1-808 | CO₂Me | H | H | Et | 3-F-Ph | O | |
| 1-809 | CO₂Et | H | H | Et | 3-F-Ph | O | |
| 1-810 | CO₂n-Pr | H | H | Et | 3-F-Ph | O | |
| 1-811 | CO₂n-Bu | H | H | Et | 3-F-Ph | O | |
| 1-812 | CO₂i-Bu | H | H | Et | 3-F-Ph | O | |
| 1-813 | CO₂CH₂t-Bu | H | H | Et | 3-F-Ph | O | |
| 1-814 | CO₂Ph | H | H | Et | 3-F-Ph | O | |
| 1-815 | Me | H | H | Et | 3-F-Ph | O | |
| 1-816 | CH₂OMe | H | H | Et | 3-F-Ph | O | |
| 1-817 | CH₂OEt | H | H | Et | 3-F-Ph | O | |
| 1-818 | CH₂Oi-Pr | H | H | Et | 3-F-Ph | O | |
| 1-819 | H | H | H | Et | 4-F-Ph | O | 141.0-142.0 |
| 1-820 | CO₂Me | H | H | Et | 4-F-Ph | O | 1.5150 (27) |
| 1-821 | CO₂Et | H | H | Et | 4-F-Ph | O | 1.4905 (27) |
| 1-822 | CO₂n-Pr | H | H | Et | 4-F-Ph | O | |
| 1-823 | CO₂n-Bu | H | H | Et | 4-F-Ph | O | |
| 1-824 | CO₂i-Bu | H | H | Et | 4-F-Ph | O | |
| 1-825 | CO₂CH₂t-Bu | H | H | Et | 4-F-Ph | O | |
| 1-826 | CO₂Ph | H | H | Et | 4-F-Ph | O | |
| 1-827 | Me | H | H | Et | 4-F-Ph | O | |
| 1-828 | CH₂OMe | H | H | Et | 4-F-Ph | O | |

TABLE 1-continued

General Formula (I)

(I-2)

(m = 0, A = O, R$^1$ = CF$_3$, R$^5$ = R$^6$ = H)

| Compound No. | R$^2$ | R$^7$ | R$^8$ | R$^9$ | R$^{10}$ | W | Physical properties |
|---|---|---|---|---|---|---|---|
| 1-829 | CH$_2$OEt | H | H | Et | 4-F-Ph | O | |
| 1-830 | CH$_2$Oi-Pr | H | H | Et | 4-F-Ph | O | |
| 1-831 | H | H | H | Me | 2-F-6-CF$_3$-Ph | O | 1.5004 (25) |
| 1-832 | CO$_2$Me | H | H | Me | 2-F-6-CF$_3$-Ph | O | 1.4829 (25) |
| 1-833 | CO$_2$Et | H | H | Me | 2-F-6-CF$_3$-Ph | O | |
| 1-834 | CO$_2$n-Pr | H | H | Me | 2-F-6-CF$_3$-Ph | O | |
| 1-835 | CO$_2$n-Bu | H | H | Me | 2-F-6-CF$_3$-Ph | O | |
| 1-836 | CO$_2$i-Bu | H | H | Me | 2-F-6-CF$_3$-Ph | O | |
| 1-837 | CO$_2$CH$_2$t-Bu | H | H | Me | 2-F-6-CF$_3$-Ph | O | |
| 1-838 | CO$_2$Ph | H | H | Me | 2-F-6-CF$_3$-Ph | O | |
| 1-839 | Me | H | H | Me | 2-F-6-CF$_3$-Ph | O | |
| 1-840 | CH$_2$OMe | H | H | Me | 2-F-6-CF$_3$-Ph | O | |
| 1-841 | CH$_2$OEt | H | H | Me | 2-F-6-CF$_3$-Ph | O | |
| 1-842 | CH$_2$Oi-Pr | H | H | Me | 2-F-6-CF$_3$-Ph | O | |
| 1-843 | H | H | H | Me | 2-Br-Ph | O | 1.5350 (27) |
| 1-844 | CO$_2$Me | H | H | Me | 2-Br-Ph | O | 1.5370 (26) |
| 1-845 | CO$_2$Et | H | H | Me | 2-Br-Ph | O | 1.5239 (27) |
| 1-846 | CO$_2$n-Pr | H | H | Me | 2-Br-Ph | O | |
| 1-847 | CO$_2$n-Bu | H | H | Me | 2-Br-Ph | O | |
| 1-848 | CO$_2$i-Bu | H | H | Me | 2-Br-Ph | O | |
| 1-849 | CO$_2$CH$_2$t-Bu | H | H | Me | 2-Br-Ph | O | |
| 1-850 | CO$_2$Ph | H | H | Me | 2-Br-Ph | O | |
| 1-851 | Me | H | H | Me | 2-Br-Ph | O | |
| 1-852 | CH$_2$OMe | H | H | Me | 2-Br-Ph | O | |
| 1-853 | CH$_2$OEt | H | H | Me | 2-Br-Ph | O | |
| 1-854 | CH$_2$Oi-Pr | H | H | Me | 2-Br-Ph | O | |
| 1-855 | H | H | H | Me | 3-Me-Ph | O | 94.1-96.7 |
| 1-856 | CO$_2$Me | H | H | Me | 3-Me-Ph | O | 1.5485 (25) |
| 1-857 | CO$_2$Et | H | H | Me | 3-Me-Ph | O | 1.5402 (25) |
| 1-858 | CO$_2$n-Pr | H | H | Me | 3-Me-Ph | O | |
| 1-859 | CO$_2$n-Bu | H | H | Me | 3-Me-Ph | O | |
| 1-860 | CO$_2$i-Bu | H | H | Me | 3-Me-Ph | O | |
| 1-861 | CO$_2$CH$_2$t-Bu | H | H | Me | 3-Me-Ph | O | |
| 1-862 | CO$_2$Ph | H | H | Me | 3-Me-Ph | O | |
| 1-863 | Me | H | H | Me | 3-Me-Ph | O | |
| 1-864 | CH$_2$OMe | H | H | Me | 3-Me-Ph | O | |
| 1-865 | CH$_2$OEt | H | H | Me | 3-Me-Ph | O | |
| 1-866 | CH$_2$Oi-Pr | H | H | Me | 3-Me-Ph | O | |
| 1-867 | H | H | H | Me | 4-Me-Ph | O | 135.2-137.9 |
| 1-868 | CO$_2$Me | H | H | Me | 4-Me-Ph | O | |
| 1-869 | CO$_2$Et | H | H | Me | 4-Me-Ph | O | 1.5152 (25) |
| 1-870 | CO$_2$n-Pr | H | H | Me | 4-Me-Ph | O | |
| 1-871 | CO$_2$n-Bu | H | H | Me | 4-Me-Ph | O | |
| 1-872 | CO$_2$i-Bu | H | H | Me | 4-Me-Ph | O | 1.5075 (26) |
| 1-873 | CO$_2$CH$_2$t-Bu | H | H | Me | 4-Me-Ph | O | |
| 1-874 | CO$_2$Ph | H | H | Me | 4-Me-Ph | O | |
| 1-875 | Me | H | H | Me | 4-Me-Ph | O | |
| 1-876 | CH$_2$OMe | H | H | Me | 4-Me-Ph | O | |
| 1-877 | CH$_2$OEt | H | H | Me | 4-Me-Ph | O | |
| 1-878 | CH$_2$Oi-Pr | H | H | Me | 4-Me-Ph | O | |
| 1-879 | H | H | H | Me | 3-MeO-Ph | O | 132.9-133.8 |
| 1-880 | CO$_2$Me | H | H | Me | 3-MeO-Ph | O | |
| 1-881 | CO$_2$Et | H | H | Me | 3-MeO-Ph | O | 1.5174 (27) |
| 1-882 | CO$_2$n-Pr | H | H | Me | 3-MeO-Ph | O | |
| 1-883 | CO$_2$n-Bu | H | H | Me | 3-MeO-Ph | O | |
| 1-884 | CO$_2$i-Bu | H | H | Me | 3-MeO-Ph | O | |
| 1-885 | CO$_2$CH$_2$t-Bu | H | H | Me | 3-MeO-Ph | O | |
| 1-886 | CO$_2$Ph | H | H | Me | 3-MeO-Ph | O | |
| 1-887 | Me | H | H | Me | 3-MeO-Ph | O | |
| 1-888 | CH$_2$OMe | H | H | Me | 3-MeO-Ph | O | |

TABLE 1-continued

General Formula (I)

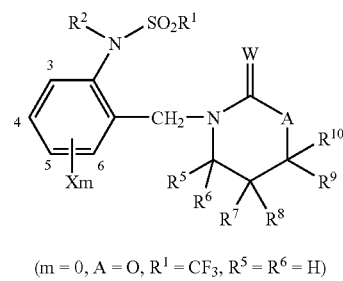

(I-2)

(m = 0, A = O, $R^1$ = $CF_3$, $R^5$ = $R^6$ = H)

| Compound No. | $R^2$ | $R^7$ | $R^8$ | $R^9$ | $R^{10}$ | W | Physical properties |
|---|---|---|---|---|---|---|---|
| 1-889 | $CH_2OEt$ | H | H | Me | 3-MeO-Ph | O | |
| 1-890 | $CH_2Oi$-Pr | H | H | Me | 3-MeO-Ph | O | |
| 1-891 | H | H | H | Me | $CH_2$-3-F-Ph | O | 119.9-122.0 |
| 1-892 | $CO_2Me$ | H | H | Me | $CH_2$-3-F-Ph | O | |
| 1-893 | $CO_2Et$ | H | H | Me | $CH_2$-3-F-Ph | O | 1.5065 (25) |
| 1-894 | $CO_2n$-Pr | H | H | Me | $CH_2$-3-F-Ph | O | |
| 1-895 | $CO_2n$-Bu | H | H | Me | $CH_2$-3-F-Ph | O | |
| 1-896 | $CO_2i$-Bu | H | H | Me | $CH_2$-3-F-Ph | O | |
| 1-897 | $CO_2CH_2t$-Bu | H | H | Me | $CH_2$-3-F-Ph | O | |
| 1-898 | $CO_2Ph$ | H | H | Me | $CH_2$-3-F-Ph | O | |
| 1-899 | Me | H | H | Me | $CH_2$-3-F-Ph | O | |
| 1-900 | $CH_2OMe$ | H | H | Me | $CH_2$-3-F-Ph | O | |
| 1-901 | $CH_2OEt$ | H | H | Me | $CH_2$-3-F-Ph | O | |
| 1-902 | $CH_2Oi$-Pr | H | H | Me | $CH_2$-3-F-Ph | O | |
| 1-903 | H | H | H | Me | $CH_2$-3,4-$F_2$-Ph | O | 109 |
| 1-904 | $CO_2Me$ | H | H | Me | $CH_2$-3,4-$F_2$-Ph | O | |
| 1-905 | $CO_2Et$ | H | H | Me | $CH_2$-3,4-$F_2$-Ph | O | 1.5028 (25) |
| 1-906 | $CO_2n$-Pr | H | H | Me | $CH_2$-3,4-$F_2$-Ph | O | |
| 1-907 | $CO_2n$-Bu | H | H | Me | $CH_2$-3,4-$F_2$-Ph | O | |
| 1-908 | $CO_2i$-Bu | H | H | Me | $CH_2$-3,4-$F_2$-Ph | O | |
| 1-909 | $CO_2CH_2t$-Bu | H | H | Me | $CH_2$-3,4-$F_2$-Ph | O | |
| 1-910 | $CO_2Ph$ | H | H | Me | $CH_2$-3,4-$F_2$-Ph | O | |
| 1-911 | Me | H | H | Me | $CH_2$-3,4-$F_2$-Ph | O | |
| 1-912 | $CH_2OMe$ | H | H | Me | $CH_2$-3,4-$F_2$-Ph | O | |
| 1-913 | $CH_2OEt$ | H | H | Me | $CH_2$-3,4-$F_2$-Ph | O | |
| 1-914 | $CH_2Oi$-Pr | H | H | Me | $CH_2$-3,4-$F_2$-Ph | O | |
| 1-915 | H | H | H | Me | $CH_2$-3-Cl-4-F-Ph | O | 116.6-118.5 |
| 1-916 | $CO_2Me$ | H | H | Me | $CH_2$-3-Cl-4-F-Ph | O | |
| 1-917 | $CO_2Et$ | H | H | Me | $CH_2$-3-Cl-4-F-Ph | O | 1.5162 (25) |
| 1-918 | $CO_2n$-Pr | H | H | Me | $CH_2$-3-Cl-4-F-Ph | O | |
| 1-919 | $CO_2n$-Bu | H | H | Me | $CH_2$-3-Cl-4-F-Ph | O | |
| 1-920 | $CO_2i$-Bu | H | H | Me | $CH_2$-3-Cl-4-F-Ph | O | |
| 1-921 | $CO_2CH_2L$-Bu | H | H | Me | $CH_2$-3-Cl-4-F-Ph | O | |
| 1-922 | $CO_2Ph$ | H | H | Me | $CH_2$-3-Cl-4-F-Ph | O | |
| 1-923 | Me | H | H | Me | $CH_2$-3-Cl-4-F-Ph | O | |
| 1-924 | $CH_2OMe$ | H | H | Me | $CH_2$-3-Cl-4-F-Ph | O | |
| 1-925 | $CH_2OEt$ | H | H | Me | $CH_2$-3-Cl-4-F-Ph | O | |
| 1-926 | $CH_2Oi$-Pr | H | H | Me | $CH_2$-3-Cl-4-F-Ph | O | |
| 1-927 | H | H | H | Me | i-Pr | O | 136.7 |
| 1-928 | $CO_2Me$ | H | H | Me | i-Pr | O | |
| 1-929 | $CO_2Et$ | H | H | Me | i-Pr | O | 69.6-73.8 |
| 1-930 | $CO_2n$-Pr | H | H | Me | i-Pr | O | |
| 1-931 | $CO_2n$-Bu | H | H | Me | i-Pr | O | |
| 1-932 | $CO_2i$-Bu | H | H | Me | i-Pr | O | 94.4-95.7 |
| 1-933 | $CO_2CH_2t$-Bu | H | H | Me | i-Pr | O | |
| 1-934 | $CO_2Ph$ | H | H | Me | i-Pr | O | |
| 1-935 | Me | H | H | Me | i-Pr | O | |
| 1-936 | $CH_2OMe$ | H | H | Me | i-Pr | O | |
| 1-937 | $CH_2OEt$ | H | H | Me | i-Pr | O | |
| 1-938 | $CH_2Oi$-Pr | H | H | Me | i-Pr | O | |
| 1-939 | H | H | H | Me | i-Bu | O | 111.6-112.3 |
| 1-940 | $CO_2Me$ | H | H | Me | i-Bu | O | |
| 1-941 | $CO_2Et$ | H | H | Me | i-Bu | O | 1.4821 (25) |
| 1-942 | $CO_2n$-Pr | H | H | Me | i-Bu | O | |
| 1-943 | $CO_2n$-Bu | H | H | Me | i-Bu | O | |
| 1-944 | $CO_2i$-Bu | H | H | Me | i-Bu | O | 66.9 |
| 1-945 | $CO_2CH_2t$-Bu | H | H | Me | i-Bu | O | |
| 1-946 | $CO_2Ph$ | H | H | Me | i-Bu | O | |
| 1-947 | Me | H | H | Me | i-Bu | O | |
| 1-948 | $CH_2OMe$ | H | H | Me | i-Bu | O | |

TABLE 1-continued

General Formula (I)

$$\text{(I-2)}$$

(m = 0, A = O, $R^1$ = $CF_3$, $R^5$ = $R^6$ = H)

| Compound No. | $R^2$ | $R^7$ | $R^8$ | $R^9$ | $R^{10}$ | W | Physical properties |
|---|---|---|---|---|---|---|---|
| 1-949 | $CH_2OEt$ | H | H | Me | i-Bu | O | |
| 1-950 | $CH_2Oi$-Pr | H | H | Me | i-Bu | O | |
| 1-951 | H | H | H | Me | 2,4-$F_2$-Ph | O | 1.5045 (24) |
| 1-952 | $CO_2Me$ | H | H | Me | 2,4-$F_2$-Ph | O | 1.4917 (25) |
| 1-953 | $CO_2Et$ | H | H | Me | 2,4-$F_2$-Ph | O | 1.4923 (25) |
| 1-954 | $CO_2n$-Pr | H | H | Me | 2,4-$F_2$-Ph | O | |
| 1-955 | $CO_2n$-Bu | H | H | Me | 2,4-$F_2$-Ph | O | |
| 1-956 | $CO_2i$-Bu | H | H | Me | 2,4-$F_2$-Ph | O | |
| 1-957 | $CO_2CH_2t$-Bu | H | H | Me | 2,4-$F_2$-Ph | O | |
| 1-958 | $CO_2Ph$ | H | H | Me | 2,4-$F_2$-Ph | O | |
| 1-959 | Me | H | H | Me | 2,4-$F_2$-Ph | O | |
| 1-960 | $CH_2OMe$ | H | H | Me | 2,4-$F_2$-Ph | O | |
| 1-961 | $CH_2OEt$ | H | H | Me | 2,4-$F_2$-Ph | O | |
| 1-962 | $CH_2Oi$-Pr | H | H | Me | 2,4-$F_2$-Ph | O | |
| 1-963 | H | H | H | Me | $CH_2$-4-MeO-Ph | O | 133.0-133.3 |
| 1-964 | $CO_2Me$ | H | H | Me | $CH_2$-4-MeO-Ph | O | |
| 1-965 | $CO_2Et$ | H | H | Me | $CH_2$-4-MeO-Ph | O | 1.5154 (27) |
| 1-966 | $CO_2n$-Pr | H | H | Me | $CH_2$-4-MeO-Ph | O | |
| 1-967 | $CO_2n$-Bu | H | H | Me | $CH_2$-4-MeO-Ph | O | |
| 1-968 | $CO_2i$-Bu | H | H | Me | $CH_2$-4-MeO-Ph | O | |
| 1-969 | $CO_2CH_2t$-Bu | H | H | Me | $CH_2$-4-MeO-Ph | O | |
| 1-970 | $CO_2Ph$ | H | H | Me | $CH_2$-4-MeO-Ph | O | |
| 1-971 | Me | H | H | Me | $CH_2$-4-MeO-Ph | O | |
| 1-972 | $CH_2OMe$ | H | H | Me | $CH_2$-4-MeO-Ph | O | |
| 1-973 | $CH_2OEt$ | H | H | Me | $CH_2$-4-MeO-Ph | O | |
| 1-974 | $CH_2Oi$-Pr | H | H | Me | $CH_2$-4-MeO-Ph | O | |
| 1-975 | H | H | H | Me | 4-Ph-Ph | O | 64.0-65.0 |
| 1-976 | $CO_2Me$ | H | H | Me | 4-Ph-Ph | O | 1.5411 (24) |
| 1-977 | $CO_2Et$ | H | H | Me | 4-Ph-Ph | O | 1.5468 (24) |
| 1-978 | $CO_2n$-Pr | H | H | Me | 4-Ph-Ph | O | |
| 1-979 | $CO_2n$-Bu | H | H | Me | 4-Ph-Ph | O | |
| 1-980 | $CO_2i$-Bu | H | H | Me | 4-Ph-Ph | O | |
| 1-981 | $CO_2CH_2t$-Bu | H | H | Me | 4-Ph-Ph | O | |
| 1-982 | $CO_2Ph$ | H | H | Me | 4-Ph-Ph | O | |
| 1-983 | Me | H | H | Me | 4-Ph-Ph | O | |
| 1-984 | $CH_2OMe$ | H | H | Me | 4-Ph-Ph | O | |
| 1-985 | $CH_2OEt$ | H | H | Me | 4-Ph-Ph | O | |
| 1-986 | $CH_2Oi$-Pr | H | H | Me | 4-Ph-Ph | O | |
| 1-987 | H | H | H | Me | $CH_2OMe$ | O | 1.5012 (25) |
| 1-988 | $CO_2Me$ | H | H | Me | $CH_2OMe$ | O | |
| 1-989 | $CO_2Et$ | H | H | Me | $CH_2OMe$ | O | 1.4930 (24) |
| 1-990 | $CO_2n$-Pr | H | H | Me | $CH_2OMe$ | O | |
| 1-991 | $CO_2n$-Bu | H | H | Me | $CH_2OMe$ | O | |
| 1-992 | $CO_2i$-Bu | H | H | Me | $CH_2OMe$ | O | 1.4871 (24) |
| 1-993 | $CO_2CH_2t$-Bu | H | H | Me | $CH_2OMe$ | O | 1.4809 (24) |
| 1-994 | $CO_2Ph$ | H | H | Me | $CH_2OMe$ | O | |
| 1-995 | Me | H | H | Me | $CH_2OMe$ | O | |
| 1-996 | $CH_2OMe$ | H | H | Me | $CH_2OMe$ | O | |
| 1-997 | $CH_2OEt$ | H | H | Me | $CH_2OMe$ | O | |
| 1-998 | $CH_2Oi$-Pr | H | H | Me | $CH_2OMe$ | O | |
| 1-999 | H | H | H | Me | $CH_2$-4-Me-Ph | O | 143.7 |
| 1-1000 | $CO_2Me$ | H | H | Me | $CH_2$-4-Me-Ph | O | |
| 1-1001 | $CO_2Et$ | H | H | Me | $CH_2$-4-Me-Ph | O | 1.5172 (26) |
| 1-1002 | $CO_2n$-Pr | H | H | Me | $CH_2$-4-Me-Ph | O | |
| 1-1003 | $CO_2n$-Bu | H | H | Me | $CH_2$-4-Me-Ph | O | |
| 1-1004 | $CO_2i$-Bu | H | H | Me | $CH_2$-4-Me-Ph | O | |
| 1-1005 | $CO_2CH_2t$-Bu | H | H | Me | $CH_2$-4-Me-Ph | O | |
| 1-1006 | $CO_2Ph$ | H | H | Me | $CH_2$-4-Me-Ph | O | |
| 1-1007 | Me | H | H | Me | $CH_2$-4-Me-Ph | O | |
| 1-1008 | $CH_2OMe$ | H | H | Me | $CH_2$-4-Me-Ph | O | |

TABLE 1-continued

General Formula (I)

(I-2)

(m = 0, A = O, $R^1$ = $CF_3$, $R^5$ = $R^6$ = H)

| Compound No. | $R^2$ | $R^7$ | $R^8$ | $R^9$ | $R^{10}$ | W | Physical properties |
|---|---|---|---|---|---|---|---|
| 1-1009 | $CH_2OEt$ | H | H | Me | $CH_2$-4-Me-Ph | O | |
| 1-1010 | $CH_2Oi$-Pr | H | H | Me | $CH_2$-4-Me-Ph | O | |
| 1-1011 | H | H | H | Me | 2-MeO-Ph | O | 147.1-147.7 |
| 1-1012 | $CO_2Me$ | H | H | Me | 2-MeO-Ph | O | |
| 1-1013 | $CO_2Et$ | H | H | Me | 2-MeO-Ph | O | 152.8-153.6 |
| 1-1014 | $CO_2n$-Pr | H | H | Me | 2-MeO-Ph | O | |
| 1-1015 | $CO_2n$-Bu | H | H | Me | 2-MeO-Ph | O | |
| 1-1016 | $CO_2i$-Bu | H | H | Me | 2-MeO-Ph | O | |
| 1-1017 | $CO_2CH_2t$-Bu | H | H | Me | 2-MeO-Ph | O | |
| 1-1018 | $CO_2Ph$ | H | H | Me | 2-MeO-Ph | O | |
| 1-1019 | Me | H | H | Me | 2-MeO-Ph | O | |
| 1-1020 | $CH_2OMe$ | H | H | Me | 2-MeO-Ph | O | |
| 1-1021 | $CH_2OEt$ | H | H | Me | 2-MeO-Ph | O | |
| 1-1022 | $CH_2Oi$-Pr | H | H | Me | 2-MeO-Ph | O | |
| 1-1023 | H | H | H | Me | 2,4-$Cl_2$-Ph | O | 1.5286 (21) |
| 1-1024 | $CO_2Me$ | H | H | Me | 2,4-$Cl_2$-Ph | O | 1.5145 (22) |
| 1-1025 | $CO_2Et$ | H | H | Me | 2,4-$Cl_2$-Ph | O | 1.5228 (22) |
| 1-1026 | $CO_2n$-Pr | H | H | Me | 2,4-$Cl_2$-Ph | O | |
| 1-1027 | $CO_2n$-Bu | H | H | Me | 2,4-$Cl_2$-Ph | O | |
| 1-1028 | $CO_2i$-Bu | H | H | Me | 2,4-$Cl_2$-Ph | O | |
| 1-1029 | $CO_2CH_2t$-Bu | H | H | Me | 2,4-$Cl_2$-Ph | O | |
| 1-1030 | $CO_2Ph$ | H | H | Me | 2,4-$Cl_2$-Ph | O | |
| 1-1031 | Me | H | H | Me | 2,4-$Cl_2$-Ph | O | |
| 1-1032 | $CH_2OMe$ | H | H | Me | 2,4-$Cl_2$-Ph | O | |
| 1-1033 | $CH_2OEt$ | H | H | Me | 2,4-$Cl_2$-Ph | O | |
| 1-1034 | $CH_2Oi$-Pr | H | H | Me | 2,4-$Cl_2$-Ph | O | |
| 1-1035 | H | H | H | Me | 2,4-$Cl_2$-5-F-Ph | O | 1.5288 (20) |
| 1-1036 | $CO_2Me$ | H | H | Me | 2,4-$Cl_2$-5-F-Ph | O | 1.5150 (22) |
| 1-1037 | $CO_2Et$ | H | H | Me | 2,4-$Cl_2$-5-F-Ph | O | 1.5202 (21) |
| 1-1038 | $CO_2n$-Pr | H | H | Me | 2,4-$Cl_2$-5-F-Ph | O | |
| 1-1039 | $CO_2n$-Bu | H | H | Me | 2,4-$Cl_2$-5-F-Ph | O | |
| 1-1040 | $CO_2i$-Bu | H | H | Me | 2,4-$Cl_2$-5-F-Ph | O | |
| 1-1041 | $CO_2CH_2t$-Bu | H | H | Me | 2,4-$Cl_2$-5-F-Ph | O | |
| 1-1042 | $CO_2Ph$ | H | H | Me | 2,4-$Cl_2$-5-F-Ph | O | |
| 1-1043 | Me | H | H | Me | 2,4-$Cl_2$-5-F-Ph | O | |
| 1-1044 | $CH_2OMe$ | H | H | Me | 2,4-$Cl_2$-5-F-Ph | O | |
| 1-1045 | $CH_2OEt$ | H | H | Me | 2,4-$Cl_2$-5-F-Ph | O | |
| 1-1046 | $CH_2Oi$-Pr | H | H | Me | 2,4-$Cl_2$-5-F-Ph | O | |
| 1-1047 | H | H | H | Me | $CH_2C(Me)_2OMe$ | O | 1.4991 (21) |
| 1-1048 | $CO_2Me$ | H | H | Me | $CH_2C(Me)_2OMe$ | O | |
| 1-1049 | $CO_2Et$ | H | H | Me | $CH_2C(Me)_2OMe$ | O | 1.4903 (22) |
| 1-1050 | $CO_2n$-Pr | H | H | Me | $CH_2C(Me)_2OMe$ | O | |
| 1-1051 | $CO_2n$-Bu | H | H | Me | $CH_2C(Me)_2OMe$ | O | |
| 1-1052 | $CO_2i$-Bu | H | H | Me | $CH_2C(Me)_2OMe$ | O | 1.4849 (22) |
| 1-1053 | $CO_2CH_2t$-Bu | H | H | Me | $CH_2C(Me)_2OMe$ | O | 1.4630 (23) |
| 1-1054 | $CO_2Ph$ | H | H | Me | $CH_2C(Me)_2OMe$ | O | |
| 1-1055 | Me | H | H | Me | $CH_2C(Me)_2OMe$ | O | |
| 1-1056 | $CH_2OMe$ | H | H | Me | $CH_2C(Me)_2OMe$ | O | |
| 1-1057 | $CH_2OEt$ | H | H | Me | $CH_2C(Me)_2OMe$ | O | |
| 1-1058 | $CH_2Oi$-Pr | H | H | Me | $CH_2C(Me)_2OMe$ | O | |
| 1-1059 | H | H | H | Me | 2,4-$Me_2$-Ph | O | 136.9 |
| 1-1060 | $CO_2Me$ | H | H | Me | 2,4-$Me_2$-Ph | O | 64.1-69.8 |
| 1-1061 | $CO_2Et$ | H | H | Me | 2,4-$Me_2$-Ph | O | 1.5225 (21) |
| 1-1062 | $CO_2n$-Pr | H | H | Me | 2,4-$Me_2$-Ph | O | |
| 1-1063 | $CO_2n$-Bu | H | H | Me | 2,4-$Me_2$-Ph | O | |
| 1-1064 | $CO_2i$-Bu | H | H | Me | 2,4-$Me_2$-Ph | O | |
| 1-1065 | $CO_2CH_2t$-Bu | H | H | Me | 2,4-$Me_2$-Ph | O | |
| 1-1066 | $CO_2Ph$ | H | H | Me | 2,4-$Me_2$-Ph | O | |
| 1-1067 | Me | H | H | Me | 2,4-$Me_2$-Ph | O | |
| 1-1068 | $CH_2OMe$ | H | H | Me | 2,4-$Me_2$-Ph | O | |

TABLE 1-continued

General Formula (I)

(I-2)

$$\text{(m = 0, A = O, R}^1\text{ = CF}_3\text{, R}^5\text{ = R}^6\text{ = H)}$$

| Compound No. | $R^2$ | $R^7$ | $R^8$ | $R^9$ | $R^{10}$ | W | Physical properties |
|---|---|---|---|---|---|---|---|
| 1-1069 | $CH_2OEt$ | H | H | Me | 2,4-$Me_2$-Ph | O | |
| 1-1070 | $CH_2Oi$-Pr | H | H | Me | 2,4-$Me_2$-Ph | O | |
| 1-1071 | H | H | H | Me | 4-MeO-Ph | O | 73-76 |
| 1-1072 | $CO_2Me$ | H | H | Me | 4-MeO-Ph | O | |
| 1-1073 | $CO_2Et$ | H | H | Me | 4-MeO-Ph | O | 1.5210 (19) |
| 1-1074 | $CO_2n$-Pr | H | H | Me | 4-MeO-Ph | O | |
| 1-1075 | $CO_2n$-Bu | H | H | Me | 4-MeO-Ph | O | |
| 1-1076 | $CO_2i$-Bu | H | H | Me | 4-MeO-Ph | O | |
| 1-1077 | $CO_2CH_2t$-Bu | H | H | Me | 4-MeO-Ph | O | |
| 1-1078 | $CO_2Ph$ | H | H | Me | 4-MeO-Ph | O | |
| 1-1079 | Me | H | H | Me | 4-MeO-Ph | O | |
| 1-1080 | $CH_2OMe$ | H | H | Me | 4-MeO-Ph | O | |
| 1-1081 | $CH_2OEt$ | H | H | Me | 4-MeO-Ph | O | |
| 1-1082 | $CH_2Oi$-Pr | H | H | Me | 4-MeO-Ph | O | |
| 1-1083 | H | H | H | Me | 2-F-4-MeO-Ph | O | 1.5288 (19) |
| 1-1084 | $CO_2Me$ | H | H | Me | 2-F-4-MeO-Ph | O | |
| 1-1085 | $CO_2Et$ | H | H | Me | 2-F-4-MeO-Ph | O | 1.5168 (19) |
| 1-1086 | $CO_2n$-Pr | H | H | Me | 2-F-4-MeO-Ph | O | |
| 1-1087 | $CO_2n$-Bu | H | H | Me | 2-F-4-MeO-Ph | O | |
| 1-1088 | $CO_2i$-Bu | H | H | Me | 2-F-4-MeO-Ph | O | |
| 1-1089 | $CO_2CH_2t$-Bu | H | H | Me | 2-F-4-MeO-Ph | O | |
| 1-1090 | $CO_2Ph$ | H | H | Me | 2-F-4-MeO-Ph | O | |
| 1-1091 | Me | H | H | Me | 2-F-4-MeO-Ph | O | |
| 1-1092 | $CH_2OMe$ | H | H | Me | 2-F-4-MeO-Ph | O | |
| 1-1093 | $CH_2OEt$ | H | H | Me | 2-F-4-MeO-Ph | O | |
| 1-1094 | $CH_2Oi$-Pr | H | H | Me | 2-F-4-MeO-Ph | O | |
| 1-1095 | H | H | H | Me | 3-F-4-MeO-Ph | O | 91-94 |
| 1-1096 | $CO_2Me$ | H | H | Me | 3-F-4-MeO-Ph | O | |
| 1-1097 | $CO_2Et$ | H | H | Me | 3-F-4-MeO-Ph | O | 1.5068 (19) |
| 1-1098 | $CO_2n$-Pr | H | H | Me | 3-F-4-MeO-Ph | O | |
| 1-1099 | $CO_2n$-Bu | H | H | Me | 3-F-4-MeO-Ph | O | |
| 1-1100 | $CO_2i$-Bu | H | H | Me | 3-F-4-MeO-Ph | O | |
| 1-1101 | $CO_2CH_2t$-Bu | H | H | Me | 3-F-4-MeO-Ph | O | |
| 1-1102 | $CO_2Ph$ | H | H | Me | 3-F-4-MeO-Ph | O | |
| 1-1103 | Me | H | H | Me | 3-F-4-MeO-Ph | O | |
| 1-1104 | $CH_2OMe$ | H | H | Me | 3-F-4-MeO-Ph | O | |
| 1-1105 | $CH_2OEt$ | H | H | Me | 3-F-4-MeO-Ph | O | |
| 1-1106 | $CH_2Oi$-Pr | H | H | Me | 3-F-4-MeO-Ph | O | |
| 1-1107 | H | H | H | Me | 3,4-$Me_2$-Ph | O | 117.8 |
| 1-1108 | $CO_2Me$ | H | H | Me | 3,4-$Me_2$-Ph | O | 1.5068 (20) |
| 1-1109 | $CO_2Et$ | H | H | Me | 3,4-$Me_2$-Ph | O | 1.5135 (20) |
| 1-1110 | $CO_2n$-Pr | H | H | Me | 3,4-$Me_2$-Ph | O | |
| 1-1111 | $CO_2n$-Bu | H | H | Me | 3,4-$Me_2$-Ph | O | |
| 1-1112 | $CO_2i$-Bu | H | H | Me | 3,4-$Me_2$-Ph | O | |
| 1-1113 | $CO_2CH_2t$-Bu | H | H | Me | 3,4-$Me_2$-Ph | O | |
| 1-1114 | $CO_2Ph$ | H | H | Me | 3,4-$Me_2$-Ph | O | |
| 1-1115 | Me | H | H | Me | 3,4-$Me_2$-Ph | O | |
| 1-1116 | $CH_2OMe$ | H | H | Me | 3,4-$Me_2$-Ph | O | |
| 1-1117 | $CH_2OEt$ | H | H | Me | 3,4-$Me_2$-Ph | O | |
| 1-1118 | $CH_2Oi$-Pr | H | H | Me | 3,4-$Me_2$-Ph | O | |
| 1-1119 | H | H | H | Me | 2,5-$Me_2$-Ph | O | 116.2 |
| 1-1120 | $CO_2Me$ | H | H | Me | 2,5-$Me_2$-Ph | O | 1.5070 (21) |
| 1-1121 | $CO_2Et$ | H | H | Me | 2,5-$Me_2$-Ph | O | 1.5102 (21) |
| 1-1122 | $CO_2n$-Pr | H | H | Me | 2,5-$Me_2$-Ph | O | |
| 1-1123 | $CO_2n$-Bu | H | H | Me | 2,5-$Me_2$-Ph | O | |
| 1-1124 | $CO_2i$-Bu | H | H | Me | 2,5-$Me_2$-Ph | O | |
| 1-1125 | $CO_2CH_2t$-Bu | H | H | Me | 2,5-$Me_2$-Ph | O | |
| 1-1126 | $CO_2Ph$ | H | H | Me | 2,5-$Me_2$-Ph | O | |
| 1-1127 | Me | H | H | Me | 2,5-$Me_2$-Ph | O | |
| 1-1128 | $CH_2OMe$ | H | H | Me | 2,5-$Me_2$-Ph | O | |

TABLE 1-continued

General Formula (I)

(I-2)

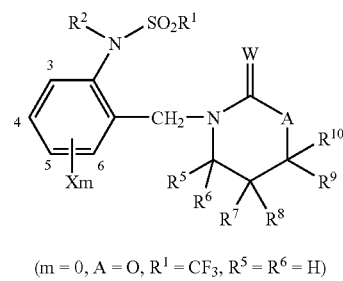

(m = 0, A = O, $R^1$ = $CF_3$, $R^5$ = $R^6$ = H)

| Compound No. | $R^2$ | $R^7$ | $R^8$ | $R^9$ | $R^{10}$ | W | Physical properties |
|---|---|---|---|---|---|---|---|
| 1-1129 | $CH_2OEt$ | H | H | Me | 2,5-$Me_2$-Ph | O | |
| 1-1130 | $CH_2Oi$-Pr | H | H | Me | 2,5-$Me_2$-Ph | O | |
| 1-1131 | H | H | H | Me | 2,4,6-$Me_3$-Ph | O | |
| 1-1132 | $CO_2Me$ | H | H | Me | 2,4,6-$Me_3$-Ph | O | |
| 1-1133 | $CO_2Et$ | H | H | Me | 2,4,6-$Me_3$-Ph | O | |
| 1-1134 | $CO_2n$-Pr | H | H | Me | 2,4,6-$Me_3$-Ph | O | |
| 1-1135 | $CO_2n$-Bu | H | H | Me | 2,4,6-$Me_3$-Ph | O | |
| 1-1136 | $CO_2i$-Bu | H | H | Me | 2,4,6-$Me_3$-Ph | O | |
| 1-1137 | $CO_2CH_2t$-Bu | H | H | Me | 2,4,6-$Me_3$-Ph | O | |
| 1-1138 | $CO_2Ph$ | H | H | Me | 2,4,6-$Me_3$-Ph | O | |
| 1-1139 | Me | H | H | Me | 2,4,6-$Me_3$-Ph | O | |
| 1-1140 | $CH_2OMe$ | H | H | Me | 2,4,6-$Me_3$-Ph | O | |
| 1-1141 | $CH_2OEt$ | H | H | Me | 2,4,6-$Me_3$-Ph | O | |
| 1-1142 | $CH_2Oi$-Pr | H | H | Me | 2,4,6-$Me_3$-Ph | O | |
| 1-1143 | H | H | H | Me | 3,4-$(MeO)_2$-Ph | O | |
| 1-1144 | $CO_2Me$ | H | H | Me | 3,4-$(MeO)_2$-Ph | O | |
| 1-1145 | $CO_2Et$ | H | H | Me | 3,4-$(MeO)_2$-Ph | O | |
| 1-1146 | $CO_2n$-Pr | H | H | Me | 3,4-$(MeO)_2$-Ph | O | |
| 1-1147 | $CO_2n$-Bu | H | H | Me | 3,4-$(MeO)_2$-Ph | O | |
| 1-1148 | $CO_2i$-Bu | H | H | Me | 3,4-$(MeO)_2$-Ph | O | |
| 1-1149 | $CO_2CH_2t$-Bu | H | H | Me | 3,4-$(MeO)_2$-Ph | O | |
| 1-1150 | $CO_2Ph$ | H | H | Me | 3,4-$(MeO)_2$-Ph | O | |
| 1-1151 | Me | H | H | Me | 3,4-$(MeO)_2$-Ph | O | |
| 1-1152 | $CH_2OMe$ | H | H | Me | 3,4-$(MeO)_2$-Ph | O | |
| 1-1153 | $CH_2OEt$ | H | H | Me | 3,4-$(MeO)_2$-Ph | O | |
| 1-1154 | $CH_2Oi$-Pr | H | H | Me | 3,4-$(MeO)_2$-Ph | O | |
| 1-1155 | H | H | H | Me | 3,4-$OCH_2O$-Ph | O | |
| 1-1156 | $CO_2Me$ | H | H | Me | 3,4-$OCH_2O$-Ph | O | |
| 1-1157 | $CO_2Et$ | H | H | Me | 3,4-$OCH_2O$-Ph | O | |
| 1-1158 | $CO_2n$-Pr | H | H | Me | 3,4-$OCH_2O$-Ph | O | |
| 1-1159 | $CO_2n$-Bu | H | H | Me | 3,4-$OCH_2O$-Ph | O | |
| 1-1160 | $CO_2i$-Bu | H | H | Me | 3,4-$OCH_2O$-Ph | O | |
| 1-1161 | $CO_2CH_2t$-Bu | H | H | Me | 3,4-$OCH_2O$-Ph | O | |
| 1-1162 | $CO_2Ph$ | H | H | Me | 3,4-$OCH_2O$-Ph | O | |
| 1-1163 | Me | H | H | Me | 3,4-$OCH_2O$-Ph | O | |
| 1-1164 | $CH_2OMe$ | H | H | Me | 3,4-$OCH_2O$-Ph | O | |
| 1-1165 | $CH_2OEt$ | H | H | Me | 3,4-$OCH_2O$-Ph | O | |
| 1-1166 | $CH_2Oi$-Pr | H | H | Me | 3,4-$OCH_2O$-Ph | O | |
| 1-1167 | H | H | H | Me | 3,4-$OCH_2O$-Ph | O | |
| 1-1168 | $CO_2Me$ | H | H | Me | 3,4-$OCH_2O$-Ph | O | |
| 1-1169 | $CO_2Et$ | H | H | Me | 3,4-$OCH_2O$-Ph | O | |
| 1-1170 | $CO_2n$-Pr | H | H | Me | 3,4-$OCH_2O$-Ph | O | |
| 1-1171 | $CO_2n$-Bu | H | H | Me | 3,4-$OCH_2O$-Ph | O | |
| 1-1172 | $CO_2i$-Bu | H | H | Me | 3,4-$OCH_2O$-Ph | O | |
| 1-1173 | $CO_2CH_2t$-Bu | H | H | Me | 3,4-$OCH_2O$-Ph | O | |
| 1-1174 | $CO_2Ph$ | H | H | Me | 3,4-$OCH_2O$-Ph | O | |
| 1-1175 | Me | H | H | Me | 3,4-$OCH_2O$-Ph | O | |
| 1-1176 | $CH_2OMe$ | H | H | Me | 3,4-$OCH_2O$-Ph | O | |
| 1-1177 | $CH_2OEt$ | H | H | Me | 3,4-$OCH_2O$-Ph | O | |
| 1-1178 | $CH_2Oi$-Pr | H | H | Me | 3,4-$OCH_2O$-Ph | O | |
| 1-1179 | H | H | H | Me | 3-EtO-Ph | O | |
| 1-1180 | $CO_2Me$ | H | H | Me | 3-EtO-Ph | O | |
| 1-1181 | $CO_2Et$ | H | H | Me | 3-EtO-Ph | O | |
| 1-1182 | $CO_2n$-Pr | H | H | Me | 3-EtO-Ph | O | |
| 1-1183 | $CO_2n$-Bu | H | H | Me | 3-EtO-Ph | O | |
| 1-1184 | $CO_2i$-Bu | H | H | Me | 3-EtO-Ph | O | |
| 1-1185 | $CO_2CH_2t$-Bu | H | H | Me | 3-EtO-Ph | O | |
| 1-1186 | $CO_2Ph$ | H | H | Me | 3-EtO-Ph | O | |
| 1-1187 | Me | H | H | Me | 3-EtO-Ph | O | |
| 1-1188 | $CH_2OMe$ | H | H | Me | 3-EtO-Ph | O | |

TABLE 1-continued

General Formula (I)

(I-2)

(m = 0, A = O, $R^1$ = $CF_3$, $R^5$ = $R^6$ = H)

| Compound No. | $R^2$ | $R^7$ | $R^8$ | $R^9$ | $R^{10}$ | W | Physical properties |
|---|---|---|---|---|---|---|---|
| 1-1189 | $CH_2$aEt | H | H | Me | 3-EtO-Ph | O | |
| 1-1190 | $CH_2$Oi-Pr | H | H | Me | 3-EtO-Ph | O | |
| 1-1191 | H | H | H | Me | 3-i-PrO-Ph | O | |
| 1-1192 | $CO_2$Me | H | H | Me | 3-i-PrO-Ph | O | |
| 1-1193 | $CO_2$Et | H | H | Me | 3-i-PrO-Ph | O | |
| 1-1194 | $CO_2$n-Pr | H | H | Me | 3-i-PrO-Ph | O | |
| 1-1195 | $CO_2$n-Bu | H | H | Me | 3-i-PrO-Ph | O | |
| 1-1196 | $CO_2$i-Bu | H | H | Me | 3-i-PrO-Ph | O | |
| 1-1197 | $CO_2CH_2$t-Bu | H | H | Me | 3-i-PrO-Ph | O | |
| 1-1198 | $CO_2$Ph | H | H | Me | 3-i-PrO-Ph | O | |
| 1-1199 | Me | H | H | Me | 3-i-PrO-Ph | O | |
| 1-1200 | $CH_2$OMe | H | H | Me | 3-i-PrO-Ph | O | |
| 1-1201 | $CH_2$OEt | H | H | Me | 3-i-PrO-Ph | O | |
| 1-1202 | $CH_2$Oi-Pr | H | H | Me | 3-i-PrO-Ph | O | |
| 1-1203 | H | H | H | Me | 3-i-PrO-Ph | O | |
| 1-1204 | $CO_2$Me | H | H | Me | 3-i-PrO-Ph | O | |
| 1-1205 | $CO_2$Et | H | H | Me | 3-i-PrO-Ph | O | |
| 1-1206 | $CO_2$n-Pr | H | H | Me | 3-i-PrO-Ph | O | |
| 1-1207 | $CO_2$n-Bu | H | H | Me | 3-i-PrO-Ph | O | |
| 1-1208 | $CO_2$i-Bu | H | H | Me | 3-i-PrO-Ph | O | |
| 1-1209 | $CO_2CH_2$t-Bu | H | H | Me | 3-i-PrO-Ph | O | |
| 1-1210 | $CO_2$Ph | H | H | Me | 3-i-PrO-Ph | O | |
| 1-1211 | Me | H | H | Me | 3-i-PrO-Ph | O | |
| 1-1212 | $CH_2$OMe | H | H | Me | 3-i-PrO-Ph | O | |
| 1-1213 | $CH_2$OEt | H | H | Me | 3-i-PrO-Ph | O | |
| 1-1214 | $CH_2$Oi-Pr | H | H | Me | 3-i-PrO-Ph | O | |
| 1-1215 | H | H | H | Me | 3-$CF_3$ | O | 1.4957 (19) |
| 1-1216 | $CO_2$Me | H | H | Me | 3-$CF_3$ | O | 1.4580 (20) |
| 1-1217 | $CO_2$Et | H | H | Me | 3-$CF_3$ | O | 1.4976 (20) |
| 1-1218 | $CO_2$n-Pr | H | H | Me | 3-$CF_3$ | O | |
| 1-1219 | $CO_2$n-Bu | H | H | Me | 3-$CF_3$ | O | |
| 1-1220 | $CO_2$i-Bu | H | H | Me | 3-$CF_3$ | O | |
| 1-1221 | $CO_2CH_2$t-Bu | H | H | Me | 3-$CF_3$ | O | |
| 1-1222 | $CO_2$Ph | H | H | Me | 3-$CF_3$ | O | |
| 1-1223 | Me | H | H | Me | 3-$CF_3$ | O | |
| 1-1224 | $CH_2$OMe | H | H | Me | 3-$CF_3$ | O | |
| 1-1225 | $CH_2$OEt | H | H | Me | 3-$CF_3$ | O | |
| 1-1226 | $CH_2$Oi-Pr | H | H | Me | 3-$CF_3$ | O | |
| 1-1227 | H | H | H | Me | 4-$CF_3$ | O | |
| 1-1228 | $CO_2$Me | H | H | Me | 4-$CF_3$ | O | |
| 1-1229 | $CO_2$Et | H | H | Me | 4-$CF_3$ | O | |
| 1-1230 | $CO_2$n-Pr | H | H | Me | 4-$CF_3$ | O | |
| 1-1231 | $CO_2$n-Bu | H | H | Me | 4-$CF_3$ | O | |
| 1-1232 | $CO_2$i-Bu | H | H | Me | 4-$CF_3$ | O | |
| 1-1233 | $CO_2CH_2$t-Bu | H | H | Me | 4-$CF_3$ | O | |
| 1-1234 | $CO_2$Ph | H | H | Me | 4-$CF_3$ | O | |
| 1-1235 | Me | H | H | Me | 4-$CF_3$ | O | |
| 1-1236 | $CH_2$OMe | H | H | Me | 4-$CF_3$ | O | |
| 1-1237 | $CH_2$OEt | H | H | Me | 4-$CF_3$ | O | |
| 1-1238 | $CH_2$Oi-Pr | H | H | Me | 4-$CF_3$ | O | |
| 1-1239 | H | H | H | Me | 2,5-$Cl_2$ | O | 169.2-170.2 |
| 1-1240 | $CO_2$Me | H | H | Me | 2,5-$Cl_2$ | O | 1.5145 (22) |
| 1-1241 | $CO_2$Et | H | H | Me | 2,5-$Cl_2$ | O | 1.5068 (21) |
| 1-1242 | $CO_2$n-Pr | H | H | Me | 2,5-$Cl_2$ | O | |
| 1-1243 | $CO_2$n-Bu | H | H | Me | 2,5-$Cl_2$ | O | |
| 1-1244 | $CO_2$i-Bu | H | H | Me | 2,5-$Cl_2$ | O | |
| 1-1245 | $CO_2CH_2$t-Bu | H | H | Me | 2,5-$Cl_2$ | O | |
| 1-1246 | $CO_2$Ph | H | H | Me | 2,5-$Cl_2$ | O | |
| 1-1247 | Me | H | H | Me | 2,5-$Cl_2$ | O | |
| 1-1248 | $CH_2$OMe | H | H | Me | 2,5-$Cl_2$ | O | |

TABLE 1-continued

General Formula (I)

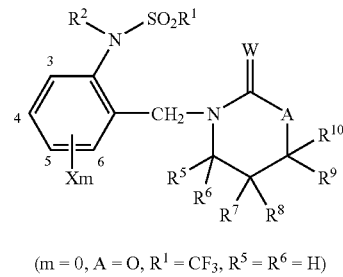

(I-2)

(m = 0, A = O, $R^1$ = $CF_3$, $R^5$ = $R^6$ = H)

| Compound No. | $R^2$ | $R^7$ | $R^8$ | $R^9$ | $R^{10}$ | W | Physical properties |
|---|---|---|---|---|---|---|---|
| 1-1249 | $CH_2OEt$ | H | H | Me | 2,5-$Cl_2$ | O | |
| 1-1250 | $CH_2Oi$-Pr | H | H | Me | 2,5-$Cl_2$ | O | |
| 1-1251 | H | H | H | Me | 4-PhO-Ph | O | |
| 1-1252 | $CO_2Me$ | H | H | Me | 4-PhO-Ph | O | |
| 1-1253 | $CO_2Et$ | H | H | Me | 4-PhO-Ph | O | |
| 1-1254 | $CO_2n$-Pr | H | H | Me | 4-PhO-Ph | O | |
| 1-1255 | $CO_2n$-Bu | H | H | Me | 4-PhO-Ph | O | |
| 1-1256 | $CO_2i$-Bu | H | H | Me | 4-PhO-Ph | O | |
| 1-1257 | $CO_2CH_2t$-Bu | H | H | Me | 4-PhO-Ph | O | |
| 1-1258 | $CO_2Ph$ | H | H | Me | 4-PhO-Ph | O | |
| 1-1259 | Me | H | H | Me | 4-PhO-Ph | O | |
| 1-1260 | $CH_2OMe$ | H | H | Me | 4-PhO-Ph | O | |
| 1-1261 | $CH_2OEt$ | H | H | Me | 4-PhO-Ph | O | |
| 1-1262 | $CH_2Oi$-Pr | H | H | Me | 4-PhO-Ph | O | |
| 1-1263 | H | H | H | Me | 4-Br-Ph | O | 1.5323 (19) |
| 1-1264 | $CO_2Me$ | H | H | Me | 4-Br-Ph | O | 1.5195 (22) |
| 1-1265 | $CO_2Et$ | H | H | Me | 4-Br-Ph | O | 1.5222 (22) |
| 1-1266 | $CO_2n$-Pr | H | H | Me | 4-Br-Ph | O | |
| 1-1267 | $CO_2n$-Bu | H | H | Me | 4-Br-Ph | O | |
| 1-1268 | $CO_2i$-Bu | H | H | Me | 4-Br-Ph | O | |
| 1-1269 | $CO_2CH_2t$-Bu | H | H | Me | 4-Br-Ph | O | |
| 1-1270 | $CO_2Ph$ | H | H | Me | 4-Br-Ph | O | |
| 1-1271 | Me | H | H | Me | 4-Br-Ph | O | |
| 1-1272 | $CH_2OMe$ | H | H | Me | 4-Br-Ph | O | |
| 1-1273 | $CH_2OEt$ | H | H | Me | 4-Br-Ph | O | |
| 1-1274 | $CH_2Oi$-Pr | H | H | Me | 4-Br-Ph | O | |
| 1-1275 | H | H | H | Et | 2-F-Ph | O | |
| 1-1276 | $CO_2Me$ | H | H | Et | 2-F-Ph | O | |
| 1-1277 | $CO_2Et$ | H | H | Et | 2-F-Ph | O | |
| 1-1278 | $CO_2n$-Pr | H | H | Et | 2-F-Ph | O | |
| 1-1279 | $CO_2n$-Bu | H | H | Et | 2-F-Ph | O | |
| 1-1280 | $CO_2i$-Bu | H | H | Et | 2-F-Ph | O | |
| 1-1281 | $CO_2CH_2t$-Bu | H | H | Et | 2-F-Ph | O | |
| 1-1282 | $CO_2Ph$ | H | H | Et | 2-F-Ph | O | |
| 1-1283 | Me | H | H | Et | 2-F-Ph | O | |
| 1-1284 | $CH_2OMe$ | H | H | Et | 2-F-Ph | O | |
| 1-1285 | $CH_2OEt$ | H | H | Et | 2-F-Ph | O | |
| 1-1286 | $CH_2Oi$-Pr | H | H | Et | 2-F-Ph | O | |
| 1-1287 | H | H | H | Et | 3-MeO-Ph | O | |
| 1-1288 | $CO_2Me$ | H | H | Et | 3-MeO-Ph | O | |
| 1-1289 | $CO_2Et$ | H | H | Et | 3-MeO-Ph | O | |
| 1-1290 | $CO_2n$-Pr | H | H | Et | 3-MeO-Ph | O | |
| 1-1291 | $CO_2n$-Bu | H | H | Et | 3-MeO-Ph | O | |
| 1-1292 | $CO_2i$-Bu | H | H | Et | 3-MeO-Ph | O | |
| 1-1293 | $CO_2CH_2t$-Bu | H | H | Et | 3-MeO-Ph | O | |
| 1-1294 | $CO_2Ph$ | H | H | Et | 3-MeO-Ph | O | |
| 1-1295 | Me | H | H | Et | 3-MeO-Ph | O | |
| 1-1296 | $CH_2OMe$ | H | H | Et | 3-MeO-Ph | O | |
| 1-1297 | $CH_2OEt$ | H | H | Et | 3-MeO-Ph | O | |
| 1-1298 | $CH_2Oi$-Pr | H | H | Et | 3-MeO-Ph | O | |
| 1-1299 | H | H | H | Me | c-Hex | O | |
| 1-1300 | $CO_2Me$ | H | H | Me | c-Hex | O | |
| 1-1301 | $CO_2Et$ | H | H | Me | c-Hex | O | |
| 1-1302 | $CO_2n$-Pr | H | H | Me | c-Hex | O | |
| 1-1303 | $CO_2n$-Bu | H | H | Me | c-Hex | O | |
| 1-1304 | $CO_2i$-Bu | H | H | Me | c-Hex | O | |
| 1-1305 | $CO_2CH_2t$-Bu | H | H | Me | c-Hex | O | |
| 1-1306 | $CO_2Ph$ | H | H | Me | c-Hex | O | |
| 1-1307 | Me | H | H | Me | c-Hex | O | |
| 1-1308 | $CH_2OMe$ | H | H | Me | c-Hex | O | |

TABLE 1-continued

General Formula (I)

(I-2)

(m = 0, A = O, $R^1$ = $CF_3$, $R^5$ = $R^6$ = H)

| Compound No. | $R^2$ | $R^7$ | $R^8$ | $R^9$ | $R^{10}$ | W | Physical properties |
|---|---|---|---|---|---|---|---|
| 1-1309 | $CH_2OEt$ | H | H | Me | c-Hex | O | |
| 1-1310 | $CH_2Oi$-Pr | H | H | Me | c-Hex | O | |
| 1-1311 | H | H | H | | $(CH_2)_2O(CH_2)_2$ | O | |
| 1-1312 | $CO_2Me$ | H | H | | $(CH_2)_2O(CH_2)_2$ | O | |
| 1-1313 | $CO_2Et$ | H | H | | $(CH_2)_2O(CH_2)_2$ | O | |
| 1-1314 | $CO_2n$-Pr | H | H | | $(CH_2)_2O(CH_2)_2$ | O | |
| 1-1315 | $CO_2n$-Bu | H | H | | $(CH_2)_2O(CH_2)_2$ | O | |
| 1-1316 | $CO_2i$-Bu | H | H | | $(CH_2)_2O(CH_2)_2$ | O | |
| 1-1317 | $CO_2CH_2t$-Bu | H | H | | $(CH_2)_2O(CH_2)_2$ | O | |
| 1-1318 | $CO_2Ph$ | H | H | | $(CH_2)_2O(CH_2)_2$ | O | |
| 1-1319 | Me | H | H | | $(CH_2)_2O(CH_2)_2$ | O | |
| 1-1320 | $CH_2OMe$ | H | H | | $(CH_2)_2O(CH_2)_2$ | O | |
| 1-1321 | $CH_2OEt$ | H | H | | $(CH_2)_2O(CH_2)_2$ | O | |
| 1-1322 | $CH_2Oi$-Pr | H | H | | $(CH_2)_2O(CH_2)_2$ | O | |
| 1-1323 | H | H | H | Me | 2,6-$Cl_2$-3-F-Ph | O | |
| 1-1324 | $CO_2Me$ | H | H | Me | 2,6-$Cl_2$-3-F-Ph | O | |
| 1-1325 | $CO_2Et$ | H | H | Me | 2,6-$Cl_2$-3-F-Ph | O | |
| 1-1326 | $CO_2n$-Pr | H | H | Me | 2,6-$Cl_2$-3-F-Ph | O | |
| 1-1327 | $CO_2n$-Bu | H | H | Me | 2,6-$Cl_2$-3-F-Ph | O | |
| 1-1328 | $CO_2i$-Bu | H | H | Me | 2,6-$Cl_2$-3-F-Ph | O | |
| 1-1329 | $CO_2CH_2t$-Bu | H | H | Me | 2,6-$Cl_2$-3-F-Ph | O | |
| 1-1330 | $CO_2Ph$ | H | H | Me | 2,6-$Cl_2$-3-F-Ph | O | |
| 1-1331 | Me | H | H | Me | 2,6-$Cl_2$-3-F-Ph | O | |
| 1-1332 | $CH_2OMe$ | H | H | Me | 2,6-$Cl_2$-3-F-Ph | O | |
| 1-1333 | $CH_2OEt$ | H | H | Me | 2,6-$Cl_2$-3-F-Ph | O | |
| 1-1334 | $CH_2Oi$-Pr | H | H | Me | 2,6-$Cl_2$-3-F-Ph | O | |

TABLE 2

General Formula (I-3)

(I-3)

(m = 0, A = O, $R^5$ = $R^6$ = $R^7$ = $R^8$ = H)

| Compound No. | Substituted site | $R^1$ | $R^2$ | $R^{7'}$ | $R^{8'}$ | $R^9$ | $R^{10}$ | W | Physical properties |
|---|---|---|---|---|---|---|---|---|---|
| 2-1 | 2 | $CF_3$ | H | H | H | H | H | O | 110.6 |
| 2-2 | 2 | $CF_3$ | $CO_2Me$ | H | H | H | H | O | |
| 2-3 | 2 | $CF_3$ | $CO_2Et$ | H | H | H | H | O | 1.4977 (27) |
| 2-4 | 2 | $CF_3$ | $CO_2n$-Pr | H | H | H | H | O | 86.7 |
| 2-5 | 2 | $CF_3$ | $CO_2n$-Bu | H | H | H | H | O | 1.4935 (26) |
| 2-6 | 2 | $CF_3$ | $CO_2i$-Bu | H | H | H | H | O | 1.4928 (26) |
| 2-7 | 2 | $CF_3$ | $CO_2CH_2t$-Bu | H | H | H | H | O | |
| 2-8 | 2 | $CF_3$ | Me | H | H | H | H | O | |
| 2-9 | 2 | $CF_3$ | $CH_2OMe$ | H | H | H | H | O | |
| 2-10 | 2 | $CF_3$ | $CH_2OEt$ | H | H | H | H | O | |

TABLE 2-continued

General Formula (I-3)

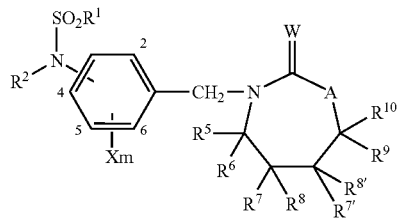

(I-3)

(m = 0, A = O, $R^5 = R^6 = R^7 = R^8 = H$)

| Compound No. | Substituted site | $R^1$ | $R^2$ | $R^{7'}$ | $R^{8'}$ | $R^9$ | $R^{10}$ | W | Physical properties |
|---|---|---|---|---|---|---|---|---|---|
| 2-11 | 2 | $CF_3$ | $CH_2$i-Pr | H | H | H | H | O | |
| 2-12 | 2 | $CF_3$ | H | H | H | H | H | S | 1.5204 (26) |
| 2-13 | 2 | $CF_3$ | $CO_2$Me | H | H | H | H | S | |
| 2-14 | 2 | $CF_3$ | $CO_2$Et | H | H | H | H | S | 49.7-52.8 |
| 2-15 | 2 | $CF_3$ | $CO_2$n-Pr | H | H | H | H | S | |
| 2-16 | 2 | $CF_3$ | $CO_2$n-Bu | H | H | H | H | S | |
| 2-17 | 2 | $CF_3$ | $CO_2$i-Bu | H | H | H | H | S | 59.3-62.8 |
| 2-18 | 2 | $CF_3$ | $CO_2CH_2$t-Bu | H | H | H | H | S | |
| 2-19 | 2 | $CF_3$ | Me | H | H | H | H | S | |
| 2-20 | 2 | $CF_3$ | $CH_2$OMe | H | H | H | H | S | |
| 2-21 | 2 | $CF_3$ | $CH_2$OEt | H | H | H | H | S | |
| 2-22 | 2 | $CF_3$ | $CH_2$Oi-Pr | H | H | H | H | S | |
| 2-23 | 2 | $CF_3$ | H | Me | H | H | H | O | 1.4945 (26) |
| 2-24 | 2 | $CF_3$ | $CO_2$Me | Me | H | H | H | O | 1.4965 (25) |
| 2-25 | 2 | $CF_3$ | $CO_2$Et | Me | H | H | H | O | 1.4909 (25) |
| 2-26 | 2 | $CF_3$ | $CO_2$n-Pr | Me | H | H | H | O | |
| 2-27 | 2 | $CF_3$ | $CO_2$n-Bu | Me | H | H | H | O | 1.4889 (25) |
| 2-28 | 2 | $CF_3$ | $CO_2$i-Bu | Me | H | H | H | O | 1.4898 (25) |
| 2-29 | 2 | $CF_3$ | $CO_2CH_2$t-Bu | Me | H | H | H | O | |
| 2-30 | 2 | $CF_3$ | Me | Me | H | H | H | O | |
| 2-31 | 2 | $CF_3$ | $CH_2$OMe | Me | H | H | H | O | |
| 2-32 | 2 | $CF_3$ | $CH_2$OEt | Me | H | H | H | O | |
| 2-33 | 2 | $CF_3$ | $CH_2$Oi-Pr | Me | H | H | H | O | |
| 2-34 | 2 | $CF_3$ | $CO_2CH_2CCl_3$ | Me | H | H | H | O | 1.5041 (25) |

TABLE 3-1

General Formula (IV-1)

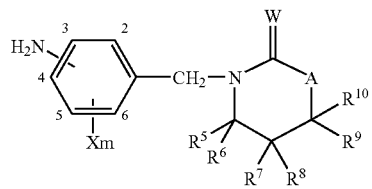

(IV-1)

(m = 0, A = O, $R^5 = R^6 = H$)

| Compound No. | Substituted site | $R^7$ | $R^8$ | $R^9$ | $R^{10}$ | W | Physical properties |
|---|---|---|---|---|---|---|---|
| 3-1 | 2 | H | H | H | H | O | 1.5489 (22) |
| 3-2 | 2 | H | H | H | H | S | 1.6278 (24) |
| 3-3 | 2 | Me | Me | H | H | O | 1.5509 (23) |
| 3-4 | 2 | Me | Me | H | H | S | 90.8-92.1 |
| 3-5 | 2 | H | H | Me | Me | O | 1.5402 (22) |
| 3-6 | 2 | H | H | Me | Me | S | 1.5815 (22) |
| 3-7 | 2 | H | H | Me | Et | O | 1.5476 (22) |
| 3-8 | 2 | H | H | Me | $CF_3$ | O | 1.5088 (22) |
| 3-9 | 2 | H | H | Et | $CF_3$ | O | 1.5069 (22) |
| 3-10 | 2 | H | H | Et | Et | O | 1.5365 (22) |
| 3-11 | 2 | H | H | Et | Et | S | 1.5743 (23) |
| 3-12 | 2 | H | H | Me | c-Pr | O | 1.5481 (20) |
| 3-13 | 2 | H | H | $(CH_2)_4$ | | O | 1.5612 (24) |
| 3-14 | 2 | H | H | c-Pr | c-Pr | O | 1.5475 (27) |
| 3-15 | 2 | H | H | Me | Ph | O | 1.5891 (25) |
| 3-16 | 2 | H | H | Me | 2-Cl-Ph | O | 1.5732 (26) |

TABLE 3-1-continued

General Formula (IV-1)

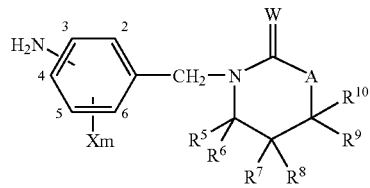

(IV-1)

(m = 0, A = O, $R^5 = R^6$ = H)

| Compound No. | Substituted site | $R^7$ | $R^8$ | $R^9$ | $R^{10}$ | W | Physical properties |
|---|---|---|---|---|---|---|---|
| 3-17 | 2 | H | H | c-Pr | Ph | O | 1.5853 (27) |
| 3-18 | 2 | H | H | c-Pr | 4-Cl-Ph | O | 1.5891 (26) |
| 3-19 | 2 | H | H | c-Bu | Ph | O | 1.5581 (25) |
| 3-20 | 2 | H | H | Ph | Ph | O | 61-65 |
| 3-21 | 2 | H | H | $CF_3$ | Ph | O | 1.5314 (26) |
| 3-22 | 2 | H | H | H | Ph | O | 1.5719 (26) |
| 3-23 | 2 | H | H | H | 2-F-Ph | O | 1.5822 (24) |
| 3-24 | 2 | Me | Me | H | Ph | O | 1.5712 (23) |
| 3-25 | 2 | H | H | H | 2,6-$Cl_2$-Ph | O | 1.5721 (20) |
| 3-26 | 2 | H | H | H | 2-Me-Ph | O | 1.5929 (22) |
| 3-27 | 2 | H | H | H | 2-$CF_3$-Ph | O | 1.5535 (21) |
| 3-28 | 2 | H | H | H | 2-Cl-Ph | O | 1.5892 (23) |
| 3-29 | 2 | H | H | Et | Ph | O | 1.5576 (22) |
| 3-30 | 2 | H | H | $CF_3$ | $CF_3$ | O | 1.4831 (22) |
| 3-31 | 2 | H | H | H | 2,6-$F_2$-Ph | O | 154.2 |
| 3-32 | 2 | H | H | H | 2,6-$Me_2$-Ph | O | 1.5629 (21) |
| 3-33 | 2 | H | H | Me | 1-Me-1-c-Pr | O | 1.5531 (20) |
| 3-34 | 2 | H | H | Me | c-Bu | O | 123.5-126.1 |
| 3-35 | 2 | H | H | Me | 2-$CF_3$Ph | O | 1.4955 (23) |
| 3-36 | 2 | H | H | Et | i-Bu | O | 1.5210 (20) |
| 3-37 | 2 | H | H | Me | 2-F-Ph | O | 110.5 |
| 3-38 | 2 | H | H | Et | i-Pr | O | 1.5295 (26) |
| 3-39 | 2 | H | H | Me | $CH_2$-2-F-Ph | O | 1.5520 (26) |
| 3-40 | 2 | H | H | Me | 4-Cl-Ph | O | 97 |
| 3-41 | 2 | H | H | Me | $CH_2$-2,6-$Cl_2$-Ph | O | 1.5878 (23) |
| 3-42 | 2 | H | H | Et | n-Pr | O | 1.5258 (26) |
| 3-43 | 2 | H | H | Me | neo-Pen | O | 1.5273 (26) |
| 3-44 | 2 | H | H | Me | $CH_2$-2-Cl-Ph | O | 1.5744 (26) |
| 3-45 | 2 | H | H | n-Pr | n-Pr | O | 1.5200 (25) |
| 3-46 | 2 | H | H | Me | $CH_2$-4-Cl-Ph | O | 1.5752 (24) |
| 3-47 | 2 | H | H | i-Bu | i-Bu | O | 1.5192 (25) |
| 3-48 | 2 | H | H | Me | $CH_2$-3-Cl-Ph | O | 1.5960 (24) |
| 3-49 | 2 | H | H | Me | $CH_2$-3-$CF_3$Ph | O | 1.5296 (26) |
| 3-50 | 2 | H | H | Me | C($CH_2CH_2$)-3-Cl-Ph | O | 1.5754 (26) |
| 3-51 | 2 | H | H | Me | n-Bu | O | 1.5252 (25) |
| 3-52 | 2 | H | H | Et | n-Bu | O | 1.5132 (25) |
| 3-53 | 2 | H | H | Me | n-Pr | O | 1.5269 (26) |
| 3-54 | 2 | H | H | Me | $CH_2CF_3$ | O | 1.4971 (25) |
| 3-55 | 2 | H | H | Me | 2-Br-Ph | O | 1.5705 (26) |
| 3-56 | 2 | H | H | Et | 4-F-Ph | O | 1.5281 (27) |
| 3-57 | 2 | H | H | Me | 3-MeO-Ph | O | 1.5800 (27) |
| 3-58 | 2 | H | H | Me | $CH_2$-4-F-Ph | O | 1.5580 (27) |
| 3-59 | 2 | H | H | n-Bu | n-Bu | O | 1.5187 (27) |
| 3-60 | 2 | H | H | Me | 3-Me-Ph | O | 1.5780 (24) |
| 3-61 | 2 | H | H | Me | $CH_2$-3-F-Ph | O | 1.5568 (25) |
| 3-62 | 2 | H | H | Me | 3,4-$F_2$-Ph | O | 112 |
| 3-63 | 2 | H | H | Me | 2-F-6-$CF_3$-Ph | O | 1.5352 (26) |
| 3-64 | 2 | H | H | Me | $CH_2$-3,4-$F_2$-Ph | O | 1.5550 (25) |
| 3-65 | 2 | H | H | Me | $CH_2$-3-Cl-4-F-Ph | O | 1.5708 (24) |
| 3-66 | 2 | H | H | Me | i-Pr | O | 1.5211 (24) |
| 3-67 | 2 | H | H | Me | i-Bu | O | 1.5299 (26) |
| 3-68 | 2 | H | H | Me | 3-F-Ph | O | 1.5486 (25) |
| 3-69 | 2 | H | H | Me | 2,4-$F_2$-Ph | O | 1.5363 (25) |
| 3-70 | 2 | H | H | Me | $CH_2$-4-MeO-Ph | O | 1.5728 (24) |
| 3-71 | 2 | H | H | Me | 4-Ph-Ph | O | 1.5767 (24) |
| 3-72 | 2 | H | H | Me | 3,5-$F_2$-Ph | O | 1.5479 (24) |
| 3-73 | 2 | H | H | Me | 4-Me-Ph | O | 138.9-140.2 |
| 3-74 | 2 | H | H | Me | $CH_2$OMe | O | 1.5340 (24) |
| 3-75 | 2 | H | H | Me | $CH_2$-4-Me-Ph | O | 1.5732 (24) |
| 3-76 | 2 | H | H | Me | 2-MeO-Ph | O | 1.5781 (24) |
| 3-77 | 2 | H | H | Me | 2,4-$Cl_2$-Ph | O | 1.5593 (20) |
| 3-78 | 2 | H | H | Me | 4-F-Ph | O | 1.5620 (21) |
| 3-79 | 2 | H | H | Me | 2,4-$Cl_2$-5-F-Ph | O | 1.5730 (26) |

TABLE 3-1-continued

General Formula (IV-1)

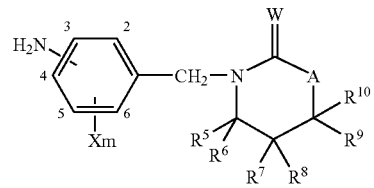

(IV-1)

(m = 0, A = O, $R^5 = R^6$ = H)

| Compound No. | Substituted site | $R^7$ | $R^8$ | $R^9$ | $R^{10}$ | W | Physical properties |
|---|---|---|---|---|---|---|---|
| 3-80 | 2 | H | H | Me | 3-MeO-Ph | O | 1.5800 (27) |
| 3-81 | 2 | H | H | Me | 4-MeO-Ph | O | 1.5710 (19) |
| 3-82 | 2 | H | H | Me | 2-F-4-Meo-Ph | O | 1.5652 (19) |
| 3-83 | 2 | H | H | Me | 3-F-4-Meo-Ph | O | 1.5724 (20) |
| 3-84 | 2 | H | H | Me | $CH_2$-4-Me-Ph | O | 1.5732 (24) |
| 3-85 | 2 | H | H | Me | $CH_2$-4-MeO-Ph | O | 1.5728 (24) |
| 3-86 | 2 | H | H | Me | $CH_2$-3,4-$F_2$-Ph | O | 1.5550 (25) |
| 3-87 | 2 | H | H | Me | $CH_2$-3-Cl-4-F-Ph | O | 1.5708 (24) |
| 3-88 | 2 | H | H | Me | $CH_2$-3-F-Ph | O | 1.5568 (25) |
| 3-89 | 2 | H | H | Me | $CH_2$-4-F-Ph | O | 1.5580 (27) |
| 3-90 | 2 | H | H | Me | 2,4-$Me_2$-Ph | O | 1.5862 (22) |
| 3-91 | 2 | H | H | Me | $CH_2C(Me)_2OMe$ | O | 1.5279 (23) |

TABLE 4

General Formula (IV-2)

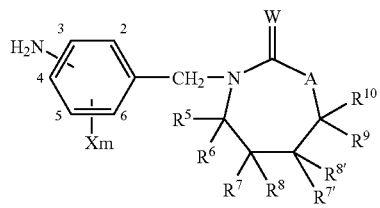

(IV-2)

(m = 0, A = O, $R^5 = R^6 = R^7 = R^8$ = H)

| Compound No. | Substituted site | $R^{7'}$ | $R^{8'}$ | $R^9$ | $R^{10}$ | W | Physical properties |
|---|---|---|---|---|---|---|---|
| 4-1 | 2 | H | H | H | H | O | 1.5480 (22) |
| 4-2 | 2 | H | H | H | H | S | 1.5979 (26) |
| 4-3 | 2 | Me | H | H | H | O | 1.5432 (26) |

TABLE 5-1

General Formula (II-3)

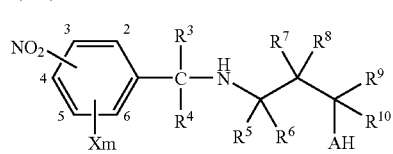

(II-3)

(m = 0, A = O, $R^3 = R^4 = R^5 = R^6$ = H)

| Compound No. | Substituted site | $R^7$ | $R^8$ | $R^9$ | $R^{10}$ | A | Physical properties |
|---|---|---|---|---|---|---|---|
| 5-1 | 2 | H | H | H | H | O | 1.5489 (24) |
| 5-2 | 2 | Me | Me | H | H | O | 1.5265 (23) |
| 5-3 | 2 | H | H | Me | Me | O | 65.3-67.9 |
| 5-4 | 2 | H | H | Me | Et | O | 1.5392 (23) |
| 5-5 | 2 | H | H | Me | $CF_3$ | O | 1.4945 (19) |
| 5-6 | 2 | H | H | Et | $CF_3$ | O | 1.4992 (22) |

TABLE 5-1-continued

General Formula (II-3)

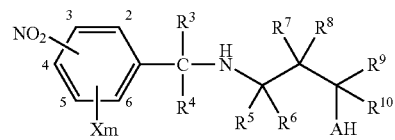

(II-3)

(m = 0, A = O, R³ = R⁴ = R⁵ = R⁶ = H)

| Compound No. | Substituted site | R⁷ | R⁸ | R⁹ | R¹⁰ | A | Physical properties |
|---|---|---|---|---|---|---|---|
| 5-7 | 2 | H | H | Et | Et | O | 1.5245 (20) |
| 5-8 | 2 | H | H | Me | c-Pr | O | 1.5350 (20) |
| 5-9 | 2 | H | H | | (CH₂)₄ | O | 1.5416 (23) |
| 5-10 | 2 | H | H | c-Pr | c-Pr | O | 1.5369 (27) |
| 5-11 | 2 | H | H | Me | Ph | O | 1.5572 (23) |
| 5-12 | 2 | H | H | Me | 2-Cl-Ph | O | 1.5749 (25) |
| 5-13 | 2 | H | H | c-Pr | Ph | O | 1.5604 (26) |
| 5-14 | 2 | H | H | c-Pr | 4-Cl-Ph | O | 1.5571 (25) |
| 5-15 | 2 | H | H | c-Bu | Ph | O | 1.5603 (26) |
| 5-16 | 2 | H | H | Ph | Ph | O | 98.2-100.1 |
| 5-17 | 2 | H | H | CF₃ | Ph | O | 1.5416 (26) |
| 5-18 | 2 | H | H | H | Ph | O | 1.5537 (25) |
| 5-19 | 2 | H | H | H | 2-F-Ph | O | 1.5625 (26) |
| 5-20 | 2 | Me | Me | H | Ph | O | 1.5468 (25) |
| 5-21 | 2 | H | H | H | 2,6-Cl-Ph | O | 86.2 |
| 5-22 | 2 | H | H | H | 2-Me-Ph | O | 1.5696 (19) |
| 5-23 | 2 | H | H | H | 2-CF₃-Ph | O | 69.2-70.3 |
| 5-24 | 2 | H | H | H | 2-Cl-Ph | O | 1.5714 (17) |
| 5-25 | 2 | H | H | Et | Ph | O | 1.5570 (20) |
| 5-26 | 2 | H | H | Me | t-Bu | O | 1.5325 (17) |
| 5-27 | 2 | H | H | CF₃ | CF₃ | O | 67.2 |
| 5-28 | 2 | H | H | H | 2,6-F₂-Ph | O | 1.5606 (18) |
| 5-29 | 2 | H | H | H | 2,6-Me₂-Ph | O | 108.3 |
| 5-30 | 2 | H | H | Me | 1-Me-1-c-Pr | O | 1.5361 (21) |
| 5-31 | 2 | H | H | Me | c-Bu | O | 1.5398 (25) |
| 5-32 | 2 | H | H | Me | 2-CF₃-Ph | O | NMR-1 |
| 5-33 | 2 | H | H | Et | i-Bu | O | 1.5219 (25) |
| 5-34 | 2 | H | H | Me | 2-F-Ph | O | NMR |
| 5-35 | 2 | H | H | Et | i-Pr | O | 1.5276 (25) |
| 5-36 | 2 | H | H | Me | CH₂-2-F-Ph | O | |
| 5-37 | 2 | H | H | Me | 4-Cl-Ph | O | NMR |
| 5-38 | 2 | H | H | Me | CH₂-2,6-Cl₂-Ph | O | |
| 5-39 | 2 | H | H | Et | n-Pr | O | 1.5204 (25) |
| 5-40 | 2 | H | H | Me | neo-Pen | O | 1.5185 (26) |
| 5-41 | 2 | H | H | Me | CH₂-2-Cl-Ph | O | |
| 5-42 | 2 | H | H | n-Pr | n-Pr | O | 1.5145 (24) |
| 5-43 | 2 | H | H | Me | CH₂-4-Cl-Ph | O | |
| 5-44 | 2 | H | H | i-Bu | i-Bu | O | 1.5106 (26) |
| 5-45 | 2 | H | H | Me | CH₂-3-Cl-Ph | O | |
| 5-46 | 2 | H | H | Me | CH₂-3-CF₃-Ph | O | |
| 5-47 | 2 | H | H | Me | C(CH₂CH₂)-3-Cl-Ph | O | |
| 5-48 | 2 | H | H | Me | n-Bu | O | 1.5161 (24) |
| 5-49 | 2 | H | H | Et | n-Bu | O | 1.5182 (25) |
| 5-50 | 2 | H | H | Me | n-Pr | O | 1.5255 (26) |
| 5-51 | 2 | H | H | Me | CH₂CF₃ | O | 1.4995 (28) |
| 5-52 | 2 | H | H | Me | 2-Br-Ph | O | NMR |
| 5-53 | 2 | H | H | Et | 4-F-Ph | O | 1.5422 (26) |
| 5-54 | 2 | H | H | Me | 3-MeO-Ph | O | 1.5542 (27) |
| 5-55 | 2 | H | H | n-Bu | n-Bu | O | 1.5010 (27) |
| 5-56 | 2 | H | H | Me | 3-Me-Ph | O | 1.5491 (25) |
| 5-57 | 2 | H | H | Me | 3,4-F₂-Ph | O | 1.5382 (24) |
| 5-58 | 2 | H | H | Me | i-Pr | O | 1.5220 (25) |
| 5-59 | 2 | H | H | Me | i-Bu | O | 1.5223 (25) |
| 5-60 | 2 | H | H | Me | 3-F-Ph | O | 1.5442 (25) |
| 5-61 | 2 | H | H | Me | 2,4-F₂-Ph | O | 1.5289 (25) |
| 5-62 | 2 | H | H | Me | 4-Ph-Ph | O | 1.5735 (23) |
| 5-63 | 2 | H | H | Me | 3,5-F₂-Ph | O | 1.5358 (26) |
| 5-64 | 2 | H | H | Me | 4-Me-Ph | O | 1.5525 (23) |
| 5-65 | 2 | H | H | Me | CH₂OMe | O | 1.5225 (25) |
| 5-66 | 2 | H | H | Me | 2-MeO-Ph | O | 1.5742 (24) |
| 5-67 | 2 | H | H | Me | 2,4-Cl₂-Ph | O | 1.5635 (21) |
| 5-68 | 2 | H | H | Me | 4-F-Ph | O | 1.5421 (20) |
| 5-69 | 2 | H | H | Me | 2,4-Cl₂-5-F-Ph | O | 1.5600 (23) |
| 5-70 | 2 | H | H | Me | 3-MeO-Ph | O | 1.5746 (26) |
| 5-71 | 2 | H | H | Me | 4-MeO-Ph | O | 1.5636 (22) |
| 5-72 | 2 | H | H | Me | 2-F-4-MeO-Ph | O | 1.5339 (22) |

TABLE 5-1-continued

General Formula (II-3)

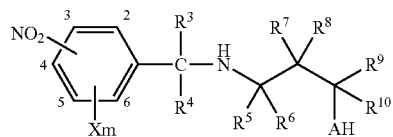

(II-3)

(m = 0, A = O, $R^3 = R^4 = R^5 = R^6$ = H)

| Compound No. | Substituted site | $R^7$ | $R^8$ | $R^9$ | $R^{10}$ | A | Physical properties |
|---|---|---|---|---|---|---|---|
| 5-73 | 2 | H | H | Me | 3-F-4-MeO-Ph | O | 1.5350 (22) |
| 5-74 | 2 | H | H | Me | $CH_2$-4-Me-Ph | O | 1.5502 (26) |
| 5-75 | 2 | H | H | Me | $CH_2$-4-MeO-Ph | O | 1.5558 (26) |
| 5-76 | 2 | H | H | Me | $CH_2$-3,4-$F_2$-Ph | O | 1.5396 (24) |
| 5-77 | 2 | H | H | Me | $CH_2$-3-Cl-4-F-Ph | O | 1.5508 (26) |
| 5-78 | 2 | H | H | Me | $CH_2$-3-F-Ph | O | 1.5449 (26) |
| 5-79 | 2 | H | H | Me | $CH_2$-4-F-Ph | O | 1.5468 (26) |
| 5-80 | 2 | H | H | Me | 2,4-$Me_2$-Ph | O | 1.5556 (21) |
| 5-81 | 2 | H | H | Me | 4-Br-Ph | O | 1.5615 (19) |
| 5-82 | 2 | H | H | Me | $CH_2C(Me)_2OMe$ | O | 1.5241 (20) |

TABLE 6

General Formula (II4)

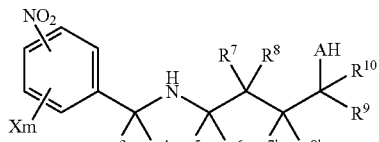

(II-4)

(m = 0, A = O, $R^3 = R^4 = R^5 = R^6 = R^7 = R^8$ = H)

| Compound No. | Substituted site | $R^{7'}$ | $R^{8'}$ | $R^9$ | $R^{10}$ | Physical properties |
|---|---|---|---|---|---|---|
| 6-1 | 2 | H | H | H | H | 1.5431 (24) |
| 6-2 | 2 | Me | H | H | H | 1.5372 (24) |

TABLE 7

| Compound No. | $^1$H-NMR (CDCl$_3$/TMS, δ value ppm) |
|---|---|
| 5-32 | 7.96(1H, dd), 7.77(1H, d), 7.72(1H, d), 7.57(1H, ddd), 7.51(1H, t), 7.46(1H, dd), 7.42(1H, ddd), 7.34(1H, t), 3.93(1H, d), 3.82(1H, d), 2.95(1H, ddd), 2.59(1H, ddd), 2.35(1H, ddd), 2.02(1H, ddd), 1.60(3H, s) |
| 5-34 | 7.98(1H, d), 7.77(1H, ddd), 7.58(1H, ddd), 7.45(1H, d), 7.43(1H, ddd), 7.22(1H, dd), 7.15(1H, ddd), 6.99(1H, dd), 3.92(1H, d), 3.83(1H, d), 2.89(1H, ddd), 2.43(1H, ddd), 2.28(1H, ddd), 2.01(1H, ddd), 1.56(3H, s) |
| 5-37 | 7.98(1H, d), 7.58(1H, dd), 7.45(2H, m), 7.38(1H, d), 7.29(1H, d), 3.94(1H, d), 3.85(1H, d), 2.86(1H, ddd), 2.50(1H, ddd), 2.20-1.91(2H, m), 1.48(3H, s) |
| 5-52 | 8.02(1H, dd), 7.98(1H, dd), 7.58(1H, ddd), 7.56(1H, dd), 7.47-7.40(2H, m), 7.33(1H, ddd), 7.09(1H, ddd), 3.90(1H, d), 3.81(1H, d), 2.92-2.82(1H, m), 2.38(1H, m), 1.98(1H, m), 1.68(3H, s) |

The haloalkylsulfonanilide derivatives or the salts thereof of the present invention are useful for controlling, for example, annual, biennial and perennial weeds occurring in paddy field, upland field, orchard, damp ground, etc., such as barnyard grass (*Echinochloa crus-qalli* Beauv., an annual gramineous grass which is an injurious weed of paddy fields), false pimpernel (*Lindernia pyxidaria*, an annual witchweed which is an injurious weed of paddy fields), monochoria (*Monochoria vaginalis*, an annual pickerelweed which is an injurious weed of paddy fields), (*Monochoria korsakowii*, an annual pickerelweed which is an injurious weed of paddy fields), ammannia (*Ammannia multiflora* Roxb., an annual lythraceous weed which is an injurious weed of paddy fields), umbrella plant (*Cyperus difformis* L., an annual cyperaceous grass which is an injurious weed of paddy fields), slender spikerush (*Eleocharis acicularis* Roem. et Schult, a perennial cyperaceous grass which is an injurious weed of paddy fields and which grows also in swamps and waterways), starfruit (*Sagittaria trifolia* L., an injurious perennial weed of Alismataceae family which grows in paddy fields, swamps and ditches), arrowhead (*Sagittaria pygmaea* Miq., an injurious perennial weed of Alismataceae family which grows in paddy fields, swamps and ditches), bulrush (*Scirpus juncoides* var. ohwianus, a perennial cyperaceous weed which grows in paddy fields, swamps and ditches), kuroguwai (*Eleocharis kuroguwai*, a perennial cyperaceous weed which grows in paddy fields, swamps and ditches), foxtail grass (*Alopecurus aequalis* var. amurensis Ohwi, gramineous grass which grows in upland fields and low swamps), wild oats (*Avena fatua* L., a biennial graminous grass which grows in plains, waste lands and upland fields), mugwort (*Artemisia princeps* Pamp., a perennial composite grass which grows in cultivated and uncultivated fields and mountains), large crabgrass (*Digitaria adscendens* Henr., an annual gramineous grass which is an injurious weed of upland fields and orchards), Gishigishi or Japanese dock (*Rumex japonicus* Houtt., a perennial polygonaceous weed which grows in upland fields and roadsides), flatsedge (*Cyperus iria* L., an annual cyperaceous weed which is an injurios weed of upland fields), slender amaranth (*Amaranthus viridis* L., an annual weed of Amaranthaceae family which grows in vacant lands, roadsides and upland fields), cocklebur (*Xanthium strumarium* L., an injurious annual composite weed which grows in upland fields), velvetleaf (*Abutilon theophrasti* L., an injurious annual weed of Malvaceae family which grows in upland fields), jimsonweed (*Datura stramonium*, an annual nightshade weed which is an injurious weed of upland fields), bird's eye speedwell (*Veronica persica* Poir., an injurious biennual weed of Scrophulariaceae family which grows in upland fields) and cleavers (*Galium spurium* L., an injurious annual weed of Rubiaceae family which grows in upland fields and orchards), etc. They are effective for weed control in paddy field in particular and have excellent performance as herbicides for paddy fields because the width in selectivity between rice-paddy weed is wide.

Since the haloalkylsulfonanilide derivatives or the salts thereof of the present invention exhibit an excellent controlling effect on weeds pre- or post-emergence, the characteristic physiological activities of the herbicide composition of the present invention can be effectively manifested by treating fields with the herbicides before planting useful plants therein, or after planting useful plants therein (including the case in which useful plants are already planted as in orchards) but during the period from the initial stage of emergence of weeds to their growth stage. However, the application of the herbicide composition of the present invention is not restricted only to the modes mentioned above. The herbicide composition of the present invention can be applied to control not only weeds which grow in paddy fields but also, for example, weeds which grow in other places such as uplands, temporarily non-cultivated paddy fields and upland fields, ridges between fields, agricultural pathways, waterways, lands constructed for pasture, graveyards, roads, playgrounds, unoccupied areas around buildings, developed lands, railways, forests. The treatment of target fields with the herbicides is most effective in economy when the treatment is made by the initial stage of emergence of weeds. However, the treatment is not restricted thereto and can be carried out even during the growth stage of weeds.

For applying the haloalkylsulfonanilide derivatives or the salts thereof of the present invention as herbicides, they are preferably formulated into a form convenient to use according to the procedure conventionally employed for preparing agricultural chemicals. That is, the haloalkylsulfonanilide derivatives represented by the formula (I) or the salts thereof are mixed with a suitable inert carrier and, as required, further with an adjuvant, in an appropriate ratio, and the mixture is made into a desired form of preparation, such as suspension, emulsion, emulsifiable concentrate, solution, wettable powder, water dispersible granule, granules, dust, tablets jumbo formulations, pack formulations, through dissolution, dispersion, suspension, mixing, impregnation, adsorption or adhesion.

The inert carriers usable in the present invention may be solid or liquid, and examples of materials usable as the solid carriers include vegetable powders (for example, soybean flour, cereal flour, wood flour, bark flour, saw dust, powdered tobacco stalks, powdered walnut shells, bran, powdered cellulose, extraction residues of vegetables), powdered synthetic polymers of resins, clays (for example, kaolin, bentonite and acid clay), talcs (for example, talc and pyrophyllite), silica powders or flakes [for example, diatomaceous earth, silica sand, mica and white carbon (i.e. highly dispersed silicic acid, also called finely divided hydrated silica or hydrated silicic acid)], activated carbon, natural mineral materials (for example, powdered sulfur, powdered pumice, attapulgite and zeolite), calcined diatomaceous earth, ground brick, fly ash, sand, plastic carriers (for example, polyethylene, polypropylene, polyvinylidene chloride), inorganic mineral powders such as calcium carbonate powder and calcium phosphate powder, chemical fertilizers such as ammonium sulfate, ammonium phosphate, ammonium nitrate, urea, and ammonium chloride and compost. These materials can be used singly or as a mixture of two or more kinds.

Materials usable as the liquid carriers are selected not only from those which have solvency by themselves but also from those which have no solvency but capable of dispersing the active ingredient compound with the aid of adjuvants. Typical examples of the liquid carriers, which can be used alone or in combination of two or more, are water, alcohols (for example, methanol, ethanol, isopropanol, butanol and ethylene glycol), ketones (for example, acetone, methyl ethyl ketone, methyl isobutyl ketone, diisobutyl ketone and cyclohexanone), ethers (for example, ethyl ether, dioxane, cellosolve, dipropyl ether and tetrahydrofuran), aliphatic hydrocarbons (for example, kerosene and mineral oils), aromatic hydrocarbons (for example, benzene, toluene, xylene, solvent naphtha and alkylnaphthalenes), halogenated hydrocarbons (for example, dichloroethane, chloroform and carbon tetrachloride), esters (for example, ethyl acetate, diisopropyl phthalate, dibutyl phthalate and dioctyl phthalate), amides (for example, dimethylformamide, diethylformamide and dimethylacetamide), nitriles (for example, acetonitrile) and dimethyl sulfoxide.

The other adjuvants include typical adjuvants as exemplified below, and they can be used according to respective purposes. In some cases, they can be used alone or in combination of two or more, or in other cases it is possible to use no adjuvants. For the purpose of emulsifying, dispersing, solubilizing and/or wetting the active ingredient compounds, there can be used surface active agents, for example, polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninsulfonates and higher alcohol sulfate esters.

For the purpose of imparting stable dispersion, tackiness and/or bonding property to the active ingredient compounds, there may be used adjuvants such as casein, gelatin, starch, methyl cellulose, carboxy methyl cellulose, gum arabic, polyvinyl alcohol, turpentine, bran oil, bentonite and ligninsulfonates. For the purpose of improving the flow properties of solid herbicidal compositions, there may be used adjuvants such as waxes, stearates and alkyl phosphates. Adjuvants such as naphthalenesulfonic acid condensation products and polyphosphates may be used as peptizers in dispersible herbicidal compositions. Adjuvants such as silicone oils may be used as defoaming agent.

The content of the active ingredient compound for the whole herbicide of the present invention is not limited particularly and may be varied as required, and for example, for the preparation of a powdered or granulated product, the content is preferably 0.1 to 50% by mass, more preferably 0.5 to 10% by mass, and for the preparation of emulsifiable concentrate, wettable powder, water dispersible granule, the content is preferably 0.1 to 90% by mass, more preferably 0.5 to 50% by mass.

For controlling various weeds or inhibiting their growth, the herbicides of the present invention are applied as is or after appropriately diluted with or suspended in water or other media, in an amount effective for controlling weeds or inhibiting their growth in the area where the emergence or growth of the weeds is undesirable. For example, in the case of upland fields or non-cultivated fields, they can be applied to the foliage and stalks or to the soil, and in the case of paddy fields, they can be applied to the paddy field water.

The used amount of herbicides of the present invention varies depending on various factors, for example, the purpose of application, the kinds of target weeds, the growth states of crops, the emergence tendency of weeds, weather, environmental conditions, the form of the herbicides used, the mode of application, the type or state of application site and the time of application but the amount is selected appropriately according to the purpose from the range of 0.1 g to 10 kg in terms of the amount of active ingredient compound per hectare.

In addition, the herbicides comprising haloalkylsulfonanilide derivative or the salts thereof of the present invention as an active ingredient can be used as a mixture with an other compound having the herbicidal activity for the purpose of expanding the herbicidal spectrum, enhancing the herbicidal activity and so on. Furthermore, the herbicide compositions of the present invention can be mixed and used with an insecticide or a fungicide.

EXAMPLES

Hereinbelow, the present invention is specifically described by way of Examples, Formulation Examples and Test Examples but the present invention is not limited to these.

Here, [1,3]-oxazinan-2-one and [1,3]-oxazepan-2-one represent the following structure.

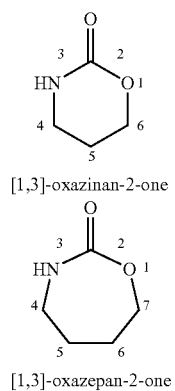

[Formula 6]

[1,3]-oxazinan-2-one

[1,3]-oxazepan-2-one

Example 1

Production of 3-[2-(trifluoromethanesulfonylamino) benzyl]-[1,3]-oxazinan-2-one (Compound No. 1-1)
1-1) Production of 3-(2-nitrobenzyl)-[1,3]-oxazinan-2-one 3-(2-Nitrobenzylamino)-1-propanol (1.03 g, 4.90 mmol) was dissolved in chloroform (20 ml) and the reaction solution was cooled to 0° C. Then triethylamine (1.98 g, 19.6 mmol), triphosgene (0.58 g, 1.95 mmol) were added thereto and the mixture was stirred at the same temperature for 1.5 hours. The reaction mixture was added with water and extracted with ethyl acetate and after the organic layer was washed with a saturated brine, it was dried over anhydrous sodium sulfate, and the solvent was evaporated under reduced pressure. The residue was purified by silica gel column chromatography (hexane:ethyl acetate=1:4) and 3-(2-nitrobenzyl)-[1,3]-oxazinan-2-one (0.29 g) was obtained.
Yield: 25%
Physical properties: mp. 137.8° C.

1-2) Production of 3-(2-aminobenzyl)-[1,3]-oxazinan-2-one (Compound No. 3-1)

3-(2-Nitrobenzyl)-[1,3]-oxazinan-2-one (0.24 g, 1.02 mmol), iron powder (0.28 g, 5.02 mmol), ammonium chloride (0.03 g, 0.56 mmol) were suspended in ethanol (10 ml) and water (5 ml) and heated to reflux for one hour. After cooling to room temperature, the reaction mixture was filtered with suction and extracted with ethyl acetate. The organic layer was washed with a saturated brine and then dried over anhydrous sodium sulfate, and 3-(2-aminobenzyl)-[1,3]-oxazinan-2-one was obtained by evaporating the solvent under reduced pressure (0.20 g).
Yield: 95%
Physical properties: $n_D$ 1.5489 (22° C.)

1-3) Production of 3-[2-(trifluoromethanesulfonylamino)benzyl]-[1,3]-oxazinan-2-one (Compound No. 1-1)

3-(2-Aminobenzyl)-[1,3]-oxazinan-2-one (0.17 g, 0.83 mmol) and triethylamine (0.09 g, 0.89 mmol) were dissolved in chloroform (10 ml) and the reaction solution was cooled to −10° C. Trifluoromethanesulfonic anhydride (0.24 g, 0.85 mmol) was slowly added dropwise thereto and stirred at temperature as is for 30 minutes. The reaction mixture was poured into iced water and pH was adjusted from 3 to 4 with 0.5 N hydrochloric acid water and the reaction mixture was extracted with ethyl acetate. The solvent was evaporated under reduced pressure after the organic layer was dried over anhydrous sodium sulfate. The residue was purified by silica gel column chromatography (hexane:ethyl acetate=1:4) to obtain 3-[2-(trifluoromethanesulfonylamino)benzyl]-[1,3]-oxazinan-2-one (0.20 g).
Yield: 71%
Physical properties: $n_D$ 1.4952 (22° C.)

Example 2

Production of 3-{2-[N-(propoxycarbonyl)-N-(trifluoromethanesulfonyl)amino]benzyl)-[1,3]-oxazinan-2-one (Compound No. 1-4)

3-[2-(Trifluoromethanesulfonylamino)benzyl]-[1,3]-oxazinan-2-one (0.13 g, 0.38 mmol) and sodium hydrogen carbonate (0.06 g, 0.71 mmol) was suspended in acetonitrile (15 ml), added with propyl chloroformate (0.09 g, 0.77 mmol) and heated to reflux for six hours. After cooling to room temperature, the reaction mixture was added with water and extracted with ethyl acetate. The organic layer was washed with a saturated brine and then dried over anhydrous sodium sulfate, and the solvent was evaporated under reduced pressure. The residue was purified by silica gel column chromatography (hexane:ethyl acetate=1:4) to obtain 3-{2-[N-(propoxycarbonyl)-N-(trifluoromethanesulfonyl)amino] benzyl)-[1,3]-oxazinan-2-one (0.11 g).
Yield: 68%
Physical properties: $n_D$ 1.4977 (24° C.)

Example 3

Production of 6-phenyl-3-[2-(trifluoromethanesulfonylamino)benzyl]-[1,3]-oxazinan-2-one (Compound No. 1-239) 3-1) Production of 3-(2-nitrobenzyl)-6-phenyl-[1,3]-oxazinan-2-one 3-(2-Nitrobenzylamino)-1-phenylpropanol (3.00 g, 10.5 mmol), triethylamine (4.24 g, 42.0 mmol) were dissolved in toluene (50 ml). Under ice cooled condition, a solution in which triphosgene (1.24 g, 4.19 mmol) was dissolved in toluene (5 ml) was slowly added dropwise thereto and heated to reflux for six hours after stirred at room temperature for one hour. The reaction mixture was poured into water and, after standing to cool, extracted with ethyl acetate. The organic layer was washed with 0.1N hydrochloric acid water and then dried over anhydrous sodium sulfate and the solvent was evaporated under reduced pressure. The residue was washed with a mixture of ether-ethyl acetate (1:2) to obtain 3-(2-nitrobenzyl)-6-phenyl-[1,3]-oxazinan-2-one (1.70 g).
Yield: 52%
Physical properties: mp. 117.8° C.

3-2) Production of 3-(2-aminobenzyl)-6-phenyl-[1,3]-oxazinan-2-one (Compound No. 3-22)

3-(2-Nitrobenzyl)-6-phenyl-[1,3]-oxazinan-2-one (1.59 g, 5.10 mmol), iron powder (1.42 g, 25.4 mmol), ammonium chloride (0.14 g, 2.62 mmol) were suspended in ethanol (30 ml) and water (15 ml) and heated to reflux for 1.5 hours. After cooling to room temperature, the reaction mixture was filtered with suction and extracted with ethyl acetate. The organic layer was washed with a saturated brine and then dried over anhydrous sodium sulfate, and 3-(2-aminobenzyl)-6-phenyl-[1,3]-oxazinan-2-one (1.43 g) was obtained by evaporating the solvent under reduced pressure.
Yield: 99%
Physical properties: $n_D$ 1.5719 (26° C.)

3-3) Production of 6-phenyl-3-[2-(trifluoromethanesulfonylamino)benzyl]-[1,3]-oxazinan-2-one (Compound No. 1-239)

3-(2-Aminobenzyl)-6-phenyl-[1,3]-oxazinan-2-one (1.33 g, 4.72 mmol) and triethylamine (0.50 g, 4.95 mmol) were dissolved in chloroform (20 ml) and the reaction solution was cooled to −10° C. Trifluoromethanesulfonic anhydride (1.40 g, 4.96 mmol) was slowly added dropwise and stirred at temperature as is for two hours. The reaction mixture was poured into iced water and pH was adjusted from 3 to 4 with 0.5 N hydrochloric acid water and the reaction mixture was extracted with ethyl acetate. The solvent was evaporated under reduced pressure after the organic layer was dried over anhydrous sodium sulfate. The residue was purified by silica gel column chromatography (hexane:ethyl acetate=2:1) to obtain 6-phenyl-3-[2-(trifluoromethanesulfonylamino)benzyl]-[1,3]-oxazinan-2-one (1.70 g).
Yield: 87%
Physical properties: mp. 152.0° C.

Example 4

Production of 6-phenyl-3-{2-[N-(ethoxymethyl)-N-(trifluoromethanesulfonyl)amino]benzyl)-[1,3]-oxazinan-2-one (Compound No. 1-248)

6-Phenyl-3-[2-(trifluoromethanesulfonylamino)benzyl]-[1,3]-oxazinan-2-one (0.20 g, 0.48 mmol) and sodium hydrogen carbonate (0.08 g, 0.85 mmol) were suspended in acetonitrile (10 ml), added with chloromethylethyl ether (0.07 g, 0.83 mmol) and heated to reflux for three hours. After cooling to room temperature, the reaction mixture was added with water and extracted with ethyl acetate. The organic layer was washed with a saturated brine and then dried over anhydrous sodium sulfate, and the solvent was evaporated under reduced pressure. The residue was purified by silica gel column chromatography (hexane:ethyl acetate=2:1) to obtain 6-phenyl-3-{2-[N-(ethoxymethyl)-N-(trifluoromethanesulfonyl)amino]benzyl)-[1,3]-oxazinan-2-one (0.17 g).
Yield: 75%
Physical properties: mp. 115.6° C.

Example 5

Production of 6-methyl-3-[2-(trifluoromethanesulfonylamino)benzyl]-[1,3]-oxazepan-2-one (Compound No. 2-23)

5-1) Production of 6-methyl-3-(2-nitrobenzyl)-[1,3]-oxazepan-2-one

2-Methyl-4-(2-nitrobenzylamino)butanol (5.00 g, 21.0 mmol), triethylamine (8.49 g, 84.1 mmol) were dissolved in toluene (50 ml). Under ice cooled condition, a solution in which triphosgene (2.50 g, 8.42 mmol) was dissolved in toluene (10 ml) was slowly added dropwise thereto and heated to reflux for six hours after stirred at room temperature for one hour. The reaction mixture was poured into water and, after standing to cool, extracted with ethyl acetate. The organic layer was washed with 0.1 N hydrochloric acid water and then dried over anhydrous sodium sulfate, and the solvent was evaporated under reduced pressure. The residue was purified by silica gel column chromatography (hexane:ethyl acetate=2:1) to obtain 6-methyl-3-(2-nitrobenzyl)-[1,3]-oxazepan-2-one (2.00 g).
Yield: 36%
Physical properties: $n_D$ 1.5392 (26° C.)

5-2) Production of 3-(2-aminobenzyl)-6-methyl-[1,3]-oxazepan-2-one (Compound No. 4-3)

6-Methyl-3-(2-nitrobenzyl)-[1,3]-oxazepan-2-one (1.91 g, 7.23 mmol), iron powder (2.02 g, 36.2 mmol), ammonium chloride (0.19 g, 3.55 mmol) were suspended in ethanol (30 ml) and water (15 ml) and heated to reflux for one hour. After cooling to room temperature, the reaction mixture was filtered with suction and extracted with ethyl acetate. The organic layer was washed with a saturated brine and then dried over anhydrous sodium sulfate, and 3-(2-aminobenzyl)-6-methyl-[1,3]-oxazepan-2-one (1.02 g) was obtained by evaporating the solvent under reduced pressure.
Yield 60%
Physical properties: $n_D$ 1.5432 (26° C.)

5-3) Production of 6-methyl-3-[2-(trifluoromethanesulfonylamino)benzyl]-[1,3]-oxazepan-2-one (Compound No. 2-23)

3-(2-Aminobenzyl)-6-methyl-[1,3]-oxazepan-2-one (0.95 g, 4.06 mmol) and triethylamine (0.43 g, 4.26 mmol) were dissolved chloroform (25 ml) and the reaction solution was cooled to −10° C. Trifluoromethanesulfonic anhydride (1.20 g, 4.26 mmol) was slowly added dropwise thereto and stirred at temperature as is for two hours. The reaction mixture was poured into iced water and pH was adjusted from 3 to 4 with 0.5 N hydrochloric acid water and the reaction mixture was extracted with ethyl acetate. The solvent was evaporated under reduced pressure after the organic layer was dried over anhydrous sodium sulfate. The residue was purified by silica gel column chromatography (hexane:ethyl acetate=2:1) to obtain 6-methyl-3-[2-(trifluoromethanesulfonylamino)benzyl]-[1,3]-oxazepan-2-one (1.10 g).
Yield: 74%
Physical properties: $n_D$ 1.4945 (26° C.)

Example 6

Production of 3-(2-[N-(isobutoxycarbonyl)-N-(trifluoromethanesulfonyl)amino]benzyl)-6-methyl-[1,3]-oxazepan-2-one (Compound No. 2-28)

6-Methyl-3-[2-(trifluoromethanesulfonylamino)benzyl]-[1,3]-oxazepan-2-one (0.15 g, 0.41 mmol) and sodium hydrogen carbonate (0.06 g, 0.71 mmol) were suspended in acetonitrile (10 ml), added with isobutyl chloroformate (00.10 g, 0.73 mmol) and heated to reflux for three hours. After cooling to room temperature, the reaction mixture was added with water and extracted with ethyl acetate. The ethyl acetate layer was washed with a saturated brine and then dried over anhydrous sodium sulfate, and the solvent was evaporated under reduced pressure. The residue was purified by silica gel column chromatography (hexane:ethyl acetate=3:1) to obtain 3-(2-[N-(isobutoxycarbonyl)-N-(trifluoromethanesulfonyl)amino]benzyl)-6-methyl-[1,3]-oxazepan-2-one (0.10 g).
Yield: 52%
Physical properties: $n_D$ 1.4898 (25° C.)

Example 7

Production of 5,5-dimethyl-3-[2-(trifluoromethanesulfonylamino)benzyl]-[1,3]-oxazinan-2-thione (Compound No. 1-34)

7-1) Production of 5,5-dimethyl-3-(2-nitrobenzyl)-[1,3]-oxazinan-2-thione 2,2-Dimethyl-3-(2-nitrobenzylamino)-1-propanol (1.07 g, 4.50 mmol) was dissolved in chloroform (20 ml) and the reaction solution was cooled to 0° C. Then triethylamine (1.82 g, 18.0 mmol), thiophosgene (0.52 g, 4.50 mmol) was added thereto and stirred at a temperature as is for two hours and at room temperature for one hour. The reaction mixture was added with water, stirred at room temperature for one hour and then extracted with ethyl acetate. The organic layer was washed with a saturated brine and then dried over anhydrous sodium sulfate, and the solvent was evaporated under reduced pressure. The residue was purified by silica gel column chromatography (hexane:ethyl acetate=1:1) to obtain 5,5-dimethyl-3-(2-nitrobenzyl)-[1,3]-oxazinan-2-thione (1.12 g).
Yield: 89%
Physical properties: $n_D$ 1.5759 (21° C.)

7-2) Production of 3-(2-aminobenzyl)-5,5-dimethyl-[1,3]-oxazinan-2-thione (Compound No. 3-4)

5,5-Dimethyl-3-(2-nitrobenzyl)-[1,3]-oxazinan-2-thione (1.06 g, 3.79 mmol), iron powder (1.06 g, 19.0 mmol), ammonium chloride (0.10 g, 1.87 mmol) were suspended in ethanol (20 ml) and water (10 ml) and heated to reflux for one hour. After cooling to room temperature, the reaction mixture was filtered with suction and extracted with ethyl acetate. The organic layer was washed with a saturated brine and then dried over anhydrous sodium sulfate, and the solvent was evaporated under reduced pressure to obtain 3-(2-aminobenzyl)-5,5-dimethyl-[1,3]-oxazinan-2-thione (0.60 g).
Yield: 63%
Physical properties: Melting point 90.8-92.1° C.

7-3) Production of 5,5-dimethyl-3-[2-(trifluoromethanesulfonylamino)benzyl]-[1,3]-oxazinan-2-thione (Compound No. 1-34)

After 3-(2-aminobenzyl)-5,5-dimethyl-[1,3]-oxazinan-2-thione (0.54 g, 2.16 mmol) and triethylamine (0.23 g, 2.28 mmol) was dissolved in chloroform (15 ml), the reaction solution was cooled to −10° C. Then trifluoromethanesulfonic anhydride (0.64 g, 2.28 mmol) was added dropwise thereto and stirred at temperature as is for one hour. The reaction mixture was added with dilute hydrochloric acid and extracted with ethyl acetate. The solvent was evaporated under reduced pressure after the organic layer was dried over anhydrous sodium sulfate. The residue was purified by silica gel column chromatography (hexane:ethyl acetate=2:1) to obtain 5,5-dimethyl-3-[2-(trifluoromethanesulfonylamino)benzyl]-[1,3]-oxazinan-2-thione (0.57 g).
Yield: 69%
Physical properties: Melting point 129.9° C.

Example 8

Production of 5,5-dimethyl-3-(2-[N-(methoxycarbonyl)-N-(trifluoromethanesulfonyl)amino]benzyl)-[1,3]-oxazinane-2-thione (Compound No. 1-35)

5,5-dimethyl-3-[2-(trifluoromethanesulfonylamino)benzyl]-[1,3]-oxazinan-2-thione (0.15 g, 0.39 mmol) and sodium hydrogen carbonate (0.05 g, 0.60 mmol) were suspended in acetonitrile (10 ml), added with methyl chloroformate (0.06 g, 0.60 mmol) and heated to reflux for three hours. After cooling to room temperature, the reaction mixture was added with water and extracted with ethyl acetate. The solvent was evaporated under reduced pressure after the organic layer was dried over anhydrous sodium sulfate. The residue was purified by silica gel column chromatography (hexane:ethyl acetate=1:1) to obtain 5,5-dimethyl-3-(2-[N-(methoxycarbonyl)-N-(trifluoromethanesulfonyl)amino]benzyl)-[1,3]-oxazinane-2-thione (0.08 g).
Yield: 47%
Physical properties: $n_D$ 1.5295 (26° C.)

Referential Example 1

Production of 3-(2-nitrobenzylamino) propanol

3-Aminopropanol (3.94 g, 52.5 mmol) and triethylamine (1.77 g, 17.5 mmol) were dissolved in tetrahydrofuran (30 ml) and added with 2-nitrobenzyl chloride (3.00 g, 17.5 mmol) at room temperature. After heated to reflux for seven hours, the reaction mixture was allowed to cool and poured into 1N hydrochloric acid water and extracted with ether. The aqueous layer was adjusted to pH 9 with a saturated sodium hydrogen carbonate aqueous solution and then extracted with ethyl acetate. The organic layer was washed with a saturated brine and then dried over anhydrous sodium sulfate, and the solvent was evaporated under reduced pressure to obtain 3-(2-nitrobenzylamino)propanol (1.22 g).
Yield: 33%
Physical properties: $n_D$ 1.5489 (24° C.)

Referential Example 2

Production of 3-(2-nitrobenzylamino)-1-phenylpropanol 2-1) Production of 3-hydroxy-N-(2-nitrobenzyl)-3-phenyl propionic acid amide 2-Nitrobenzyl amine hydrochloride (2.27 g, 12.0 mmol), 3-hydroxy-3-phenyl propionic acid (2.00 g, 12.0 mmol), triethylamine (1.34 g, 13.3 mmol) were added to tetrahydrofuran (50 ml) and the reaction mixture was ice cooled. Under ice cooled condition, 4-(4,6-dimethoxy-1,3,5-triazin-2-yl)-4-methylmorpholinium chloride (3.33 g, 12.0 mmol) was added thereto and stirred at room temperature for five hours. The reaction mixture was poured into dilute hydrochloric acid water and extracted with ethyl acetate. The organic layer was washed with a saturated brine and then dried over anhydrous sodium sulfate, and the solvent was evaporated under reduced pressure. The obtained crude crystal was washed with a mixture of hexane-ether (2:1) to obtain 3-hydroxy-N-(2-nitrobenzyl)-3-phenyl propionic acid amide (3.32 g).

Yield: 92%

Physical properties: Melting point 145.1° C.

2-2) Production of 3-(2-nitrobenzylamino)-1-phenylpropanol

3-Hydroxy-N-(2-nitrobenzyl)-3-phenyl propionic acid amide (3.19 g, 10.6 mmol) was dissolved in tetrahydrofuran (50 ml) and under ice cooled condition, 1 M tetrahydrofuran-borane tetrahydrofuran solution (27.0 ml, 27.0 mmol) was added dropwise thereto. After the dropwise addition was finished, the reaction mixture was returned to room temperature and stirred for one hour, then heated to reflux for six hours and allowed to cool. Methanol (30 ml) was added thereto under ice cooled condition and heated to reflux for 30 minutes. After allowed to cool, the solvent was evaporated and 0.5 N hydrochloric acid water (30 ml) was added. After extracted with diethyl ether, the aqueous layer was adjusted to pH 8 with a saturated sodium hydrogen carbonate aqueous solution and extracted with ethyl acetate. The organic layer was dried over anhydrous sodium sulfate and the solvent was evaporated under reduced pressure to obtain 3-(2-nitrobenzylamino)-1-phenylpropanol.

Yield: 99%

Physical properties: $n_D$ 1.5537 (25° C.)

Referential Example 3

Production of 2-methyl-4-(2-nitrobenzylamino)butanol

2-Nitrobenzaldehyde (7.33 g, 48.5 mmol) and 4-amino-2-methylbutanol (5.00 g, 48.5 mmol) were dissolved in toluene (50 ml) and heated to reflux for two hours with Dean Stark dehydration apparatus. After allowed to cool, the solvent was evaporated under reduced pressure. The obtained concentrate was dissolved in methanol (100 ml), added with sodium borohydride (2.75 g, 72.8 mmol) under ice cooled condition and stirred at the same temperature for two hours. The reaction mixture was further stirred at room temperature for two hours, adjusted to pH 4 by adding 1N hydrochloric acid, and the solvent was evaporated under reduced pressure. Water (30 ml) was added to dissolve the concentrate and after extracted with ethyl acetate, pH was adjusted to 8 by added a saturated sodium hydrogen carbonate aqueous solution and extracted with ethyl acetate. The organic layer was dried over anhydrous sodium sulfate and the solvent was evaporated under reduced pressure to obtain 2-methyl-4-(2-nitrobenzylamino)butanol (11.12 g).

Yield: 96%

Physical properties: $n_D$ 1.5372 (24° C.)

Typical formulation examples and test examples of the present invention are shown below but the present invention is not restricted to these examples. In the formulation examples, parts means parts by mass.

Formulation Example 1

Emulsifiable Concentrate

| | |
|---|---|
| Compound of the present invention | 10 parts |
| Xylene | 70 parts |
| N-methylpyrrolidone | 10 parts |
| Mixture of polyoxyethylene nonylphenyl ether and calcium alkylbenzenesulfonate | 10 parts |

The above ingredients are uniformly mixed to obtain an emulsifiable concentrate.

Formulation Example 2

Dust Formulation

| | |
|---|---|
| Compound of the present invention | 3 parts |
| Clay powder | 82 parts |
| Diatomaceous earth powder | 15 parts |

The above ingredients are uniformly mixed to obtain a dust formulation.

Formulation Example 3

Granule

| | |
|---|---|
| Compound of the present invention | 5 parts |
| Mixed powder of bentonite and clay | 90 parts |
| Calcium ligninsulfonate | 5 parts |

The above ingredients are uniformly mixed, the mixture is kneaded with an appropriate amount of water and the kneaded product is granulated and dried to obtain granules.

Formulation Example 4

Wettable Powder

| | |
|---|---|
| Compound of the present invention | 20 parts |
| Kaolin and highly dispersed synthetic silicic acid | 75 parts |
| Mixture of polyoxyethylene nonylphenyl ether and calcium alkylbenzenesulfonate | 5 parts |

The above ingredients are uniformly mixed to obtain a wettable powder.

Test Example 1

Herbicidal Efficacy on Paddy Field Weeds of Pre-Emergence Stage (Pre)

75 cm² plastic pots were filled with the soil (clay loam). Seeds of *Scirpus juncoides*, a paddy weed, were planted, and they were covered with 75 cm³ of soil mixed with seeds of *Lindernia procumbens* and then filled with water depth of 5 cm. Next day, predetermined effective dosage (1000 g/ha as an active ingredient) of formulations comprising a compound of the present invention as an active ingredient which were prepared following Formulation Examples 1 to 4 was diluted with water and applied dropwise to the surface of the water. Then, they were brought up in a greenhouse and the herbicidal effect was examined after 21 days from the treatment by comparing with the result of an untreated group according to the following criteria. The results are shown in Table 8. In the table, "-" means that the test was not performed.

Criteria for herbicidal efficacy (growth inhibiting degree) and phytotoxicity.
5 . . . 100% herbicidal effect, phytotoxicity.
4 . . . 90%-99% herbicidal effect, phytotoxicity.
3 . . . 70%-89% herbicidal effect, phytotoxicity.
2 . . . 40%-69% herbicidal effect, phytotoxicity.
1 . . . 1%-39% herbicidal effect, phytotoxicity.
0 . . . 0% herbicidal effect, phytotoxicity.

Test Example 2

Herbicidal effect on paddy field weeds Of Post-Emergence Stage (Post)

75 cm² plastic pots were filled with the soil (clay loam). Seeds of *Scirpus juncoides* and *Echinochloa crus-galli*, paddy weeds, were planted, and they were covered with 75 cm³ of soil mixed with seeds of *Lindernia procumbens* and then filled with water depth of 5 cm and they were brought up in a greenhouse. When the test plants were at one-leaf stage, predetermined effective dosage (1000 g/ha as an active ingredient) of formulations comprising a compound of the present invention as an active ingredient was applied to the pot water. Then, they were brought up in a greenhouse and the herbicidal efficacy was examined after 21 days from the treatment by comparing with the result of an untreated group according to the criteria of Test Example 1. The results are shown in Table 8. In the table, "-" means that the test was not performed.

Test Example 3

Test of Phytotoxicity on Transplanted Paddy-Rice 75 cm² plastic pots were filled with the soil (clay loam) and filled with water depth of 5 cm and 2 rice plant seedlings (rice species: *Nihonbare*) at two-leaf stage were transplanted therein. They were brought up in a greenhouse and, after five days from the transplantation, predetermined effective dosage (1000 g/ha in terms of active ingredient) of formulations comprising a compound of the present invention as an active ingredient was applied to the pot water. Then, they were brought up in a greenhouse and the phytotoxicity was examined after 21 days from the treatment by comparing with the result of an untreated group according to the criteria of Test Example 1. The results are shown in Table 8. In the table, "-" means that the test was not performed.

TABLE 8

| Compound No. | Rice | Echinochloa crus-galli post | Scirpus juncoides pre | Scirpus juncoides post | Lindernia procumbens pre | Lindernia procumbens post |
|---|---|---|---|---|---|---|
| 1-1 | 3 | 4 | 4 | 4 | 4 | 4 |
| 1-4 | 3 | 4 | 4 | 4 | 4 | 4 |
| 1-5 | 3 | 4 | 4 | 4 | 4 | 4 |
| 1-6 | 3 | 4 | 4 | 4 | 4 | 4 |
| 1-16 | 3 | 4 | 4 | 4 | 4 | 4 |
| 1-17 | 3 | 4 | 4 | 4 | 4 | 4 |
| 1-23 | 2 | 4 | 4 | 4 | 4 | 4 |
| 1-25 | 3 | 4 | 4 | 4 | 4 | 4 |
| 1-26 | 2 | 4 | 4 | 4 | 4 | 4 |
| 1-27 | 2 | 4 | 4 | 4 | 4 | 4 |
| 1-28 | 2 | 4 | 4 | 4 | 4 | 4 |
| 1-34 | 2 | 4 | 4 | 4 | 4 | 4 |
| 1-35 | 2 | 4 | 4 | 4 | 4 | 4 |
| 1-36 | 2 | 4 | 4 | 4 | 4 | 4 |
| 1-39 | 2 | 4 | 4 | 4 | 4 | 4 |
| 1-45 | 2 | 4 | 4 | 4 | 4 | 4 |
| 1-47 | 3 | 4 | 4 | 4 | 4 | 4 |
| 1-50 | 3 | 4 | 4 | 4 | 4 | 4 |
| 1-51 | 3 | 4 | 4 | 4 | 4 | 4 |
| 1-52 | 3 | 4 | 4 | 4 | 4 | 4 |
| 1-53 | 2 | 4 | 4 | 4 | 4 | 4 |
| 1-54 | 1 | — | 4 | 4 | — | — |
| 1-55 | 2 | 4 | 4 | 4 | 4 | 4 |
| 1-58 | 2 | 4 | 4 | 4 | 4 | 4 |
| 1-63 | 2 | 4 | 4 | 4 | 4 | 4 |
| 1-64 | 2 | 4 | 4 | 4 | 4 | 4 |
| 1-69 | 3 | 4 | 4 | 4 | 4 | 4 |
| 1-71 | 3 | 4 | 4 | 4 | 4 | 4 |
| 1-74 | 3 | 4 | 4 | 4 | 4 | 4 |
| 1-75 | 3 | 4 | 4 | 4 | 4 | 4 |
| 1-80 | 1 | 4 | 4 | 4 | 4 | — |
| 1-81 | 1 | 4 | 4 | 4 | 5 | 5 |
| 1-82 | 0 | 4 | 5 | 4 | 5 | 5 |
| 1-85 | 1 | 4 | 4 | 4 | 4 | — |

TABLE 8-continued

| Compound No. | Rice | Echinochloa crus-galli post | Scirpus juncoides pre | Scirpus juncoides post | Lindernia procumbens pre | Lindernia procumbens post |
|---|---|---|---|---|---|---|
| 1-86 | 0 | 4 | 4 | 4 | 4 | 4 |
| 1-91 | 1 | 4 | 4 | 4 | 5 | 5 |
| 1-92 | 1 | 4 | 4 | 4 | 5 | 5 |
| 1-93 | 1 | 4 | 5 | 4 | 5 | 5 |
| 1-94 | 1 | — | 5 | 4 | 5 | 5 |
| 1-95 | 1 | — | 5 | 4 | 5 | 5 |
| 1-96 | 0 | 4 | 4 | 4 | 5 | 5 |
| 1-100 | 0 | 4 | 4 | — | 5 | 4 |
| 1-102 | 4 | 4 | 4 | 4 | 4 | 4 |
| 1-104 | 2 | 4 | 4 | 4 | 4 | 4 |
| 1-107 | 2 | 4 | 4 | 4 | 4 | 4 |
| 1-108 | 1 | — | 4 | 4 | 4 | 4 |
| 1-109 | 1 | 4 | 4 | 4 | 4 | 4 |
| 1-114 | 2 | 4 | 4 | 4 | 4 | 4 |
| 1-119 | 1 | — | 4 | 4 | 4 | 4 |
| 1-120 | 1 | 4 | 4 | 4 | 4 | 4 |
| 1-125 | 2 | 4 | 4 | 4 | 4 | 4 |
| 1-130 | 2 | 4 | 4 | 4 | 4 | 4 |
| 1-131 | 2 | 4 | 4 | 4 | 4 | 4 |
| 1-136 | 2 | 4 | 4 | 4 | 4 | 4 |
| 1-137 | 2 | 4 | 4 | 4 | 4 | 4 |
| 1-142 | 2 | 4 | 4 | 4 | 4 | 4 |
| 1-143 | 2 | 4 | 4 | 4 | 4 | 4 |
| 1-144 | 1 | — | 4 | 4 | 4 | 4 |
| 1-145 | 0 | — | 4 | 4 | — | — |
| 1-149 | 0 | — | — | — | — | — |
| 1-154 | 0 | — | — | — | 4 | — |
| 1-155 | 0 | — | 4 | 4 | 4 | 4 |
| 1-160 | 2 | — | 4 | 4 | 4 | 4 |
| 1-162 | 2 | — | 4 | 4 | 4 | 4 |
| 1-165 | 2 | — | 4 | 4 | 4 | — |
| 1-167 | 0 | — | 4 | — | — | — |
| 1-171 | 0 | — | — | — | — | — |
| 1-172 | 1 | — | 4 | 4 | 4 | 4 |
| 1-174 | 1 | — | 4 | 4 | 4 | 4 |
| 1-177 | 1 | — | 4 | 4 | 4 | 4 |
| 1-183 | 1 | — | 4 | 4 | 4 | 4 |
| 1-185 | 1 | 4 | 4 | 4 | 4 | 4 |
| 1-188 | 1 | 4 | 4 | 4 | 4 | — |
| 1-191 | 0 | 4 | — | — | 4 | — |
| 1-194 | 0 | — | — | — | — | — |
| 1-195 | 0 | — | 4 | 4 | 4 | 4 |
| 1-197 | 0 | — | 4 | 4 | 4 | 4 |
| 1-206 | 2 | — | 4 | 4 | 4 | 4 |
| 1-208 | 1 | 4 | 4 | 4 | 4 | 4 |
| 1-211 | 0 | 4 | 4 | 4 | 4 | 4 |
| 1-217 | 0 | — | 4 | 4 | 4 | 4 |
| 1-219 | 0 | — | 4 | 4 | 4 | 4 |
| 1-224 | 0 | — | — | — | 4 | — |
| 1-228 | 1 | — | 5 | 4 | 5 | 5 |
| 1-230 | 1 | 4 | 5 | 4 | 5 | 5 |
| 1-239 | 1 | 4 | — | 4 | 5 | 5 |
| 1-241 | 1 | 4 | — | 4 | 5 | 5 |
| 1-244 | 0 | — | — | — | 5 | 5 |
| 1-246 | 0 | — | — | — | 5 | — |
| 1-248 | 0 | 4 | — | — | — | 5 |
| 1-250 | 1 | — | 5 | 5 | 5 | 5 |
| 1-252 | 1 | — | 4 | 4 | 5 | 5 |
| 1-255 | 0 | — | — | — | 5 | 5 |
| 1-257 | 0 | — | 4 | — | 5 | 5 |
| 1-261 | 1 | 4 | 5 | 4 | 5 | 5 |
| 1-263 | 1 | 4 | 4 | 4 | 5 | 5 |
| 1-268 | 0 | — | 4 | 4 | 5 | 5 |
| 1-270 | 1 | — | — | 4 | 5 | 5 |
| 1-272 | 1 | 4 | 4 | 4 | 5 | 5 |
| 1-274 | 1 | 4 | 4 | 4 | 5 | 5 |
| 1-279 | 1 | — | — | 4 | 5 | 5 |
| 1-281 | 0 | — | — | 4 | 5 | 5 |
| 1-283 | 1 | 4 | 5 | 4 | 5 | 5 |
| 1-285 | 1 | 4 | 4 | 4 | 5 | 5 |
| 1-290 | 0 | — | — | 4 | 5 | 5 |
| 1-292 | 1 | 4 | — | 4 | 5 | 5 |
| 1-294 | 1 | — | 4 | 4 | 5 | 5 |
| 1-296 | 2 | 4 | 4 | 4 | 5 | 5 |
| 1-301 | 0 | — | — | — | 5 | 5 |
| 1-303 | 1 | 4 | — | 4 | 5 | 5 |

TABLE 8-continued

| Compound No. | Rice | Echinochloa crus-galli post | Scirpus juncoides pre | Scirpus juncoides post | Lindernia procumbens pre | Lindernia procumbens post |
|---|---|---|---|---|---|---|
| 1-305 | 1 | — | 4 | 4 | 5 | 5 |
| 1-307 | 0 | — | 4 | 4 | 5 | 5 |
| 1-312 | 0 | — | — | — | 5 | 5 |
| 1-314 | 1 | — | 4 | — | 5 | 5 |
| 1-316 | 1 | 4 | 4 | 4 | 5 | 5 |
| 1-317 | 1 | 4 | 4 | 4 | 5 | 5 |
| 1-318 | 1 | 4 | 4 | 4 | 5 | 5 |
| 1-321 | 1 | 4 | 4 | 4 | 5 | 5 |
| 1-323 | 0 | — | — | — | 5 | 5 |
| 1-327 | 4 | 4 | 5 | 4 | 5 | 5 |
| 1-329 | 2 | 4 | 5 | 4 | 5 | 5 |
| 1-332 | 3 | 4 | 5 | 4 | 5 | 5 |
| 1-338 | 0 | — | 4 | 4 | 4 | 5 |
| 1-339 | 0 | 4 | 4 | 4 | 5 | 5 |
| 1-340 | 0 | 4 | 4 | 4 | 5 | — |
| 1-343 | 0 | 4 | 5 | 4 | 5 | 5 |
| 1-349 | 3 | — | 5 | — | 5 | 5 |
| 1-350 | 2 | — | 5 | 4 | 5 | 5 |
| 1-351 | 1 | — | 4 | 4 | 5 | 5 |
| 1-360 | 1 | — | 5 | 4 | 5 | 5 |
| 1-361 | 1 | 4 | 5 | 4 | 5 | 5 |
| 1-362 | 1 | 4 | 4 | 4 | 5 | 5 |
| 1-369 | 0 | — | — | 4 | 5 | 5 |
| 1-371 | 4 | 4 | 5 | 4 | 5 | 5 |
| 1-373 | 3 | 4 | 5 | 4 | 5 | 5 |
| 1-376 | 4 | 4 | 5 | 4 | 5 | 5 |
| 1-377 | 3 | — | 4 | 4 | 5 | 5 |
| 1-382 | 4 | 4 | 5 | 4 | 5 | 5 |
| 1-384 | 4 | 4 | 5 | 4 | 5 | 5 |
| 1-387 | 4 | 5 | 5 | 5 | 5 | 5 |
| 1-388 | 2 | 5 | 5 | 4 | 5 | 5 |
| 1-393 | 1 | — | 5 | 4 | 5 | 5 |
| 1-394 | 1 | 4 | 5 | 4 | 5 | 5 |
| 1-395 | 1 | 4 | 5 | 4 | 5 | 5 |
| 1-404 | 1 | — | 4 | 4 | 5 | 5 |
| 1-406 | 1 | 5 | 5 | 4 | 5 | 5 |
| 1-415 | 1 | 5 | 5 | 4 | 5 | 5 |
| 1-416 | 1 | 5 | 5 | 4 | 5 | — |
| 1-417 | 4 | 4 | 5 | 4 | 5 | 5 |
| 1-419 | 4 | — | 5 | 4 | 5 | 5 |
| 1-422 | 4 | — | 5 | 4 | 5 | 5 |
| 1-423 | 4 | — | 4 | 4 | 5 | 5 |
| 1-428 | 1 | — | 5 | 4 | 5 | 5 |
| 1-429 | 1 | — | 4 | 4 | 5 | 5 |
| 1-430 | 1 | 4 | 5 | 4 | 5 | 5 |
| 1-439 | 2 | — | 5 | 4 | 5 | 5 |
| 1-440 | 2 | 4 | 4 | 4 | 5 | 5 |
| 1-441 | 1 | 5 | 5 | 4 | 5 | 5 |
| 1-450 | 4 | 4 | 5 | 4 | 5 | 5 |
| 1-452 | 4 | 4 | 5 | 4 | 5 | 5 |
| 1-455 | 3 | 5 | 5 | 4 | 5 | 5 |
| 1-456 | 3 | — | 5 | 4 | 5 | 5 |
| 1-461 | 1 | — | 5 | 4 | 5 | 5 |
| 1-463 | 1 | 4 | 5 | 4 | 5 | 5 |
| 1-494 | 4 | 4 | 5 | 4 | 5 | 5 |
| 1-496 | 3 | 4 | 5 | 4 | 5 | 5 |
| 1-499 | 3 | 4 | 5 | 4 | 5 | 5 |
| 1-501 | 3 | 5 | 5 | 4 | 5 | 5 |
| 1-506 | 4 | 4 | 5 | 4 | 5 | 5 |
| 2-1 | 3 | 4 | 4 | 4 | 4 | 4 |
| 2-3 | 2 | 4 | 4 | 4 | 4 | 4 |
| 2-4 | 2 | 4 | 4 | 4 | 4 | 4 |
| 2-5 | 2 | 4 | 4 | 4 | 4 | 4 |
| 2-6 | 2 | 4 | 4 | 4 | 4 | 4 |
| 2-12 | 1 | 4 | 4 | 4 | 4 | — |
| 2-14 | 1 | 4 | 4 | 4 | 4 | 4 |
| 2-17 | 0 | 4 | 4 | 4 | — | — |
| 2-23 | 3 | 4 | 4 | 4 | 4 | 4 |
| 2-24 | 3 | 4 | 4 | 4 | 4 | 4 |
| 2-25 | 3 | 4 | 4 | 4 | 4 | 4 |
| 2-27 | 2 | 4 | 4 | 4 | 4 | 4 |
| 2-28 | 3 | 4 | 4 | 4 | 4 | 4 |
| 2-34 | 2 | 4 | 4 | 4 | 4 | 4 |

The invention claimed is:
1. A compound of formula (I)

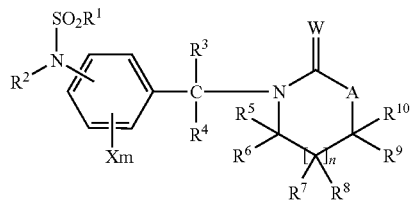

[Formula 1]

wherein $R^1$ represents a halo($C_1$-$C_8$)alkyl group; $R^2$ represents a hydrogen atom; a ($C_1$-$C_6$)alkoxycarbonyl($C_1$-$C_6$)alkyl group; a ($C_1$-$C_{18}$)alkylcarbonyl group; a halo($C_1$-$C_6$)alkylcarbonyl group; a phenylcarbonyl group; a substituted phenylcarbonyl group having 1 to 5 substituents, which may be the same or different, selected from Y as defined below; a ($C_1$-$C_{18}$)alkoxycarbonyl group; a ($C_2$-$C_{18}$)alkenyloxycarbonyl group; a ($C_2$-$C_{18}$)alkynyloxycarbonyl group; a halo($C_1$-$C_6$)alkoxycarbonyl group; a ($C_1$-$C_6$)alkoxy($C_1$-$C_6$)alkoxycarbonyl group; a ($C_1$-$C_6$)alkylthio($C_1$-$C_6$)alkoxycarbonyl group; a ($C_1$-$C_6$)alkylsulfinyl($C_1$-$C_6$)alkoxycarbonyl group; a ($C_1$-$C_6$)alkylsulfonyl($C_1$-$C_6$)alkoxycarbonyl group; a phenoxycarbonyl group; a substituted phenoxycarbonyl group having 1 to 5 substituents, which may be the same or different, selected from Y as defined below; a phenoxy($C_1$-$C_6$)alkylcarbonyl group; a substituted phenoxy($C_1$-$C_6$)alkylcarbonyl group having 1 to 5 substituents, which may be the same or different, selected from Y as defined below; a benzyloxycarbonyl group; a substituted benzyloxycarbonyl group having 1 to 5 substituents, which may be the same or different, selected from Y as defined below; a ($C_1$-$C_6$)alkylthiocarbonyl group; ($C_1$-$C_6$)alkylsulfonyl group; a halo($C_1$-$C_6$)alkylsulfonyl group; a phenylsulfonyl group; a substituted phenylsulfonyl group having 1 to 5 substituents, which may be the same or different, selected from Y as defined below; a ($C_1$-$C_6$)alkyl group; a ($C_2$-$C_6$)alkenyl group; a ($C_2$-$C_6$)alkynyl group; a phenyl($C_1$-$C_6$)alkyl group; a substituted phenyl($C_1$-$C_6$)alkyl group having 1 to 5 substituents on the ring, which may be the same or different, selected from Y as defined below; a phenylcarbonyl($C_1$-$C_6$)alkyl group; a substituted phenylcarbonyl($C_1$-$C_6$)alkyl group having 1 to 5 substituents on the ring, which may be the same or different, selected from Y as defined below; a ($C_1$-$C_8$)alkoxy($C_1$-$C_6$)alkyl group; a ($C_1$-$C_6$)alkoxy($C_1$-$C_6$)alkoxy($C_1$-$C_6$)alkyl group; a tri($C_1$-$C_6$)alkylsilyl($C_1$-$C_6$)alkoxy($C_1$-$C_6$)alkyl group which may be the same or different; a phenyl($C_1$-$C_6$)alkoxy($C_1$-$C_6$)alkyl group; a substituted phenyl($C_1$-$C_6$)alkoxy($C_1$-$C_6$)alkyl group having 1 to 5 substituents on the ring, which may be the same or different, selected from Y as defined below; a ($C_1$-$C_6$)alkylcarbonyloxy($C_1$-$C_6$)alkyl group; a phenylcarbonyloxy($C_1$-$C_6$)alkyl group; a substituted phenylcarbonyloxy($C_1$-$C_6$) alkyl group on the ring, which may be the same or different, selected from Y as defined below; a phenylcarbonyloxy($C_1$-$C_6$)alkoxy($C_1$-$C_6$)alkyl group; a substituted phenylcarbonyloxy($C_1$-$C_6$)alkoxy($C_1$-$C_6$)alkyl group having 1 to 5 substituents on the ring selected from Y as defined below; a ($C_1$-$C_6$)alkoxycarbonyloxy($C_1$-$C_6$)alkyl group; a mono($C_1$-$C_6$)alkylaminocarbonyloxy($C_1$-$C_6$)alkyl group; a di($C_1$-$C_6$)alkylaminocarbonyloxy($C_1$-$C_6$)alkyl group which may be the same or different and may be linked to each other to form a 5- to 8-membered ring; a phenylaminocarbonyloxy($C_1$-$C_6$)alkyl group; a substituted phenylaminocarbonyloxy($C_1$-$C_6$)alkyl group having 1 to 5 substituents on the ring, which may be the same or different, selected from Y as defined below; an N-($C_1$-$C_6$)alkyl-N-phenylaminocarbonyloxy($C_1$-$C_6$)alkyl group; a substituted N-($C_1$-$C_6$)alkyl-N-phenylaminocarbonyloxy($C_1$-$C_6$)alkyl group having 1 to 5 substituents on the ring, which may be the same or different, selected from Y as defined below; a phenylthio($C_1$-$C_6$)alkyl group; a substituted phenylthio($C_1$-$C_6$)alkyl group having 1 to 5 substituents on the ring, which may be the same or different, selected from Y as defined below; a phenylsulfonyl($C_1$-$C_6$)alkyl group; a substituted phenylsulfonyl($C_1$-$C_6$)alkyl group having 1 to 5 substituents on the ring, which may be the same or different, selected from Y as defined below; a phenyl($C_1$-$C_6$)alkylthio ($C_1$-$C_6$)alkyl group; a substituted phenyl($C_1$-$C_6$)alkylthio ($C_1$-$C_6$)alkyl group having 1 to 5 substituents on the ring, which may be the same or different, selected from Y as defined below; a phenyl($C_1$-$C_6$)alkylsulfonyl($C_1$-$C_6$)alkyl group; a substituted phenyl($C_1$-$C_6$)alkylsulfonyl($C_1$-$C_6$)alkyl group having 1 to 5 substituents on the ring, which may be the same or different, selected from Y as defined below; a ($C_1$-$C_6$)alkylthio($C_1$-$C_6$)alkyl group; a halo($C_1$-$C_6$)alkylthio($C_1$-$C_6$)alkyl group; a thiocyanato($C_1$-$C_6$)alkyl group; a heterocyclic($C_1$-$C_6$)alkyl group, wherein the heterocycle represents pyridine, pyridine-N-oxide, pyrimidine, pyrazine, triazine, furan, tetrahydrofuran, thiophene, tetrahydrothiophene, tetrahydropyran, tetrahydrothiopyran, oxazole, isoxazole, oxadiazole, thiazole, isothiazole, thiadiazole, imidazole, triazole, pyrazole, pyrrol, pyrrolidine, phthalimide or 2,3-dihydro-1,2-benzothiazol-3-one 1,1-dioxide; or a substituted heterocyclic($C_1$-$C_6$)alkyl group having 1 to 4 substituents on the ring, which may be the same or different, selected from Y as defined below, wherein the heterocycle is the same as above, $R^3$ and $R^4$, which may be the same or different, each represents a hydrogen atom; a ($C_1$-$C_6$)alkyl group; a ($C_3$-$C_6$)cycloalkyl group; a ($C_1$-$C_6$)alkoxy group; a halogen atom or a cyano group;

$R^5$ and $R^6$, which may be the same or different, each represents a hydrogen atom; a ($C_1$-$C_6$)alkyl group; a ($C_3$-$C_6$)cycloalkyl group; a ($C_1$-$C_6$)alkoxy group; a halogen atom; or a cyano group;

$R^7$, $R^8$, $R^9$ and $R^{10}$, which may be the same or different, each represents a hydrogen atom; a halogen atom; a ($C_1$-$C_6$)alkyl group; a ($C_3$-$C_6$)cycloalkyl group; a ($C_1$-$C_6$)alkoxy group; a halo($C_1$-$C_6$)alkyl group; a ($C_1$-$C_6$)alkoxy($C_1$-$C_6$)alkyl group; a ($C_1$-$C_6$)alkylcarbonyloxy($C_1$-$C_6$)alkyl group; a mono($C_1$-$C_6$)alkylamino ($C_1$-$C_6$)alkyl group; a di($C_1$-$C_6$)alkylamino ($C_1$-$C_6$)alkyl group which may be the same or different; a mono($C_1$-$C_6$)alkylaminocarbonyl($C_1$-$C_6$)alkyl group; a di($C_1$-$C_6$)alkylaminocarbonyl($C_1$-$C_6$)alkyl group which may be the same or different; a phenyl($C_1$-$C_6$)alkyl group; a substituted phenyl($C_1$-$C_6$)alkyl group having 1 to 5 substituents on the ring, which may be the same or different, selected from Y as defined below; a phenoxy($C_1$-$C_6$) alkyl group; a substituted phenoxy($C_1$-$C_6$)alkyl group having 1 to 5 substituents on the ring, which may be the same or different, selected from Y as defined below; a phenyl group; a substituted phenyl group having 1 to 5 substituents on the ring, which may be the same or different, selected from Y as defined below; a ($C_1$-$C_6$) alkoxycarbonyl group; a mono($C_1$-$C_6$)alkylaminocarbonyl group; a di($C_1$-$C_6$)alkylaminocarbonyl group which may be the same or different; a hydroxyl group; or a cyano group;

n represents 1 or 2;
A represents an oxygen atom or a sulfur atom;
W represents an oxygen atom or a sulfur atom;

X may be the same or different and represents a halogen atom; a $(C_1-C_6)$alkyl group; a $(C_2-C_6)$alkenyl group; a $(C_2-C_6)$alkynyl group; a cyclo$(C_3-C_6)$alkyl group; a halo$(C_1-C_6)$alkyl group; a cyclohalo$(C_3-C_6)$alkyl group; a $(C_1-C_6)$alkoxy group; a halo$(C_1-C_6)$alkoxy group; a $(C_1-C_6)$alkoxy$(C_1-C_6)$alkyl group; a halo$(C_1-C_6)$alkoxy$(C_1-C_6)$alkyl group; a $(C_1-C_6)$alkylthio group; a halo$(C_1-C_6)$alkylthio group; a $(C_1-C_6)$alkylthio$(C_1-C_6)$alkyl group; a halo$(C_1-C_6)$alkylthio$(C_1-C_6)$alkyl group; a $(C_1-C_6)$alkylsulfinyl group; a halo$(C_1-C_6)$alkylsulfinyl group; a $(C_1-C_6)$alkylsulfonyl group; a halo$(C_1-C_6)$alkylsulfonyl group; a phenyl group; a substituted phenyl group having 1 to 5 substituents, which may be the same or different, selected from Y as defined below; a phenoxy group; a substituted phenoxy group having 1 to 5 substituents, which may be the same or different, selected from Y as defined below; a phenylthio group; a substituted phenylthio group having 1 to 5 substituents, which may be the same or different, selected from Y as defined below; a phenylsulfinyl group; a substituted phenylsulfinyl group having 1 to 5 substituents, which may be the same or different, selected from Y as defined below; a phenylsulfonyl group; a substituted phenylsulfonyl group having 1 to 5 substituents, which may be the same or different, selected from Y as defined below; a $(C_1-C_6)$alkylcarbonyl group, a halo$(C_1-C_6)$alkylcarbonyl group, a phenylcarbonyl group; a substituted phenylcarbonyl group having 1 to 5 substituents, which may be the same or different, selected from Y as defined below; a $(C_1-C_6)$alkoxycarbonyl group; a carboxyl group; a mono$(C_1-C_6)$alkylaminocarbonyl group; di$(C_1-C_6)$alkylaminocarbonyl group which may be the same or different; a phenylaminocarbonyl group; a substituted phenylaminocarbonyl group having 1 to 5 substituents on the ring, which may be the same or different, selected from Y as defined below; a phenyl$(C_1-C_6)$alkylaminocarbonyl group; a substituted phenyl$(C_1-C_6)$alkylaminocarbonyl group having 1 to 5 substituents on the ring, which may be the same or different, selected from Y as defined below; a hydroxyl group or a cyano group; and m represents an integer of 0 to 4, and X may be taken together with an adjacent carbon atom on the benzene ring to form a 5- or 6-membered ring through a $(C_1-C_4)$alkylene group which may be the same or different and may be interrupted with one or two hetero atoms selected from an oxygen atom, a sulfur atom, or a nitrogen atom which may be substituted with a hydrogen atom, a $(C_1-C_6)$alkyl group, a $(C_2-C_6)$alkenyl group, a $(C_2-C_6)$alkynyl group or a cyclo$(C_3-C_6)$alkyl group;

Y, which may be the same or different, represents 1 to 5 substituents selected from a halogen atom; a nitro group; a $(C_1-C_6)$alkyl group; a $(C_2-C_6)$alkenyl group; a $(C_2-C_6)$alkynyl group; a cyclo$(C_3-C_6)$alkyl group; a halo$(C_1-C_6)$alkyl group; a cyclohalo$(C_3-C_6)$alkyl group; a $(C_1-C_6)$alkoxy group; a halo$(C_1-C_6)$alkoxy group; a cyano$(C_1-C_6)$alkoxy group; a $(C_1-C_6)$alkoxy$(C_1-C_6)$alkoxy group; a $(C_1-C_6)$alkylthio group; a halo$(C_1-C_6)$alkylthio group; a $(C_1-C_6)$alkylsulfinyl group; a halo$(C_1-C_6)$alkylsulfinyl group; a $(C_1-C_6)$alkylsulfonyl group; a halo$(C_1-C_6)$alkylsulfonyl group; a phenyl group; a substituted phenyl group having 1 to 5 substituents, which may be the same or different, selected from a halogen atom, a $(C_1-C_6)$alkyl group, a $(C_2-C_6)$alkenyl group, a $(C_2-C_6)$alkynyl group, a cyclo$(C_3-C_6)$alkyl group, a halo$(C_1-C_6)$alkyl group, a cyclohalo$(C_3-C_6)$alkyl group, a $(C_1-C_6)$alkoxy group, a halo$(C_1-C_6)$alkoxy group, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group, a halo$(C_1-C_6)$alkylsulfonyl group, a $(C_1-C_6)$alkylcarbonyl group, a halo$(C_1-C_6)$alkylcarbonyl group, a $(C_1-C_6)$alkoxycarbonyl group, a carboxyl group, a mono$(C_1-C_6)$alkylaminocarbonyl group, a di$(C_1-C_6)$alkylaminocarbonyl group which may be the same or different, a hydroxyl group or a cyano group; a heterocyclic group which represents a pyridyl group, a pyridine-N-oxide group, a pyrimidinyl group, a pyrazinyl group, a triazinyl group, a furyl group, a tetrahydrofuryl group, a thienyl group, a tetrahydrothienyl group, a tetrahydropyranyl group, a tetrahydrothiopyranyl group, an oxazolyl group, an isooxazolyl group, an oxadiazolyl group, an thiazolyl group, an isothiazolyl group, an thiadiazolyl group, an imidazolyl group, a triazolyl group, a pyrazolyl group, a pyrrolyl group or a pyrrolidinyl group; a substituted heterocyclic group as defined above, having one or more substituents on the ring, which may be the same or different, selected from a halogen atom, a $(C_1-C_6)$alkyl group, a $(C_2-C_6)$alkenyl group, a $(C_2-C_6)$alkynyl group, a cyclo$(C_3-C_6)$alkyl group, a halo$(C_1-C_6)$alkyl group, a cyclohalo$(C_3-C_6)$alkyl group, a $(C_1-C_6)$alkoxy group, a halo$(C_1-C_6)$alkoxy group, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group, a halo$(C_1-C_6)$alkylsulfonyl group, a $(C_1-C_6)$alkylcarbonyl group, a halo$(C_1-C_6)$alkylcarbonyl group, a $(C_1-C_6)$alkoxycarbonyl group, a carboxyl group, a mono$(C_1-C_6)$alkylaminocarbonyl group, di$(C_1-C_6)$alkylaminocarbonyl group which may be the same or different, a hydroxyl group or a cyano group; a phenoxy group; a substituted phenoxy group having 1 to 5 substituents, which may be the same or different, selected from a halogen atom, a $(C_1-C_6)$alkyl group, a $(C_2-C_6)$alkenyl group, a $(C_2-C_6)$alkynyl group, a cyclo$(C_3-C_6)$alkyl group, a halo$(C_1-C_6)$alkyl group, a cyclohalo$(C_3-C_6)$alkyl group, a $(C_1-C_6)$alkoxy group, a halo$(C_1-C_6)$alkoxy group, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group, a halo$(C_1-C_6)$alkylsulfonyl group, a $(C_1-C_6)$alkylcarbonyl group, a halo$(C_1-C_6)$alkylcarbonyl group, an alkoxycarbonyl group, a carboxyl group, a mono$(C_1-C_6)$alkylaminocarbonyl group, a di$(C_1-C_6)$alkylaminocarbonyl group which may be the same or different, a hydroxyl group or a cyano group; a phenylthio group; a substituted phenylthio group having 1 to 5 substituents, which may be the same or different, selected from a halogen atom, a $(C_1-C_6)$alkyl group, a $(C_2-C_6)$alkenyl group, a $(C_2-C_6)$alkynyl group, a cyclo$(C_3-C_6)$alkyl group, a halo$(C_1-C_6)$alkyl group, a cyclohalo$(C_3-C_6)$alkyl group, a $(C_1-C_6)$alkoxy group, a halo$(C_1-C_6)$alkoxy group, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group, a halo$(C_1-C_6)$alkylsulfonyl group, a $(C_1-C_6)$alkylcarbonyl group, a halo$(C_1-C_6)$alkylcarbonyl group, a $(C_1-C_6)$alkoxycarbonyl group, a carboxyl group, a mono$(C_1-C_6)$alkylaminocarbonyl group, a di$(C_1-C_6)$alkylaminocarbonyl group which may be the same or different, a hydroxyl group or a cyano group; a phenylsulfinyl group; a substituted phenylsulfinyl group having 1 to 5 substituents, which may be the same or different, selected from a halogen atom, a $(C_1-C_6)$alkyl group, a $(C_2-C_6)$alkenyl group, a $(C_2-C_6)$alkynyl group, a cyclo$(C_3-C_6)$alkyl group, a halo$(C_1-C_6)$alkyl group, a cyclohalo$(C_3-C_6)$alkyl group, a $(C_1-C_6)$alkoxy group, a halo$(C_1-C_6)$alkoxy group, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group, a halo$(C_1-C_6)$alkylsulfonyl group, a $(C_1-C_6)$alkylcarbonyl group, a halo$(C_1-C_6)$alkylcarbonyl group, a $(C_1-C_6)$alkoxycarbonyl group, a carboxyl group, a mono$(C_1-C_6)$alkylaminocarbonyl group, a di$(C_1-C_6)$alkylaminocarbonyl group which may be the same or different, a hydroxyl group or a cyano group; a phenylsulfonyl group; a substituted phenylsulfonyl group having 1 to 5 substituents, which may be the same or different, selected from a halogen atom, a $(C_1-C_6)$alkyl group, a $(C_2-C_6)$alkenyl group, a $(C_2-C_6)$alkynyl group, a cyclo$(C_1-C_6)$alkyl group, a halo$(C_1-C_6)$alkyl group, a cyclohalo$(C_3-C_6)$alkyl group, a $(C_1-C_6)$alkoxy group, a halo$(C_1-C_6)$alkoxy group, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group, a halo$(C_1-C_6)$alkylsulfonyl group, a $(C_1-C_6)$alkylcarbonyl group, a halo$(C_1-C_6)$alkylcarbonyl group, a $(C_1-C_6)$alkoxycarbonyl group, a carboxyl group, a mono$(C_1-C_6)$alkylaminocarbonyl group, a di$(C_1-C_6)$alkylaminocarbonyl group which may be the same or different, a hydroxyl group or a cyano group; a $(C_1-C_6)$alkylcarbonyl group; a halo$(C_1-C_6)$alkylcarbonyl group; a phenylcarbonyl group; a substituted phenylcarbonyl group having 1 to 5 substituents, which may be the same or different, selected from a halogen atom, a $(C_1-C_6)$alkyl group, a $(C_2-C_6)$alkenyl group, a $(C_2-C_6)$alkynyl group, a cyclo$(C_3-C_6)$alkyl group, a halo$(C_1-C_6)$alkyl group, a cyclohalo$(C_3-C_6)$alkyl group, a $(C_1-C_6)$alkoxy group, a halo$(C_1-C_6)$alkoxy group, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group, a halo$(C_1-C_6)$alkylsulfonyl group, a $(C_1-C_6)$alkylcarbonyl group, a halo$(C_1-C_6)$alkylcarbonyl group, a $(C_1-C_6)$alkoxycarbonyl group, a carboxyl group, a mono$(C_1-C_6)$alkylaminocarbonyl group, a di$(C_1-C_6)$alkylaminocarbonyl group which may be the same or different, a hydroxyl group or a cyano group; a $(C_1-C_6)$alkoxycarbonyl group; a carboxyl group; a mono$(C_1-C_6)$alkylaminocarbonyl group; a di$(C_1-C_6)$alkylaminocarbonyl group which may be the same or different; a phenylaminocarbonyl group; a substituted phenylaminocarbonyl group having 1 to 5 substituents on the ring, which may be the same or different, selected from a halogen atom, a $(C_1-C_6)$alkyl group, a $(C_2-C_6)$alkenyl group, a $(C_2-C_6)$alkynyl group, a cyclo$(C_3-C_6)$alkyl group, a halo$(C_1-C_6)$alkyl group, a cyclohalo$(C_3-C_6)$alkyl group, a $(C_1-C_6)$alkoxy group, a halo$(C_1-C_6)$alkoxy group, a $(C_1-C_6)$alkylthio group, a halo$(C_1-C_6)$alkylthio group, a $(C_1-C_6)$alkylsulfinyl groups, a halo$(C_1-C_6)$alkylsulfinyl group, a $(C_1-C_6)$alkylsulfonyl group, a halo$(C_1-C_6)$alkylsulfonyl group, a $(C_1-C_6)$alkylcarbonyl group, a halo$(C_1-C_6)$alkylcarbonyl group, a $(C_1-C_6)$alkoxycarbonyl group, a carboxyl group, a mono$(C_1-C_6)$alkylaminocarbonyl group, a di$(C_1-C_6)$alkylaminocarbonyl group which may be the same or different, a hydroxyl group or a cyano group; a phenyl$(C_1-C_6)$alkylaminocarbonyl group; a substituted phenyl$(C_1-C_6)$alkylaminocarbonyl group having 1 to 5 substituents on the ring, which may be the same or different, selected from a halogen atom, a $(C_1-C_6)$alkyl group, a $(C_2-C_6)$alkenyl group, a $(C_2-C_6)$alkynyl group, a cyclo$(C_3-C_6)$alkyl group, a halo$(C_1-C_6)$alkyl group, a cyclohalo$(C_3-C_6)$alkyl group, a $(C_1-C_6)$alkoxy group, a halo$(C_1-C_6)$alkoxy group, a $(C_1-C_6)$alkylthio group, a halo$(C_1-C_6)$alkylthio group, a $(C_1-C_6)$alkylsulfinyl group, a halo$(C_1-C_6)$alkylsulfinyl group, a $(C_1-C_6)$alkylsulfonyl group, a halo$(C_1-C_6)$alkylsulfonyl group, a $(C_1-C_6)$alkylcarbonyl group, a halo$(C_1-C_6)$alkylcarbonyl group, a $(C_1-C_6)$alkoxycarbonyl group, a carboxyl group, a mono$(C_1-C_6)$alkylaminocarbonyl group, a di$(C_1-C_6)$alkylaminocarbonyl group which may be the same or different, a hydroxyl group or a cyano group; a hydroxyl group or a cyano group, and Y may be taken together with an adjacent carbon atom on the benzene ring to form a 5- or 6-membered ring through a $(C_1-C_4)$alkylene group which may be the same or different and may be interrupted with one or two hetero atoms selected from an oxygen atom, a sulfur atom, or a nitrogen atom which may be substituted with a hydrogen atom, a $(C_1-C_6)$alkyl group, a $(C_2-C_6)$alkenyl group, a $(C_2-C_6)$alkynyl group or a cyclo $(C_3-C_6)$alkyl group, or a herbicidally acceptable salt thereof.

2. The compound or a herbicidally acceptable salt thereof according to claim 1, wherein $R^1$ is a fluoro$(C_1-C_6)$alkyl group; $R^2$ a hydrogen atom; a $(C_1-C_6)$alkyl group; a $(C_1-C_6)$alkoxycarbonyl$(C_1-C_6)$alkyl group; a $(C_1-C_{18})$alkylcarbonyl group; a halo$(C_1-C_6)$alkylcarbonyl group; a $(C_1-C_{18})$alkoxycarbonyl group; a halo$(C_1-C_6)$alkoxycarbonyl group; a $(C_1-C_8)$alkoxy$(C_1-C_6)$alkyl group; a $(C_1-C_6)$alkoxy$(C_1-C_6)$alkoxy$(C_1-C_6)$alkyl group; a $(C_1-C_6)$alkylcarbonyloxy$(C_1-C_6)$alkyl group; or a $(C_1-C_6)$alkoxycarbonyloxy$(C_1-C_6)$alkyl group; $R^3$, $R^4$, $R^5$ and $R^6$ are hydrogen atoms; $R^7$ and $R^8$, which may be the same or different, each represents a hydrogen atom; a halogen atom; a $(C_1-C_6)$alkyl group; a $(C_3-C_6)$cycloalkyl group; a $(C_1-C_6)$alkoxy group; a halo$(C_1-C_6)$alkyl group; or a $(C_1-C_6)$alkoxy$(C_1-C_6)$alkyl group; $R^9$ and $R^{10}$, which may be the same or different, each represents a hydrogen atom; a halogen atom; a $(C_1-C_6)$alkyl group; a $(C_3-C_6)$cycloalkyl group; a $(C_1-C_6)$alkoxy group; a halo$(C_1-C_6)$alkyl group; a $(C_1-C_6)$alkoxy$(C_1-C_6)$alkyl group; a phenyl$(C_1-C_6)$alkyl group; a substituted phenyl$(C_1-C_6)$alkyl group having 1 to 5 substituents on the ring, which may be the same or different, selected from a halogen atom, a $(C_1-C_6)$alkyl group, a halo$(C_1-C_6)$alkyl group, a $(C_1-C_6)$alkoxy group or a halo$(C_1-C_6)$alkoxy group; a phenyl group; a substituted phenyl having 1 to 5 substituents selected from a halogen atom, a $(C_1-C_6)$alkyl group, a halo$(C_1-C_6)$alkyl group, a $(C_1-C_6)$alkoxy group or a halo$(C_1-C_6)$alkoxy group; m represents 0; A represents an oxygen atom; and W represents an oxygen atom or a sulfur atom.

3. The compound or a herbicidally acceptable salt thereof according to claim 1, wherein $R^1$ is a trifluoromethyl group; $R^2$ a hydrogen atom; a $(C_1-C_6)$alkyl group; a $(C_1-C_{18})$alkoxycarbonyl group; a halo$(C_1-C_6)$alkoxycarbonyl group; a $(C_1-C_8)$alkoxy$(C_1-C_6)$alkyl group; or a $(C_1-C_6)$alkylcarbonyloxy$(C_1-C_6)$alkyl group; $R^3$, $R^4$, $R^5$ and $R^6$ are hydrogen atoms; $R^7$ and $R^8$, which may be the same or different, each represents a hydrogen atom; or a $(C_1-C_6)$alkyl group; $R^9$ and $R^{10}$, which may be the same or different, each represents a hydrogen atom; a $(C_1-C_6)$alkyl group; a $(C_3-C_6)$cycloalkyl group; a halo$(C_1-C_6)$alkyl group; a phenyl group; a substituted phenyl group having 1 to 5 substituents, which may be the same or different, selected from a halogen atom, a $(C_1-C_6)$alkyl group or a $(C_1-C_6)$alkoxy group; m represents 0; A represents an oxygen atom; and W represents an oxygen atom or a sulfur atom.

4. A herbicide comprising a compound according to claim 1, and a herbicidally acceptable carrier.

5. A method of treating the soil, a rice field or treating plants by applying an effective amount of the herbicide according to claim 4 to the soil or rice field in need of such treatment or plants to be killed.

\* \* \* \* \*